United States Patent
Iversen

(10) Patent No.: US 10,017,763 B2
(45) Date of Patent: Jul. 10, 2018

(54) DSRNA MOLECULES COMPRISING OLIGONUCLEOTIDE ANALOGS HAVING MODIFIED INTERSUBUNIT LINKAGES AND/OR TERMINAL GROUPS

(75) Inventor: Patrick L. Iversen, Corvallis, OR (US)

(73) Assignee: SAREPTA THERAPEUTICS, INC., Cambridge, MA (US)

(*) Notice: Subject to any disclaimer, the term of this patent is extended or adjusted under 35 U.S.C. 154(b) by 151 days.

(21) Appl. No.: 13/819,634

(22) PCT Filed: Sep. 2, 2011

(86) PCT No.: PCT/US2011/050403
§ 371 (c)(1),
(2), (4) Date: Jul. 15, 2013

(87) PCT Pub. No.: WO2012/031243
PCT Pub. Date: Mar. 8, 2012

(65) Prior Publication Data
US 2013/0288369 A1    Oct. 31, 2013

Related U.S. Application Data

(60) Provisional application No. 61/380,105, filed on Sep. 3, 2010.

(51) Int. Cl.
*C12N 15/113* (2010.01)

(52) U.S. Cl.
CPC ........ *C12N 15/113* (2013.01); *C12N 2310/14* (2013.01); *C12N 2310/314* (2013.01); *C12N 2310/3233* (2013.01); *C12N 2310/344* (2013.01); *C12N 2310/3513* (2013.01)

(58) Field of Classification Search
CPC .................................................. C12N 15/113
See application file for complete search history.

(56) References Cited

U.S. PATENT DOCUMENTS

| | | |
|---|---|---|
| 5,034,506 A | 7/1991 | Summerton et al. |
| 5,138,045 A | 8/1992 | Cook et al. |
| 5,142,047 A | 8/1992 | Summerton et al. |
| 5,166,315 A | 11/1992 | Summerton et al. |
| 5,185,444 A | 2/1993 | Summerton et al. |
| 5,212,295 A | 5/1993 | Cook |
| 5,217,866 A | 6/1993 | Summerton et al. |
| 5,218,105 A | 6/1993 | Cook et al. |
| 5,223,168 A | 6/1993 | Holt |
| 5,378,825 A | 1/1995 | Cook et al. |
| 5,386,023 A | 1/1995 | Sanghvi et al. |
| 5,457,191 A | 10/1995 | Cook et al. |
| 5,459,255 A | 10/1995 | Cook et al. |
| 5,506,337 A | 4/1996 | Summerton et al. |
| 5,506,351 A | 4/1996 | McGee |
| 5,521,063 A | 5/1996 | Summerton et al. |
| 5,521,302 A | 5/1996 | Cook |
| 5,539,082 A | 7/1996 | Nielsen et al. |
| 5,541,307 A | 7/1996 | Cook et al. |
| 5,554,746 A | 9/1996 | Ravikumar et al. |
| 5,571,902 A | 11/1996 | Ravikumar et al. |
| 5,576,302 A | 11/1996 | Cook et al. |
| 5,578,718 A | 11/1996 | Cook et al. |
| 5,580,767 A | 12/1996 | Cowsert et al. |
| 5,587,361 A | 12/1996 | Cook et al. |
| 5,587,469 A | 12/1996 | Cook et al. |
| 5,587,470 A | 12/1996 | Cook et al. |
| 5,599,797 A | 2/1997 | Cook et al. |
| 5,602,240 A | 2/1997 | De Mesmaeker et al. |
| 5,608,046 A | 3/1997 | Cook et al. |
| 5,610,289 A | 3/1997 | Cook et al. |
| 5,698,685 A | 12/1997 | Summerton et al. |
| 5,702,891 A | 12/1997 | Kolberg et al. |
| 5,734,039 A | 3/1998 | Calabretta et al. |
| 5,749,847 A | 5/1998 | Zewert et al. |
| 5,801,154 A | 9/1998 | Baracchini et al. |
| 5,892,023 A | 4/1999 | Pirotzky et al. |
| 5,955,318 A | 9/1999 | Simons et al. |
| 6,030,954 A | 2/2000 | Wu et al. |
| 6,060,456 A | 5/2000 | Arnold, Jr. et al. |
| 6,133,246 A | 10/2000 | McKay et al. |
| 6,174,868 B1 | 1/2001 | Anderson et al. |
| 6,228,579 B1 | 5/2001 | Zyskind et al. |
| 6,239,265 B1 | 5/2001 | Cook |

(Continued)

FOREIGN PATENT DOCUMENTS

| | | |
|---|---|---|
| JP | H05-504563 A | 7/1993 |
| JP | 2002-167441 A | 6/2002 |

(Continued)

OTHER PUBLICATIONS

Kumar et al., Microbiol. Mol. Biol. Rev., 1998, 62(4), p. 1415-1434.*
Agrawal et al., "Antisense therapeutics: is it as simple as complementary base recognition?," *Molecular Med. Today* 6:72-81, 2000.
Agrawal, "Antisense oligonucleotides: towards clinical trials," *Tibtech* 14(10):376-387, 1996.
Bramhill, "Bacterial Cell Division," *Annu Rev Cell Dev Biol* 13:395-424, 1997.
Crooke, Antisense Research and Applications, ed. Springer, 1999, Chapter 1, "Basic Principles of Antisense Therapeutics," pp. 1-50.
Deere et al., "Antisense Phosphorodiamidate Morpholino Oligomer Length and Target Position Effects on Gene-Specific Inhibition in *Escherichia coli*," *Antimicrobial Agents and Chemotherapy* 49(1):249-255, Jan. 2005.
Donachie, "The Cell Cycle of *Escherichia coli*," *Annu. Rev. Microbiol.* 47:199-230, 1993.
Dryselius et al., "The Translation Start Codon Region Is Sensitive to Antisense PNA Inhibition in *Escherichia coli*," *Oligonucleotides* 13:427-433, 2003.

(Continued)

Primary Examiner — Jonathan S Lau
(74) Attorney, Agent, or Firm — Brian C. Trinque; Lathrop Gage LLP

(57) ABSTRACT

Morpholino oligomers containing modified intersubunit linkages and/or terminal groups are provided for use within dsRNA molecules. The oligomers are oligonucleotide analogs containing predetermined sequences of base-pairing moieties. Also provided are such oligomers conjugated to peptide transporter moieties, where the transporters are preferably composed of arginine subunits, or arginine dimers, alternating with neutral amino acid subunits.

13 Claims, No Drawings

(56) References Cited

U.S. PATENT DOCUMENTS

| | | |
|---|---|---|
| 6,245,747 B1 | 6/2001 | Porter et al. |
| 6,262,241 B1 | 7/2001 | Cook et al. |
| 6,306,993 B1 | 10/2001 | Rothbard et al. |
| 6,365,351 B1 | 4/2002 | Iversen |
| 6,391,542 B1 | 5/2002 | Anderson et al. |
| 6,495,663 B1 | 12/2002 | Rothbard et al. |
| 6,548,651 B1 | 4/2003 | Nielsen et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen |
| 7,094,765 B2 | 8/2006 | Iversen et al. |
| 7,115,374 B2 | 10/2006 | Linnen |
| 7,402,574 B2 | 7/2008 | Iversen et al. |
| 7,507,196 B2 | 3/2009 | Stein et al. |
| 7,524,829 B2 | 4/2009 | Stein et al. |
| 7,582,615 B2 | 9/2009 | Neuman et al. |
| 7,625,873 B2 | 12/2009 | Geller et al. |
| 7,790,694 B2 | 9/2010 | Geller et al. |
| 7,807,801 B2 | 10/2010 | Iversen et al. |
| 7,838,657 B2 | 11/2010 | Singh et al. |
| 7,943,762 B2 | 5/2011 | Weller et al. |
| 8,030,291 B2 | 10/2011 | Stein et al. |
| 8,030,292 B2 | 10/2011 | Stein et al. |
| 8,067,569 B2 | 11/2011 | Iversen et al. |
| 8,076,476 B2 | 12/2011 | Reeves et al. |
| 8,084,433 B2 | 12/2011 | Iversen et al. |
| 8,129,352 B2 | 3/2012 | Iversen et al. |
| 8,168,604 B2 | 5/2012 | Stein et al. |
| 8,198,429 B2 | 6/2012 | Iversen et al. |
| 8,299,206 B2 | 10/2012 | Fox et al. |
| 8,329,668 B2 | 12/2012 | Stein et al. |
| 8,779,128 B2 * | 7/2014 | Hanson .......... C07F 9/5727 544/121 |
| 2003/0095953 A1 | 5/2003 | Cabot et al. |
| 2003/0166588 A1 | 9/2003 | Iversen et al. |
| 2003/0171335 A1 | 9/2003 | Stein et al. |
| 2003/0175767 A1 | 9/2003 | Davis et al. |
| 2003/0224353 A1 | 12/2003 | Stein et al. |
| 2004/0110296 A1 | 6/2004 | Vargeese et al. |
| 2004/0161844 A1 | 8/2004 | Baker et al. |
| 2004/0259108 A1 | 12/2004 | Linnen et al. |
| 2005/0096291 A1 | 5/2005 | Iversen et al. |
| 2005/0107312 A1 | 5/2005 | Keicher et al. |
| 2005/0176661 A1 | 8/2005 | Vaillant et al. |
| 2005/0234002 A1 | 10/2005 | Mourich et al. |
| 2006/0104989 A1 | 5/2006 | Edwards et al. |
| 2006/0148747 A1 | 7/2006 | Stein et al. |
| 2006/0149046 A1 | 7/2006 | Arar |
| 2006/0269911 A1 | 11/2006 | Iversen et al. |
| 2007/0004661 A1 | 1/2007 | Stein et al. |
| 2007/0021362 A1 | 1/2007 | Geller et al. |
| 2007/0037763 A1 | 2/2007 | Stein et al. |
| 2007/0066556 A1 | 3/2007 | Stein et al. |
| 2007/0082336 A1 | 4/2007 | Johnsson et al. |
| 2007/0265214 A1 | 11/2007 | Stein et al. |
| 2008/0160225 A1 | 7/2008 | Lowe et al. |
| 2009/0082547 A1 | 3/2009 | Iversen et al. |
| 2009/0088562 A1 * | 4/2009 | Weller .......... C07H 21/00 536/24.5 |
| 2009/0131624 A1 | 5/2009 | Reeves et al. |
| 2009/0131632 A1 | 5/2009 | Fox et al. |
| 2010/0016215 A1 | 1/2010 | Moulton et al. |
| 2010/0105120 A1 | 4/2010 | Zebala |
| 2010/0105865 A1 | 4/2010 | Telford et al. |
| 2010/0130591 A1 | 5/2010 | Sazani et al. |
| 2010/0137408 A1 | 6/2010 | Geller et al. |
| 2010/0234280 A1 | 9/2010 | Geller et al. |
| 2010/0234281 A1 | 9/2010 | Weller et al. |
| 2011/0118334 A1 | 5/2011 | Iversen |
| 2011/0224283 A1 | 9/2011 | Iversen |
| 2012/0065169 A1 | 3/2012 | Hanson et al. |
| 2012/0122769 A1 | 5/2012 | Iversen |
| 2012/0289457 A1 | 11/2012 | Hanson |
| 2013/0197220 A1 | 8/2013 | Ueda |
| 2013/0288369 A1 | 10/2013 | Iversen |
| 2013/0289091 A1 | 10/2013 | Geller et al. |
| 2014/0024698 A1 | 1/2014 | Kole et al. |
| 2014/0213737 A1 | 7/2014 | Weller et al. |
| 2014/0330006 A1 | 11/2014 | Hanson et al. |
| 2015/0073140 A1 | 3/2015 | Hanson et al. |
| 2015/0080340 A1 | 3/2015 | Hanson |

FOREIGN PATENT DOCUMENTS

| | | |
|---|---|---|
| JP | 2004-537517 A | 12/2004 |
| JP | 2008-509701 A | 4/2008 |
| JP | 2008-513012 A | 5/2008 |
| JP | 2010-505741 A | 2/2010 |
| WO | 91/09033 A1 | 6/1991 |
| WO | 93/01286 A2 | 1/1993 |
| WO | 97/40854 A2 | 11/1997 |
| WO | 2000/056740 A1 | 9/2000 |
| WO | 01/49775 A2 | 7/2001 |
| WO | 01/76636 A2 | 10/2001 |
| WO | 02/079467 A2 | 10/2002 |
| WO | 02/094250 A2 | 11/2002 |
| WO | 2002/092617 A1 | 11/2002 |
| WO | 2003/033657 A2 | 4/2003 |
| WO | 2004/097102 A2 | 11/2004 |
| WO | 2005/007805 A2 | 1/2005 |
| WO | 2005/030800 A2 | 4/2005 |
| WO | 2005065268 A2 | 7/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/085973 A2 | 8/2006 |
| WO | 2006/086667 A2 | 8/2006 |
| WO | 2006/121951 A2 | 11/2006 |
| WO | 2007/002390 A2 | 1/2007 |
| WO | 2007/009094 A2 | 1/2007 |
| WO | 2007/030576 A2 | 3/2007 |
| WO | 2007/030691 A2 | 3/2007 |
| WO | 2007/103529 A2 | 9/2007 |
| WO | 2008/018795 A1 | 2/2008 |
| WO | 2008/036127 A2 | 3/2008 |
| WO | 2008/036406 A1 | 3/2008 |
| WO | 2009/064471 A1 | 5/2009 |
| WO | 2010/019847 A2 | 2/2010 |
| WO | 2010/048586 A1 | 4/2010 |
| WO | 2010/120820 A1 | 10/2010 |
| WO | 2010/148249 A1 | 12/2010 |
| WO | 2011/060320 A1 | 5/2011 |
| WO | 2011/150408 A2 | 12/2011 |

OTHER PUBLICATIONS

Galloway et al., "A mutant of *Escherichia coli* defective in the first step of endotoxin biosynthesis," *J. Biol. Chem.* 265(11):6394-6402, 1990.

Geller et al., "Antisense Antibacterial Method and Compound," Office Action, dated Sep. 29, 2010, U.S. Appl. No. 11/173,847, 25 pages.

Geller et al., "Antisense phosphorodiamidate morpholino oligomer inhibits viability of *Escherichia coli* in pure culture and in mouse peritonitis," *Journal of Antimicrobial Chemotherapy* 55:938-988, 2005.

Geller et al., "Inhibition of Gene Expression in *Escherichia coli* by Antisense Phosphorodiamidate Morpholino Oligomers," *Antimicrobial Agents and Chemotherapy* 47(10):3233-3239, Oct. 2003.

Geller et al., "Translocation of Pro-OmpA across Inner Membrane Vesicles of *Escherichia coli* Occurs in Two Consecutive Energetically Distinct Steps," *The Journal of Biological Chemistry* 264(28):16465-16469, 1989.

GenBank Accession No. AF074613, retrieved Jul. 15, 2010, from http://www.ncbi.nlm.nih.gov/nuccore/3822114. 45 pages.

GenBank Accession No. AJ007716, retrieved Jul. 15, 2010, from http://www.ncbi.nlm.nih.gov/nuccore/4775309. 4 pages.

GenBank Accession No. X97542.1, retrieved Jul. 15, 2010, from http://www.ncbi.nlm.hih.gov/nuccore/2244635. 4 pages.

(56) References Cited

OTHER PUBLICATIONS

GenBank Accession No. Y11275.1, retrieved Jul. 15, 2010, from http://www.ncbi.nlm.nih.gov/nuccore/4127812. 4 pages.
GenBank Accession No. AB011549, retrieved Jul. 15, 2010, from http://www.ncbi.nlm.nih.gov/nuccore/4589740. 35 pages.
Gerdes et al., "Experimental Determination and System Level Analysis of Essential Genes in Escherichia coli MG1655," Journal of Bacteriology 185(19):5673-5684, Oct. 2003.
Gilbert et al., "Sieve analysis: methods for assessing from vaccine trial data how vaccine efficacy varies with genotypic and phenotypic pathogen variation," J Clinical Epidemiology 54:68-85, 2001.
Good et al., "Antisense PNA Effects in Escherichia coli are limited by the outer-membrane LPS layer," Microbiology 149(Pt 10):2665-2670, 2000.
Good et al., "Bactericidal antisense effects of peptide-PNA conjugates," Nature Biotechnology 19(4):360-364, Apr. 2001.
Good et al., "Inhibition of translation and bacterial growth by peptide nucleic acid targeted to ribosomal RNA," Proc. Natl. Acad. Sci. USA 95(5):2073-2076, 1998.
Greenberg et al., "Antisense Phosphorodiamidate Morpholino Oligmers Targeted to an Essential Gene Inhibit Burkholderia cepacia Complex," The Journal of Infectious Diseases 201(12):1822-1830, Jun. 2010.
Hale et al., "Recruitment of ZipA to the Septal Ring of Escherichia coli is Dependent on FtsZ and Independent of FtsA," Journal of Bacteriology 181(1):167-176, Jan. 1999.
Hunt et al., "Identification of Burkholderia cenocepacia Genes Required for Bacterial Survival In Vivo," Infection and Immunity 72(7):4010-4022, 2004.
International Search Report (US), dated Aug. 17, 2006, for PCT/US05/023553, 6 pages.
Iversen et al., "Antisense Antiviral Compound and Method for Treating ssRNA Viral Infection," Office Action, dated Oct. 19, 2010, U.S. Appl. No. 11/432,031, 25 pages.
Iversen et al., "Splice-Region Antisense Composition and Method," Office Action, dated Apr. 23, 2010, U.S. Appl. No. 11/433,214, 17 pages.
Jackowski et al., "Ratio of active to inactive forms of acyl carrier protein in Escherichia coli," J. Biol. Chem. 258(24):15186-15191, 1983.
Jackson et al., "Escherichia coli O157:H7 diarrhoea associated with well water and infected cattle on an Ontario farm," Epidemiol Infect 120(1):17-20, 1998.
Knudsen et al., "Antisense properties of duplex- and triplex-forming PNAs," Nucleic Acids Res 24(3):494-500, 1996.
Lutkenhaus et al., "Bacterial Cell Division and the Z Ring," Annu. Rev. Biochem. 66:93-116, 1997.
Mellbye et al., "Variation in Amino Acid Composition of Antisense Peptide-Phosphorodiamidate Escherichia coli In Vitro and In Vivo," Antimicrobial Agents and Chemotherapy 53(2):525-530, Feb. 2009.
Mitev et al., "Inhibition of Intracellular Growth of Salmonella enterica Serovar Typhimurium in Tissue Culture by Antisense Peptide-Phosphorodiamidate Morpholino Oligomer," Antimicrobial Agents and Chemotherapy 53(9):3700-3704, 2009.
Nekhotiaeva et al., "Inhibition of Staphylococcus aureus Gene Expression and Growth Using Antisense Peptide Nucleic Acids," Molecular Therapy 10(4):652-659, 2004.
Nielsen, "Peptide nucleic acids as antibacterial agents via the antisense principle," Exp. Opin. Invest. Drugs 10(2):331-341, 2001.
Nielsen, "Peptide nucleic acids: on the road to new gene therapeutic drugs," Pharmacol. Toxicol. 86(1):3-7, 2000.
Nielsen et al., "Sequence-selective recognition of DNA by strand displacement with a thymine-substituted polyamide," Science 254(5037):1497-1500, 1991.
Nikaido, "Transport across the bacterial outer membrane," J Bioenerg Biomembr 25(6):581-589, 1993.
Petersen et al., "Synthesis of thymidine dimers containing piperazine in the internucleoside linkage and their incorporation into oligodeoxynucleotides," Tetrahedron 51:2145-2154, 1995.
Polacco et al., "A mutant of Escherichia coli conditionally defective in the synthesis of holo-[acyl carrier protein]," J. Biol. Chem. 256(11):5750-5754, 1981.
Rahman et al., "Antibacterial Activity and Inhibition of Protein Synthesis in Escherichia coli by Antisense DNA Analogs," Antisense Research and Development 1(4):319-327, 1991.
Summerton, Peptide Nucleic Acids, Morpholinos, and Related Antisense Biomolecules, Landes Bioscience/Eurekah.com and Kluwer Academic/Plenum Publishers, ed. C.G Janson and M.J. During, 2006, Chapter 6, "Morpholinos and PNAs Compared," pp. 89-113.
Tan et al., "Peptide Nucleic Acid Antisense Oligomer as a Therapeutic Strategy against Bacterial Infection: Proof of Principle Using Mouse Intraperitoneal Infection," Antimicrobial Agents and Chemotherapy 49(8):3203-3207, Aug. 2005.
Ex Parte Thumm, 132 USPQ 66, 1961, 3 pages.
Tilley et al., "Gene-Specific Effects of Antisense Phosphorodiamidate Morpholino Oligomer-Peptide Conjugates on Escherichia coli and Salmonella enterica Serovar Typhimurium in Pure Culture and in Tissue Culture," Antimicrobial Agents and Chemotherapy 50(8):2789-2796, Aug. 2006.
Tilley et al., "Antisense peptide-phosphorodiamidate morpholino oligomer conjugate: dose-response in mice infected with Escherichia coli," Journal of Antimicrobial Chemotherapy 59:66-73, 2007.
Wang et al., "Assessment of the utilization of the antisense RNA strategy to Identify essential genes in heterologous bacteria," FEMS Microbiology Letters 220(2):171-176, 2003.
Weller et al., "Oligonucleotide Analogs Having Cationic Intersubunit Linkages," Office Action, dated Aug. 18, 2010, U.S. Appl. No. 11/801,885, 6 pages.
Weller et al., "Oligonucleotide Analogs Having Cationic Intersubunit Linkages," Advisory Action, dated Oct. 28, 2010, 11/801,885, 6 pages.
Wiersinga, "Beyond Antibiotics: New Horizons in Treating Burkholderia Species Infections," The Journal of Infectious Diseases 201(12), Jun. 2010, 2 pages.
Youngblood et al., "Stability of Cell-Penetrating Peptide—Morpholino Oligomer Conjugates in Human Serum and in Cells," Bioconjugate Chem. 18:50-60, 2007.
Zhang et al., "Polar Allele Duplication for Transcriptional Analysis of Consecutive Essential Genes: Application to a Cluster of Escherichia coli Fatty Acid Biosynthetic Genes," Journal of Bacteriology 178(12):3614-3620, Jun. 1996.
Zollinger et al., "Meningococcal vaccines—present and future," Transactions of Royal Soc of Tropical Medicine and Hygiene 85(Supp. 1):37-43, 1991.
Kang et al., "Stacking Interactions of ApA Analogues with Modified Backbones," Biopolymers 32:1351-1363, 1992.
Wang et al., "Synthesis of Antisense Phosphothioate Oligodeoxynucleotides of Dengue Fever Virus and their Anti-Viral Activity," Progress of Biochemistry and Biophysics 24(1), 12 pages, 1997.
Wang et al., "Specific Inhibition of Coxsackievirus B3 Translation and Replication by Phosphorothioate Antisense Oligodeoxynucleotides," Antimicrobial Agents and Chemotherapy 45(4):1043-1052, 2001.
Zuker, "Mfold web server for nucleic acid folding and hybridization prediction," Nucleic Acids Research 31(13):3406-3415, 2003.
Agrawal et al., "Oligodeoxynucleoside phosphoramidates and phosphorothioates as inhibitors of human immunodeficiency virus," Proc. Natl. Acad. Sci. USA 85:7079-7083, 1988.
Agrawal et al., "Site-specific excision from RNA by RNase H and mixed-phosphate-backbone oligodeoxynucleotides," Proc. Natl. Acad. Sci. USA 87:1401-1405, 1990.
Akhtar et al., "Interactions of antisense DNA oligonucleotide analogs with phospholipid membranes (liposomes)," Nucleic Acids Research 19(20)5551-5559, 1991.
Anderson et al., "Inhibition of Human Cytomegalovirus Immediate-Early Gene Expression by an Antisense Oligonucleotide Complementary to Immediate-Early RNA," Antimicrobial Agents and Chemotherapy 40(9):2004-2011, Sep. 1996.

(56) References Cited

OTHER PUBLICATIONS

Anderson et al., "Distribution of Equilibrative, Nitrobenzylthioinosine-Sensitive Nucleoside Transporters (ENT1) in Brain," *Journal of Neurochemistry* 73(2):867-873, 1999.
Arya et al., "Triple-helix formation of DNA oligomers with methylthiourea-linked nucleosides (DNmt): A kinetic and thermodynamic analysis," *Proc. Natl. Acad. Sci. USA* 96:4384-4389, Apr. 1999.
Bailey et al., "Cationic oligonucleotides can mediate specific inhibition of gene expression in Xenopus oocytes," *Nucleic Acids Research* 26(21):4860-4867, 1998.
Banerjee et al., "Interaction of picornavirus 2C polypeptide with the viral negative-strand RNA," *Journal of General Virology* 82:2621-2627, 2001.
Banerjee et al., "Interaction of Poliovirus-Encoded 2C/2BC Polypeptides with the 3' Terminus Negative-Strand Cloverleaf Requires an Intact Stem-Loop b," *Virology* 280:41-51, 2001.
Banerjee et al., "Poliovirus-Encoded 2C Polypeptide Specifically Binds to the 3'-Terminal Sequences of Viral Negative-Strand RNA," *Journal of Virology* 71(12):9570-9578, 1997.
Banerjee et al., "Specific Interaction of Hepatitis C Virus Protease/Helicase NS3 with the 3'-Terminal Sequences of Viral Positive- and Negative-Strand RNA," *Journal of Virology* 75(4):1708-1721, 2001.
Barawkar et al., "Synthesis, biophysical properties, and nuclease resistance properties of mixed backbone oligodeoxynucleotides containing cationic internucleoside guanidinium linkages: Deoxynucleic guanidine/DNA chimeras," *Proc. Natl. Acad. Sci. USA* 95:11047-11052, Sep. 1998.
Basler et al., "The Ebola virus VP35 protein functions as a type I IFN antagonist," *PNAS* 97(22):12289-12294, Oct. 24, 2000.
Blommers et al., "An approach to the structure determination of nucleic acid analogues hybridized to Rna. Nmr studies of a duplex between 2'-OMe RNA and an oligonucleotide containing a single amide backbone modification," *Nucleic Acids Research* 22(20):4187-4194, 1994.
Bonham et al., "An assessment of the antisense properties of RNase H-competent and steric-blocking oligomers," *Nucleic Acids Research* 23(7):1197-1203, 1995.
Borio et al., "Hemorrhagic Fever Viruses as Biological Weapons: Medical and Public Health Management," *JAMA* 287(18):2391-2405, May 8, 2002.
Borriello et al., "Differential Expression of Alternate Mb7-2 Transcripts," The *Journal of Immunology* 155(12):5490-5497, 1995.
Boudvillain et al., "Transplatin-Modified Oligo(2'-O-methyl ribonucleotide)s: A New Tool for Selective Modulation of Gene Expression," *Biochemistry* 36(10):2925-2931, 1997.
Branch, "A good antisense molecule is hard to find," *TIBS* 23:45-50, 1998.
Brasey et al., "The Leader of Human Immunodeficiency Virus Type 1 Genomic RNA Harbors an Internal Ribosome Entry Segment That Is Active During the $G_2$/M Phase of the Cell Cycle," *Journal of Virology* 77(7):3939-3949, Apr. 2003.
Bray et al., "A Mouse Model for Evaluation of Prophylaxis and Therapy of Ebola Hemorrhagic Fever," *The Journal of Infectious Diseases* 178:651-661, 1998.
Burnett et al., "The Evolving Field of Biodefence: Therapeutic Developments and Diagnostics," *Natural Reviews|Drug Discovery* 4:281-297, Apr. 2005.
Chambers et al., "CTLA-4-Mediated Inhibition in Regulation of T Cell Responses: Mechanisms and Manipulation in Tumor Immunotherapy," *Annu. Rev. Immunol.* 19:565-594, 2001.
Chirila et al., "The use of Synthetic polymers for delivery of therapeutic antisense oligodeoxynucleotides," *Biomaterials* 23:321-342, 2002.
Clarke et al., "Organization and Expression of Calicivirus Genes," *Journal of Infectious Diseases* 181(Suppl 2):S309-S316, 2000.
Connolly et al., "Pathogenesis of Experimental Ebola Virus Infection in Guinea Pigs," *The Journal of Infectious Diseases* 179(Suppl 1):S203-S217, 1999.

Corey et al., "Morpholino antisense oligonucleotides: tools for investigating vertebrate development," *Genome Biology* 2(5):reviews 1015.1-1015.3, Apr. 26, 2001.
Cross et al., "Solution Structure of an RNA•DMA Hybrid Duplex Containing a 3'-Thioformacetal Linker and an RNA A-Tract," *Biochemistry* 36(14):4096-4107, 1997.
Dagle et al., "Targeted elimination of zygotic messages in Xenopus laevis embryos by modified oligonucleotides possessing terminal cationic linkages," *Nucleic Acids Research* 28(10):2153-2157, 2000.
Deas et al., "Inhibition of Flavivirus Infections by Antisense Oligomers Specifically Suppressing Viral Translation and RNA Replication," *Journal of Virology* 79(8):4599-4609, Apr. 2005.
Dempcy et al., "Design and synthesis of deoxynucleic guanidine: A polycation analogue of DNA," *Proc. Natl. Acad. Sci. USA* 91:7864-7868, Aug. 1994.
Dempcy et al., "Design and synthesis of ribonucleic guanidine: A polycationic analog of RNA," *Proc. Natl. Acad. Sci. USA* 93:4326-4330, Apr. 1996.
Ding et al., "An oligodeoxyribonucleotide N3'→P5' phosphoramidate duplex forms an A-type helix in solution," *Nucleic Acids Research* 24(2):354-360, 1996.
Egholm et al., "PNA hybridizes to complementary oligonucleotides obeying the Watson-Crick hydrogen-bonding rules," *Nature* 365(6446):566-568, 1993.
Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications," *Biochemistry* 44:9045-9057, 2005.
Feldmann et al., "Classification, Structure, and Replication of Filoviruses," *Curr. Top. Microbiol. Immunol.* 235:1-21, 1999.
Feldmann et al., "EBOLA virus: from discovery to vaccine," *Nature Reviews* 3(8):677-685, Aug. 2003.
Feldmann et al., "Molecular biology and evolution of filoviruses," *Arch. Virol.* 7(Suppl.):81-100, 1993.
Feigner et al., "Lipofection: A highly efficient, lipid-mediated DNA-transfection procedure," *Proc. Natl. Acad. Sci. USA* 84(21):7413-7417, Nov. 1987.
Freier, "Methods of Selecting Sites in RNA for Antisense Targeting," Crooke (ed.), *Antisense Drug Technology: Principles, Strategies, and Applications*, CRC Press, New York, 1999, Chap. 5, pp. 107-118, 14 pages.
Gait et al., "Synthetic Analogues of Polynucleotides. Part XII. Synthesis of Thymidine Derivatives containing an Oxyacetamido- or an Oxyformamido-linkage instead of a Phosphodiester Group," *J. Chem. Soc.* 0(14):1684-1686, 1974.
Gee et al., "Assessment of High-Affinity Hybridization, RNase H Cleavage, and Covalent Linkage in Translation Arrest by Antisense Oligonucleotides," *Antisense & Nucleic Acid Drug Development* 8(2):103-111, 1998.
Geisbert et al., "Ebola virus: new insights into disease aetiopathology and possible therapeutic interventions," *Expert Reviews in Molecular Medicine* 6(20):1-24, Sep. 21, 2004.
Geisbert et al., "Treatment of Ebola virus infection with a recombinant inhibitor of factor VIIa/tissue factor: a study in rhesus monkeys," *The Lancet* 362(9400):1953-1958, Dec. 13, 2003.
Gong et al., "Molecular Mechanisms in Morpholino-DNA Surface Hybridization," *J. Am. Chem. Soc.* 132:9663-9671, 2010.
Green et al., "Antisense Oligonucleotides: An Evolving Technology for the Modulation of Gene Expression in Human Disease," *J. Am. Coll. Surg.* 191:93-105, 2000.
Gupta, "Molecular signaling in death receptor and mitochondrial pathways of apoptosis (Review)," *International Journal of Oncology* 22(1):15-20, 2003.
Hames et al. (eds.), "Nucleic acid hybridization: a practical approach," IRL Press, Oxford, England, pp. 107-108, 1985, 12 pages.
Hanecak et al., "Antisense Oligonucleotide Inhibition of Hepatitis C Virus Gene Expression in Transformed Hepatocytes," *Journal of Virology* 70(8):5203-5212, 1996.

(56) References Cited

OTHER PUBLICATIONS

He et al., "A Comparison of in Vitro and in Vivo Stability in Mice of Two Morpholino Duplexes Differing in Chain Length," *Bioconjugate Chem.* 14:1018-1023, 2003.
Holland, Morse (ed.), *Emerging Viruses*, Oxford University Press US, New York, 1993, Chap. 19, "Replication Error, Quasispecies Populations, and Extreme Evolution Rates of RNA Viruses," pp. 203-218, 18 pages.
Hudziak et al., "Resistance of Morpholino Phosphorodiamidate Oligomers to Enzymatic Degradation," *Antisense & Nucleic Acid Drug Development* 6:267-272, 1996.
Hudziak et al., "Antiproliferative Effects of Steric Blocking Phosphorodiamidate Morpholino Antisense Agents Directed against c-myc," *Antisense & Nucleic Acid Drug Dev.* 10:163-176, 2000.
Iversen, "Methods and Compositions for Manipulating Translation of Protein Isoforms From Alternative Initiation Start Sites," U.S. Appl. No. 14/232,858, filed Jan. 14, 2014, 166 pages.
Jaeger et al., "Improved predictions of secondary structures for RNA," *Proc. Natl. Sci. USA* 86:7706-7710, Oct. 1989.
Jahrling et al., "Evaluation of Immune Globulin and Recombinant Interferon-α2b for Treatment of Experimental Ebola Virus Infections," *The Journal of Infectious Diseases* 179(Suppl 1):S222-S234, 1999.
Jen et al., "Suppression of Gene Expression by Targeted Disruption of Messenger RNA: Available Options and Current Strategies," *Stem Cells* 18:307-319, 2000.
Johannes et al., "Identification of eukaryotic mRNAs that are translated at reduced cap binding complex eIF4F concentrations using a cDNA microarray." *PNAS* 96(23):13118-13123, Nov. 9, 1999.
Jubin et al., "Hepatitis C Virus Internal Ribosome Entry Site (IRES) Stem Loop IIId Contains a Phylogenetically Conserved GGG Triplet Essential for Translation and IRES Folding," *Journal of Virology* 74(22):10430-10437, Nov. 2000.
Kole et al., "Compound and Method for Treating Myotonic Dystrophy," U.S. Appl. No. 14/038,314, filed Sep. 26, 2013, 31 pages.
Lappalainen et al., "Cationic liposomes mediated delivery of antisense oligonucleotides targeted to HPV 16 E7 mRNA in CaSki cells," *Antiviral Research* 23:119-130, 1994.
Lesnikowski et al., "Octa(thymidine methanephosphonats) of partially defined stereochemistry: synthesis and effect of chirality at phosphorous on binding to pentadecadeoxyriboadenylic acid," *Nucleic Acids Research* 18(8):2109-2115, 1990.
Li et al., "Folate-Mediated Targeting of Antisense Oligodeoxynucleotides to Ovarian Cancer Cells," *Pharmaceutical Research* 15(10):1540-1546, 1998.
Linkletter et al., "Solid-phase synthesis of oligopurine deoxynucleic guanidine (DNG) and analysis of binding with DNA oligomers," *Nucleic Acids Research* 29(11):2370-2376, 2001.
Linkletter et al., "Solid-phase Synthesis of Positively Charged Deoxynucleic Guanidine (DNG) Modified Oligonucleotides Containing Neutral Urea Linkages: Effect of Charge Deletions on Binding and Fidelity," *Bioorganic & Medicinal Chemistry* 8:1893-1901, 2000.
Loke et al., "Characterization of Oligonucleotide transport into living cells," *Proc. Natl. Acad. Sci USA* 86(10):3474-3478, May 1989.
López de Quinto et al., "Involvement of the Aphthovirus RNA Region Located between the Two Functional AUGs in Start Codon Selection," *Virology* 255(2):324-336, 1999.
Lu et al., "Therapeutic dendritic-cell vaccine for chronic HIV-1 infection," *Nature Medicine* 10(12):1359-1365, Dec. 2004.
Manoharan, "Oligonucleotide Conjugates as Potential Antisense Drugs with Improved Uptake, Biodistribution, Targeted Delivery, and Mechanism of Action," *Antisense & Nucleic Acid Drug Development* 12:103-128, 2002.
Markoff, "5'-and 3'-Noncoding Regions in Flavivirus RNA," *Advances in Virus Research* 59:177-228, 2003.
Mertes et al., "Synthesis of Carbonate Analogs of Dinucleosides. 3'-Thymidinyl 5'-Thymidinyl Carbonate, 3'-Thymidinyl 5'-(5-Fluoro—2'-Deoxyuridinyl) Carbonate, and 3'-(5-Fluoro-2'-deoxyuridinyl) 5'-Thymidinyl Carbonate," *J. Med. Chem.* 12(1):154-157, 1969.
Meyer et al., "Arenaviruses: Geonomic RNAs, Transcription and Replication," *Curr. Top. Microbiol. Immunol.* 262:139-157, 2002.
Micklefield, "Backbone Modification of Nucleic Acids: Synthesis, Structure and Therapeutic Applications," *Current Medicinal Chemistry* 8:1157-1179, 2001.
Miyada et al., "[6] Oligonucleotide Hybridization Techniques," *Methods in Enzymology* 154:94-107, 1987.
Mohamadzadeh et al., "Dentritic cells: In the forefront of immunopathogenesis and vaccine development—A review," *Journal of Immune Based Therapies and Vaccines* 2(1):1-11, Jan. 13, 2004.
Morcos, "Achieving Efficient Delivery of Morpholino Oligos in Cultured Cells," *Genesis* 30:94-102, 2001.
Moulton et al., "Delivery of Antisense Phosphorodiamidate Morpholino Oligomers by Arginine-Rich Peptides", in *Proceedings of the 226th ACS National Meeting*, Abstract No. 75, American Chemical Society, New York, NY, Sep. 7-11, 2003, 2 pages.
Moulton et al., "Cellular Uptake of Antisense Morpholino Oligomers Conjugated to Arginine-Rich Peptides," *Bioconjugate Chemistry* 15:290-299, 2004.
Moulton et al., "Morpholinos and their peptide conjugates: Therapeutic promise and challenge for Duchenne muscular dystrophy," *Biochimica et Biophysica Acta* 1798:2296-2303, 2010.
Moulton et al., "HIV Tat Peptide Enhances Cellular Delivery of Antisense Morpholino 2Oligomers," *Antisense and Nucleic Acid Drug Development* 13(1):31-43, 2003.
Moulton et al., "Peptide-assisted delivery of steric-blocking antisense oligomers," *Current Opinion in Molecular Therapeutics* 5(2):123-132, 2003.
Nelson et al., "Arginine-Rich Peptide Conjugation to Morpholino Oligomers: Effects on Antisense Activity and Specificity," *Bioconjugate Chem.* 16:959-966, 2005.
Neuman et al., "Antisense Morpholino-Oligomers Directed Against the 5' End of the Genome Inhibit Coronavirus Proliferation and Growth," *Journal of Virology* 78(11):5891-5899, 2004.
Orabona et al., "CD28 induces immunostimulatory signals in dendritic cells via CD80 and CD86," *Nature Immunology* 5(11):1134-1142, Nov. 2004.
Orr et al., "Patent review: Therapeutic applications for antisense oligonucleotides 1999-2000," *Current Opinion in Molecular Therapeutics* 2(3):325-331, 2000.
O'Ryan et al., "Rotavirus, Enteric, Adenoviruses, Norwalk Virus, and Other Gastroenteritis Tract Viruses," Chapter 22, Specter et al., (Eds.) *Clinical Virology Manual*, Elsevier, New York,1992, pp. 361-396.
Palù et al. "In pursuit of new developments for gene theray of human diseases," *Journal of Biotechnology* 68:1-13, 1999.
Pardigon et al., "Cellular Proteins Bind to the 3' End of Sindbis Virus Minus-Strand RNA," *Journal of Virology* 66(2):1007-1015, 1992.
Pardigon et al., "Multiple Binding Sites for Cellular Proteins in the 3' End of Sindbis Alphavirus Minus-Sense RNA," *Journal of Virology* 67(8):5003-5011, 1993.
Pari et al., "Potent Antiviral Activity of an Antisense Oligonucleotide Complementary to the Intron-Exon Boundary of Human Cytomegalovirus Genes UL36 and UL37," *Antimicrobial Agents and Chemotherapy* 39(5):1157-1161, May 1995.
Partridge et al., "A Simple Method for Delivering Morpholino Antisense Oligos into the Cytoplasm of Cells," *Antisense & Nucleic Acid Drug Dev.* 6:169-175, 1996.
Paul, Aniko V., "Possible Unifying Mechanism of Picornavirus Genome Replication," B. L. Semler et al., (Eds.), *Molecular Biology of Picornaviruses*, ASM Press, Wastington, DC, 2002, Chap. 19, pp. 227-246.
Peters et al., "An Introduction to Ebola: The Virus and the Disease," *J. Infect. Dis.* 179(Suppl 1)ix-xvi, 1999.
Polyak et al., "5' Termini of Pichinde Arenavirus S RNAs and mRNAs Contain Nontemplated Nucleotides," *Journal of Virology* 69(5):3211-3215, 1995.

(56) References Cited

OTHER PUBLICATIONS

Raviprakash et al., "Inhibition of Dengue Virus by Novel, Modified Antisense Oligonucleotides," *Journal of Virology* 69(1):69-74, 1995.
Roehl et al., "Poliovirus Infection Enhances the Formation of Two Ribonucleoprotein Complexes at the 3' End of Viral Negative-Strand RNA," *Journal of Virology* 69(5):2954-2961, 1995.
Roehl et al., "Processing of a Cellular Polypeptide by 3CD Proteinase is Required for Poliovirus Ribonucleoprotein Complex Formation," *Journal of Virology* 71(1):578-585, 1997.
Rothbard et al., "Arginine-Rich Molecular Transporters for Drug Delivery: Role of Backbone Spacing in Cellular Uptake," *J. Med. Chem.* 45:3612-3618, 2002.
Salomon et al., "Complexities of CD28/B7: CTLA-4 Costimulatory Pathwaysin Autoimmunity and Transplantation," *Annu. Rev. Immunol.* 19:225-252, 2001.
Sanchez et al., "Sequence analysis of the Ebola virus genome: organization, genetic elements, and comparison with the genome of Marburg virus," *Virus Research* 29:215-240, 1993.
Sankar et al., "Antisense oligonucleotide inhibition of encephalomyocarditis virus RNA translation," *Eur. J. Biochem.* 184:39-45, 1989.
Sazani et al., "Systemically delivered antisense oligomers upregulate gene expression in mouse tissues," *Nature Biotechnology* 20:1228-1233, Dec. 2002.
Siprashvili et al., "Gene Transfer via Reversible Plasmid Condensation with Cysteine-Flanked, Internally Spaced Arginine-Rich Peptides," *Human Gene Therapy* 14:1225-1233, 2003.
Smith et al., "Calicivirus Emergence from Ocean Reservoirs: Zoonotic and Interspecies Movements," *Emerging Infectious Diseases* 4(1):13-20, 1998.
Smith et al., "Antisense treatment of Caliciviridae: An emerging disease agent of animals and humans," *Current Opinion in Molecular Therapeutics* 4(2):177-184, 2002.
Smith et al., "Secondary structure and hybridization accessibility of the hepatitis C virus negative strand RNA 5'-terminus," *Journal of Viral Hepatitis* 11:115-123, 2004.
Stein et al., "A Specificity Comparison of Four Antisense Types: Morpholino, 2'-O-Methyl RNA, DNA, and Phosphorothioate DNA," *Antisense & Nucleic Acid Drug Development* 7:151-157, 1997.
Stein et al., "Inhibition of Vesivirus Infections in Mammalian Tissue Culture with Antisense Morpholino Oligomers," *Antisense & Nucleic Acid Drug Development* 11:317-325, 2001.
Stein et al., "Antisense Antiviral Agent and Method for Treating ssRNA Viral Infection," Office Action dated Feb. 17, 2010, for Corresponding U.S. Appl. No. 11/431,968, 19 pages.
Summerton et al., "Morpholino and Phosphorothioate Antisense Oligomers Compared in Cell-Free and In-Cell Systems," *Antisense & Nucleic Acid Drug Development* 7:63-70, 1997.
Summerton et al., "Morpholino Antisense Oligomers: Design, Preparation, and Properties," *Antisense & Nucleic Acid Drug Development* 7(3):187-195, 1997.
Summerton, "Morpholino antisense oligomers: the case for an RNase H-independent structural type," *Biochimica et Biophysica Acta* 1489: 141-158, 1999.
Taylor et al., "Antisense oligonucleotides: a systematic high-throughput approach to target validation and gene function determination," *DDT* 4(12):562-567, 1999.
Thiel et al., "Infectious RNA transcribed in vitro from a cDNA the human coronavirus genome cloned in vaccinia virus," *Journal of General Virology* 82:1273-1281, 2001.
Toulmé et al., "Targeting RNA structures by antisense oligonucleotides," *Biochimie* 78:663-673, 1996.
Uhlmann et al., "Antisense Oligonucleotides: A New Therapeutic Principle," *Chemical Reviews* 90(4):544-584, Jun. 1990, 42 pages.

Van der Merwe et al., "Molecular Interactions Mediating T Cell Antigen Recognition," *Annu. Rev. Immunol.* 21:659-684, 2003.
Vijayakrishnan et al., "An Autoimmune Disease-Associated CTLA-4 Splice Variant Lacking the B7 Binding Domain Signals Negatively in T Cells," *Immunity* 20(5):563-575, 2004.
Wages, Jr. et al., "Affinity Purification of RNA: Sequence-Specific Capture by Nonionic Morpholino Probes," *BioTechniques* 23:1116-1121, 1997.
Warfield et al., "Role of Natural Killer Cells in Innate Protection Against Lethal Ebola Virus Infection," *The Journal of Experimental Medicine* 200(2):169-179, 2004.
Warfield et al., "Gene-Specific Countermeasures against Ebola Virus Based on Antisense Phosphorodiamidate Morpholino Oligomers," *PLoS Pathogens* 2(1):5-13, 2006.
Wasem et al., "Sensitizing antigen-specific $CD8^+$ T cells for accelerated suicide causes immune incompetence," *The Journal of Clinical Investigation* 111(8):1191-1199, Apr. 2003.
Wei et al., "Human immunodeficiency virus type-1 reverse transcription can be inhibited in vitro by oligonucleotides that target both natural and synthetic tRNA primers," *Nucleic Acids Research* 28(15):3065-3074, 2000.
Wender et al., "The design, synthesis, and evaluation of molecules that enable or enhance cellular uptake: Peptoid molecular transporters," *PNAS* 97(24):13003-13008, Nov. 21, 2000.
Williams et al., "Cationic lipids reduce time and dose of c-myc antisense oligodeoxynucleotides required to specifically inhibit Burkitt's lymphoma cell growth," *Leukemia* 10:1980-1989, 1996.
Wilson et al., "Naturally Occurring Dicistronic Cricket Paralysis Virus RNA Is Regulated by Two Internal Ribosome Entry Sites," *Molecular and Cellular Biology* 20(14):4990-4999, Jul. 2000.
Wu et al., "Receptor-mediated in Vitro Gene Transformation by a Soluble DNA Carrier System," *The Journal of Biological Chemistry* 262(10):4429-4432, Apr. 5, 1987.
Wu et al., "Specific Inhibition of Hepatitis B Viral Gene Expression in Vitro by Targeted Antisense Oligonucleotides," *The Journal of Biological Chemistry* 267(18):12436-124-39, 1992.
Xu et al., "Viral haemorrhagic disease of rabbits in the People's Republic of China: epidemiology and virus characterisation," *Rev. sci. tech. Off int. Epiz.* 10(2):393-408, 1991.
Yakubov et al., "Mechanism of oligonucleotide uptake by cells: Involvement of specific receptors?," *Proc. Natl. Acad. Sci. USA* 86(17):6454-6458, 1989.
Zhang et al., "Antisense Oligonucleotide Inhibition of Hepatitis C Virus (HCV) Gene Expression in Livers of Mice Infected with an HCV-Vaccinia Virus Recombinant," *Antimicrobial Agents and Chemotherapy* 43(2):347-353, 1999.
Zhang et al, "RNA interference in mammalian cells by siRNAs modified with morpholino nucleoside analogues," *Bioorganic & Medicinal Chemistry*, 17:2441-2446, 2009.
Gong et al., "Molecular Mechanisms in Morpholino-DNA Surface Hybridization," Journal of the American Chemical Society, 132(28): 9663-9671, 2010.
He et al., "A Comparison of in Vitro and in Vivo Stability in Mice of Two Morpholino Duplexes Differing in Chain Length," Bioconjugate Chemistry, 14(5):1018-1023, 2003.
Morcos, "Achieving Efficient Delivery of Morpholino Oligos in Culture Cells," Genesis, 30: 94-102, 2001.
Nelson et al., "Agrinine-Rich Peptide Conjugation to Morpholino Oligomers: Effects on Antisense Activity and Specificity," Bioconjugate Chemistry, 16(4): 959-966, 2005.
Stein et al., "A Specificity Comparison of Four Antisense Types: Morpholino, 2'-O-Methyl RNA, DNA, and Phosphorothioate DNA," Antisense & Nucleic Acid Drug Development, 7: 151-157, 1997.
Zhang et al., "RNA interference in mammalian cells by siRNAs modified with morpholino nucleoside analogues," Bioorganic & Medicinal Chemistry, 17: 2441-2446, 2009.

\* cited by examiner

DSRNA MOLECULES COMPRISING OLIGONUCLEOTIDE ANALOGS HAVING MODIFIED INTERSUBUNIT LINKAGES AND/OR TERMINAL GROUPS

CROSS-REFERENCE TO RELATED APPLICATION

This application claims the benefit of the filing date of U.S. Provisional Application 61/380,105, filed on Sep. 3, 2010, the entire contents of which is incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing 120178_489USPC_SEQUENCE_LISTING.txt. The text file is 4 KB, was created on Feb. 27, 2013, and is being submitted electronically via EFS-Web.

FIELD OF THE INVENTION

The present invention relates generally to double stranded RNA (dsRNA) molecules comprising oligonucleotide analogs, and more particularly to dsRNA molecules comprising one or more morpholino subunits having modified intersubunit linkages and/or terminal groups.

BACKGROUND OF THE INVENTION

Oligonucleotide compounds have important therapeutic applications in medicine. For example, certain oligonucleotides can be used to silence genes that are associated with particular diseases. Gene-silencing prevents formation of a protein by inhibiting translation. Importantly, gene-silencing agents represent a promising alternative to traditional small, organic compounds that inhibit the function of a protein linked to a disease.

dsRNA directs the sequence-specific degradation of mRNA through a process known as RNA interference (RNAi). RNAi is an evolutionarily conserved gene silencing mechanism, originally discovered in studies of the nematode *Caenorhabditis elegans* (Lee et al, Cell 75:843 (1993); Reinhart et al., Nature 403:901 (2000)). It is triggered by introducing dsRNA into cells expressing the appropriate molecular machinery, which then degrades the corresponding endogenous mRNA. The mechanism of RNAi involves conversion of dsRNA into short RNAs that direct ribonucleases to homologous mRNA targets (summarized, Ruvkun, Science 2294:797 (2001)). This process is related to normal defense mechanisms against viruses and the mobilization of transposons, and occurs in a wide variety of organisms, including mammals and other vertebrates.

The use of recombinantly produced dsRNA molecules or chemically synthesized oligonucleotides of the same or similar nature thus enables the targeting of specific mRNAs for silencing in mammalian cells. For example, small interfering RNA (siRNA) molecules are dsRNA molecules that exploit the RNAi mechanism within cells by targeting specific mRNAs of interest for degradation. As such, these dsRNA molecules represent promising agents for a variety of diagnostic and therapeutic purposes. For example, siRNA compounds can be used to identify the function of genes. In addition, siRNA compounds offer enormous potential as a new type of pharmaceutical agent which acts by silencing disease-causing genes. siRNA therapeutic agents for the treatment of many diseases including central-nervous-system diseases, inflammatory diseases, metabolic disorders, oncology, infectious diseases, and ocular disease, are under active development.

Despite the recent advances in siRNA technology, the need exists for siRNA molecules having improved pharmacologic properties. Requirements for successful implementation of siRNA therapeutic molecules, which are generally designed to target disease-causing genes to prevent the production of their encoded proteins, include (a) stability in vivo, (b) sufficient membrane permeability and cellular uptake, and (c) a good balance of binding affinity and sequence specificity. Many oligonucleotide analogs have been developed in which the phosphodiester linkages of native DNA are replaced by other linkages that are more resistant to nuclease degradation (see e.g. Barawkar and Bruice 1998; Linkletter, Szabo et al. 2001; Micklefield 2001). In addition, oligonucleotides have been modified by conjugation with other molecules, including peptides, in order to enhance cellular uptake (e.g., Moulton, Nelson et al. 2004; Nelson, Stein et al. 2005).

Nevertheless, there remains a need for modified dsRNA structures with improved performance, particularly in the area of stability and specificity, without compromising sequence selectivity. The present invention satisfies this need and offers other related advantages.

BRIEF SUMMARY OF THE INVENTION

Embodiments of the present invention include double-stranded ribonucleic acid (dsRNA) molecules for inhibiting the expression of a target gene in a cell, wherein said dsRNA comprises at least two sequences that are complementary to each other and wherein a sense strand comprises a first sequence and an antisense strand comprises a second sequence comprising a region of complementarity which is substantially complementary to at least a part of a target gene mRNA, wherein said region of complementarity is less than about 30 nucleotides in length, wherein one or both of the sense and antisense strands comprise an oligomer backbone having at least one morpholino subunit joined by intersubunit linkages, wherein each morpholino subunit supports a base-pairing moiety, and wherein the intersubunit linkages comprise a structure selected from the group consisting of (A) and (B) below:

(A). an intersubunit linkage comprising the following structure (A-I):

where

W is S or O, $X = NR^1R^2$ or $OR^6$, $Y = O$ or $NR^7$, and each said linkage is selected from:
(a) uncharged linkage (a), where each of $R^1$, $R^2$, $R^6$ and $R^7$ is independently selected from hydrogen and lower alkyl;
(b1) cationic linkage (b1), where $X=NR^1R^2$ and $Y=O$, and $NR^1R^2$ represents an optionally substituted piperazino group, such that $R^1R^2=$—CHRCHRN($R^3$)($R^4$)CHRCHR—, where each R is independently H or $CH_3$, $R^4$ is H, $CH_3$ or an electron pair, and $R^3$ is selected from H, lower alkyl, $C(=NH)NH_2$, Z-L-NHC($=NH$)$NH_2$, and $[C(O)CHR'NH]_mH$, where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;

(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy)alkyl; and (b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl;

and at least one said linkage is selected from cationic linkages (b1), (b2), and (b3); and (B). an intersubunit linkage comprising the following structure (B-I):

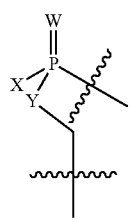
(B-I)

where each of the intersubunit linkages (I) are selected from:
(a) linkage (a) wherein:
W is S or O;
X is —$N(CH_3)_2$; and
Y is O, and
(b) linkage (b) wherein:
W is S or O;
X is $NR^1R^2$ or $OR^3$; and
Y is O or $NR^4$,
wherein $R^1$ is hydrogen or optionally substituted $C_2$-$C_{12}$ alkyl, each of $R^2$, $R^3$ and $R^4$ is independently hydrogen or optionally $C_1$-$C_{12}$ alkyl, and wherein each of $R^1$, $R^2$, $R^3$ and $R^4$ may join with another of $R^1$, $R^2$, $R^3$ or $R^4$ to form an optionally substituted 5, 6 or 7-membered heterocycle comprising one or more N, O or S atoms or combinations thereof, and wherein at least one of the intersubunit linkages comprises linkage (b).

In some embodiments, said morpholino subunits have the structure:

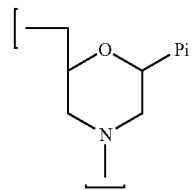
(i)

where Pi is a base-pairing moiety, and said linkages connect the nitrogen atom of (i) to the 5' carbon of an adjacent subunit.

Certain embodiments include a dsRNA molecule wherein all of the cationic linkages in the oligomer are of the same type. In certain embodiments, all of the cationic linkages in the oligomer are of type (b1). In some embodiments, all of the cationic linkages in the oligomer are of type (b2). In other embodiments, all of the cationic linkages in the oligomer are of type (b3).

In certain embodiments, 5% to 50% of the linkages in the oligomer are cationic linkages. In other embodiments, 10% to 35% of the linkages in the oligomer are cationic linkages.

Some embodiments include a dsRNA molecule wherein each of $R^1$ and $R^2$, in linkages of type (a), is methyl. In certain embodiments, said oligomer includes at least two consecutive linkages of type (a).

Certain embodiments include a dsRNA molecule having a length of about 10 to 30 base pairs. Specific embodiments include a molecule having a length of about 15 to 25 base pairs.

Certain embodiments include a dsRNA molecule wherein said cationic linkages are of type (b1), where each R is H, $R^4$ is H, $CH_3$, or an electron pair, and $R^3$ is selected from H, $CH_3$, $C(=NH)NH_2$, and C(O)-L-NHC($=NH$)$NH_2$. In particular embodiments, said cationic linkages are of type (b1), where each R is H, $R^4$ is an electron pair, and $R^3$ is selected from $C(=NH)NH_2$ and C(O)-L-NHC($=NH$)$NH_2$. In some embodiments, $R^3$ is C(O)-L-NHC($=NH$)$NH_2$, and L is a hydrocarbon. In certain embodiments, L has the structure —$(CH_2)_n$—, where n is 1 to 12. In some embodiments, n is 1 to 6.

Embodiments also include a dsRNA molecule wherein said cationic linkages are of type (b1), where each R is H, and each of $R^3$ and $R^4$ is independently H or $CH_3$. In specific embodiments, each of $R^3$ and $R^4$ is H.

Certain embodiments include a dsRNA molecule wherein said cationic linkages are of type (b2), where L is a linker up to 12 atoms in length having bonds selected from alkyl and alkylamino. In particular embodiments, said oligomer contains no linkages of type (b1) in which each of R, $R^3$ and $R^4$ is H.

Also included are dsRNA molecules further comprising, conjugated to a terminus of the oligomer, a peptide transport moiety, comprising 6 to 16 amino acids and composed of subsequences selected from the group consisting of (X'Y'X'), (X'Y'), (X'Z'), and (X'Z'Z'),
where
(a) each X' subunit independently represents arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral linear amino acid —C(O)—(CHR)$_n$—NH—, where n is 1 to 7 and each R is independently H or methyl; and (c) each Z' subunit independently represents an α-amino acid having a neutral aralkyl side chain.

In certain embodiments, the peptide comprises a sequence consisting of at least two repeats of a single subsequence selected from (X'Y'X'), (X'Y'), (X'Z'), and (X'Z'Z'). In certain embodiments, the peptide comprises a sequence consisting of at least three repeats of a single subsequence selected from (X'Y'X'), (X'Y'), (X'Z'), and (X'Z'Z'). In particular embodiments, the peptide comprises a sequence represented by one of (X'Y'X')$_p$, (X'Y')$_m$, and (X'Z'Z')$_p$, where p is 2 to 5 and m is 2 to 8. In certain embodiments, for each X', the side chain moiety is guanidyl. In certain embodiments, each Y' is —CO—(CH$_2$)$_n$—NH—, where n is 1 to 7. In some embodiments, n is selected from 2 and 5, such that Y' is selected from a β-alanine subunit and a 6-aminohexanoic acid subunit. In specific embodiments, each Z' is phenylalanine. In some embodiments, the conjugated peptide is linked to a terminus of the oligomer via a linker Ahx-B, where Ahx is a 6-aminohexanoic acid subunit and B is a β-alanine subunit.

Certain embodiments include a dsRNA molecule wherein the morpholino subunits have the following structure (i):

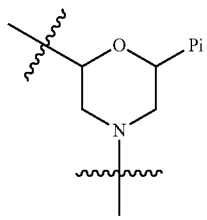

(i)

where each of Pi is the same or different and independently a base-pairing moiety, and the intersubunit linkages connect the nitrogen atom of (i) to the 5' carbon of an adjacent subunit. In certain embodiments, X is —NR$^1$R$^2$ and linkage (b) has the following structure (II):

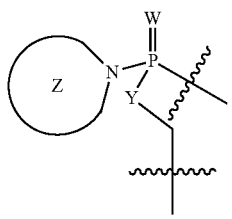

(B-II)

wherein Z represents a 5, 6 or 7 membered optionally substituted heterocycle comprising one or more N, O or S atoms or combinations thereof. In certain embodiments, W and Y are each O.

In particular embodiments, the linkage (b) has one of the following structures (III), (IV), (V) or (VI):

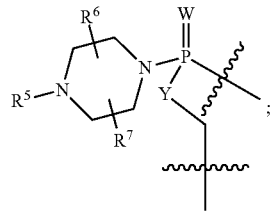

(B-III)

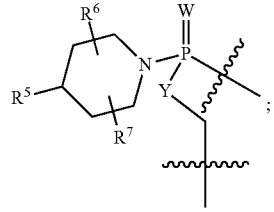

(B-IV)

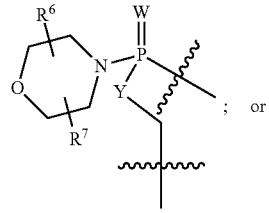

(B-V)

; or

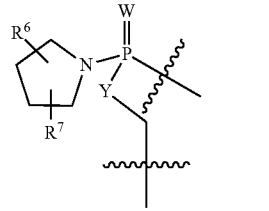

(B-VI)

wherein R$^5$, R$^6$ and R$^7$ are each independently optionally substituted C$_1$-C$_{12}$ alkyl, (—NR$^8$R$^9$), —C(=O)R$^8$—, optionally substituted aryl, optionally substituted heteroaryl, optionally substituted heterocycle, —SR$^8$, or C$_1$-C$_{12}$ alkoxy, wherein each of R$^8$ and R$^9$ are independently optionally substituted C$_1$-C$_{12}$ alkyl, —NR$^8$R$^9$, —C(=O)R$^8$—, optionally substituted aryl, optionally substituted heteroaryl, optionally substituted heterocycle, —SR$^8$, or C$_1$-C$_{12}$ alkoxy. In some embodiments, W and Y are each O.

In specific embodiments, X is OR$^3$ and Y is NR$^4$ and linkage (b) has the following structure (VII):

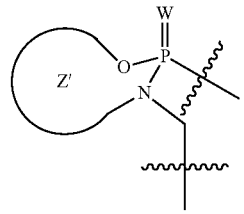

(B-VII)

wherein Z' represents a 5, 6 or 7 membered optionally substituted heterocycle comprising one or more N, O or S atoms or combinations thereof.

In some embodiments, linkage (b) has the following structure (VIII):

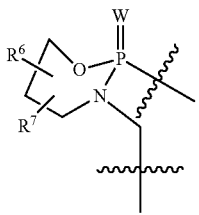

(B-VIII)

wherein $R^6$ and $R^7$ are each independently optionally substituted $C_1$-$C_{12}$ alkyl, —$NR^8R^9$, —C(=O)$R^8$—, optionally substituted aryl, optionally substituted heteroaryl, optionally substituted heterocycle, —$SR^8$, or $C_1$-$C_{12}$ alkoxy, wherein each of $R^8$ and $R^9$ are independently optionally substituted $C_1$-$C_{12}$ alkyl, —$NR^8R^9$, oxo —C(=O)$R^8$—, optionally substituted aryl, optionally substituted heteroaryl, optionally substituted heterocycle, —$SR^8$, or $C_1$-$C_{12}$ alkoxy. In certain embodiments, W is O.

In certain embodiments, linkage (b) is:

(b1) linkage (b1), wherein X=4-aminopiperidin-1-yl;
(b2) linkage (b2), wherein X=N-methyl-N-hexylamino;
(b3) linkage (b3), wherein X=4-N-(N-ibu-Cys)piperazin-1-yl;
(b4) linkage (b4), wherein X=4-N-(3,4,5-trimethoxybenzoyl)piperazin-1-yl;
(b5) linkage (b5), wherein X=4-N-pyrrolidinylpiperidin-1-yl;
(b6) linkage (b6), wherein X=4-N-(3-tetrazoylbenzoyl)piperazin-1-yl;
(b7) linkage (b7), wherein X=4-N-succinamidopiperazin-1-yl;
(b8) linkage (b8), wherein X=4-N-mercaptoacetylpiperazin-1-yl;
(b9) linkage (b9), wherein X=morpholino-4-yl;
(b10) linkage (b10), wherein X=S-2-methoxymethylpyrrolindin-1-yl;
(b11) linkage (b11), wherein X=R-2-methoxymethylpyrrolindin-1-yl;
(b12) linkage (b12), wherein X and Y may be taken together to form an optionally substituted heterocycle ring of 5, 6 or 7 members comprising one or more N, O or S atoms or combinations thereof;
(b13) linkage (b13), wherein X=4-trimethylaminopiperidin-1-yl; or
(b14) linkage (b14), wherein X=4-guanidinylpiperidin-1-yl.

Embodiments also include a dsRNA molecule wherein Pi is thymine and the intersubunit linkages and morpholino subunits connected thereto have one of the following structures (c1) through (C14):

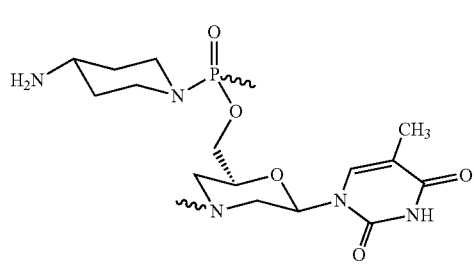

PMO$^{apn}$ (c1)

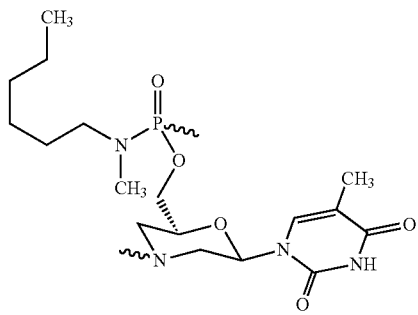

PMO$^{hex}$ (c2)

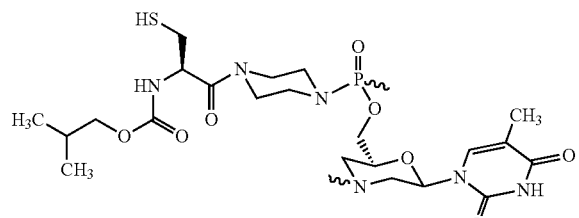

PMO$^{SH}$ (c3)

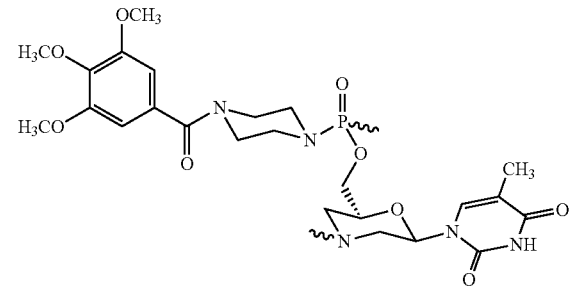

PMO$^{tri}$ (c4)

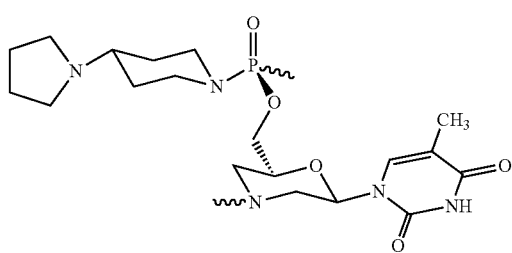

PMOpyr (c5)

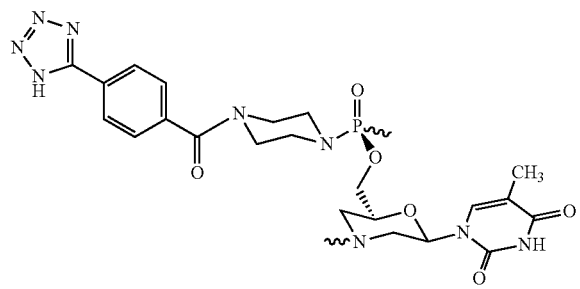

PMO$^{tet}$ (c6)

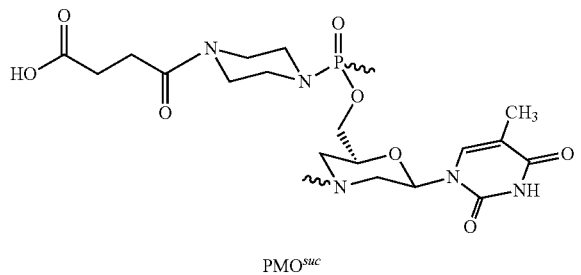
PMO<sup>suc</sup> (c7)

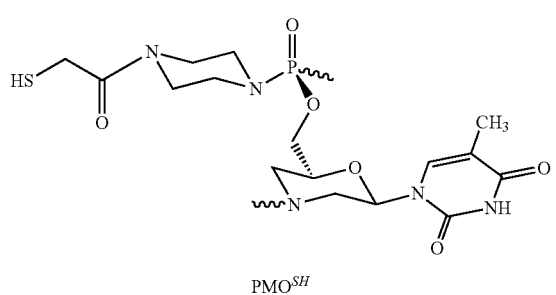
PMO<sup>SH</sup> (c8)

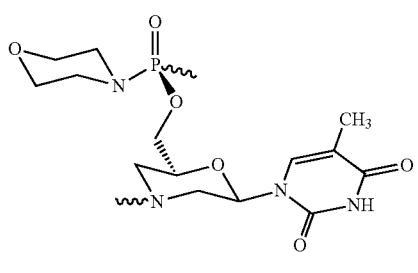
(c9)

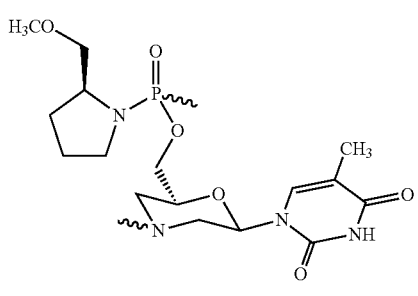
PMO<sup>Spro</sup> (c10)

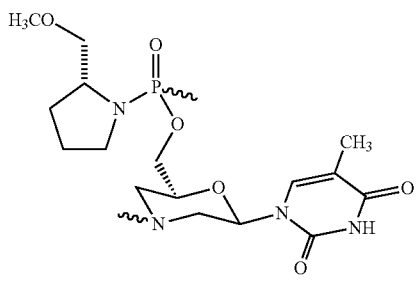
PMO<sup>Rpro</sup> (c11)

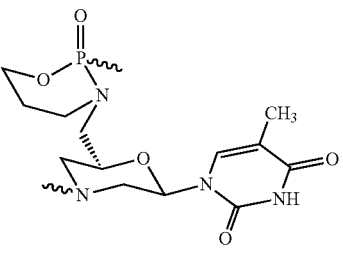
PMO<sup>cp</sup> (c12)

In certain embodiments, at least 5% of the intersubunit linkages are linkages (b1) thru (b14). In other embodiments, 10% to 50% of the intersubunit linkages are linkages (b1) thru (b14). In particular embodiments, all of the modified linkages (i.e. linkages (b1) thru (b14)) have the same structure.

In certain embodiments, at least one of the sense and antisense strands comprise a 5' terminal residue and/or a 3' terminal residue, wherein the 5' terminal residue and/or the 3' terminal residue has a terminal structure as set out in the following structure (C-I):

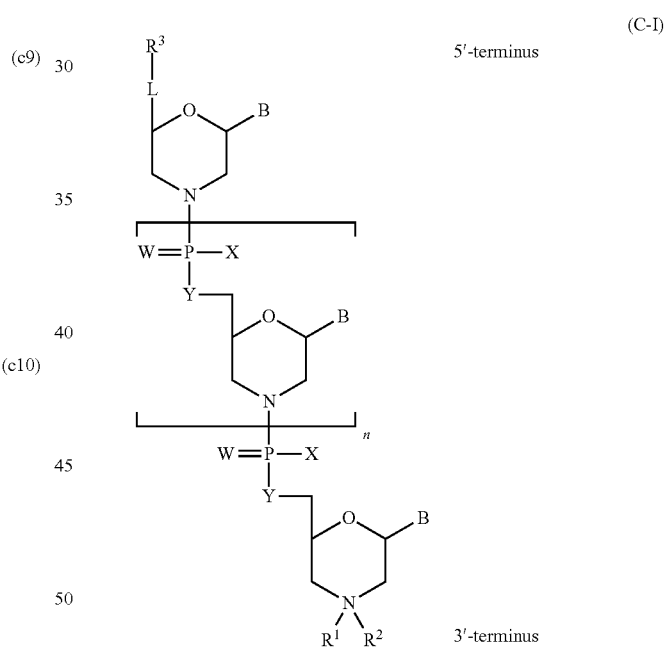
(C-I)

wherein, independently at each occurrence:
$R^1$ is absent, H or $C_1$-$C_6$ alkyl;
$R^2$ and $R^3$ are absent, H, a cell-penetrating peptide or $R^4$;
$R^4$ is optionally substituted $C_1$-$C_{30}$ alkyl, optionally substituted $C_3$-$C_8$ cycloalkyl, optionally substituted aryl, optionally substituted $C_1$-$C_{30}$ aralkyl, optionally substituted $C_1$-$C_{30}$ alkylcarbonyl, optionally substituted $C_3$-$C_8$ cycloalkylcarbonyl, optionally substituted $C_3$-$C_8$ cycloalkylalkylcarbonyl, optionally substituted $C_1$-$C_{30}$ arylcarbonyl, optionally substituted $C_1$-$C_{30}$ aralkylcarbonyl, optionally substituted $C_1$-$C_{30}$ alkyloxycarbonyl, optionally substituted $C_3$-$C_8$ cycloalkyloxycarbonyl, optionally substituted $C_1$-$C_{30}$ aryloxycarbonyl or optionally substituted $C_1$-$C_{30}$ aralkyloxycarbonyl;

W is S or O;
X is NR$^5$R$^6$ or OR$^7$;
Y is O or NR$^8$,
B is a base-pairing moiety;
L is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate and phosphodiester; and
n is an integer of 0 or greater; and
wherein each of R$^5$, R$^6$, R$^7$ and R$^8$ is independently hydrogen or optionally substituted C$_1$-C$_{12}$ alkyl, and wherein each of R$^5$, R$^6$, R$^7$ and R$^8$ may join with another of R$^5$, R$^6$, R$^7$ or R$^8$ to form an optionally substituted 5, 6 or 7-membered heterocycle comprising one or more N, O or S atoms or combinations thereof; and wherein at least one of R$^2$ or R$^3$ is R$^4$, and provided that both of R$^1$ and R$^2$ are not absent. In certain embodiments, R$^4$ is optionally substituted C$_1$-C$_{30}$ arylcarbonyl.

In certain embodiments, R$^4$ has one of the following structures (C-II) or (C-III):

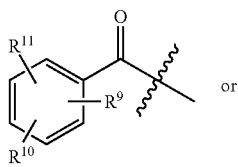

(C-II)

or

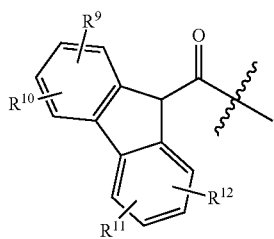

(C-III)

wherein R$^9$, R$^{10}$, R$^{11}$ and R$^{12}$ are each independently hydrogen, halo, optionally substituted C$_1$-C$_{30}$ alkyl, optionally substituted C$_1$-C$_{30}$ alkoxy, optionally substituted aryl, optionally substituted heteroaryl or optionally substituted heterocyclyl.

In specific embodiments, R$^4$ has one of the following structures (C-IV), (C-V), (C-VI) or (C-VII).

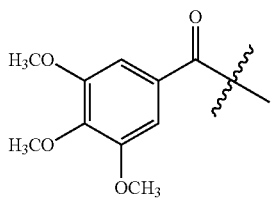

(C-IV)

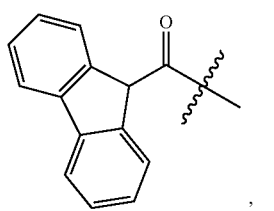

(C-V)

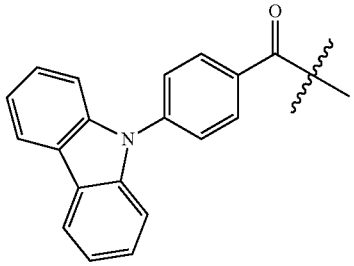

(C-VI)

, or

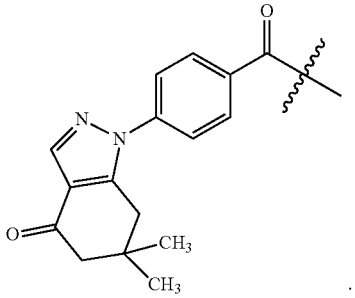

(C-VII)

In certain embodiments, R$^4$ is optionally substituted C$_1$-C$_{30}$ alkyl and wherein the optionally substituted C$_1$-C$_{30}$ alkyl comprises one or more double bonds.

In certain embodiments, R$^4$ has one of the following structures (C-VIII), (C-IX) or (C-X):

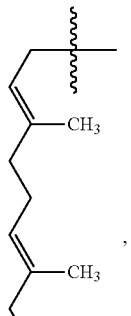

(C-VIII)

,

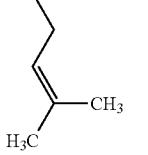
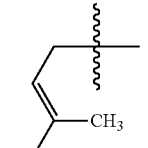
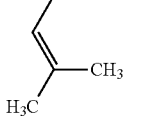

(C-IX)

or

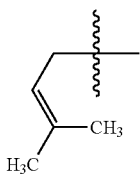

In some embodiments, $R^4$ is optionally substituted $C_1$-$C_{30}$ aralkylcarbonyl, and wherein the optionally substituted $C_1$-$C_{30}$ aralkylcarbonyl comprises one or more optionally substituted phenyl moieties.

In certain embodiments, $R^4$ has the following structure (C-XI):

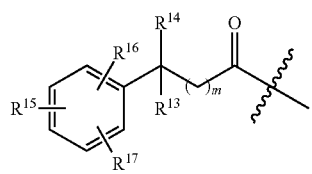

(C-XI)

wherein $R^{13}$, $R^{14}$, $R^{15}$, $R^{16}$ and $R^{17}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl and m is an integer from 0 to 6.

In particular embodiments, $R^4$ has one of the following structures (C-XII), (C-XIII), (C-XIV) or (C-XV):

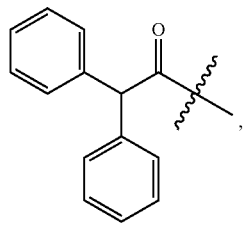

(C-XII)

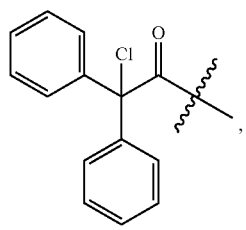

(C-XIII)

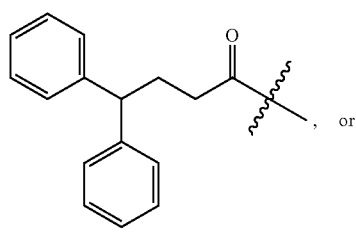

(C-XIV)

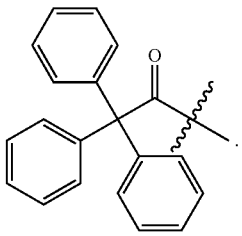

(C-XV)

In certain embodiments, $R^4$ is optionally substituted $C_1$-$C_{30}$ aralkyl, and wherein the optionally substituted $C_1$-$C_{30}$ aralkyl comprises one or more optionally substituted phenyl moieties.

In certain embodiments, $R^4$ has the following structure (C-XVI):

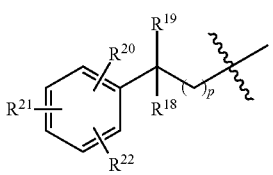

(C-XVI)

wherein $R^{18}$, $R^{19}$, $R^{20}$, $R^{21}$ and $R^{22}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl and p is an integer from 0 to 6.

In some embodiments, $R^4$ has the following structure (C-XVII):

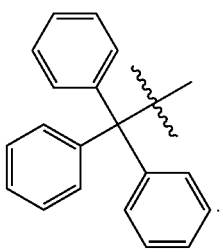

(C-XVII)

In certain embodiments, $R^4$ is optionally substituted $C_3$-$C_8$ cycloalkylcarbonyl, and wherein the optionally substituted $C_3$-$C_8$ cycloalkylcarbonyl comprises an optionally substituted cyclohexyl moiety.

In certain embodiments, $R^4$ has the following structure (C-XVIII):

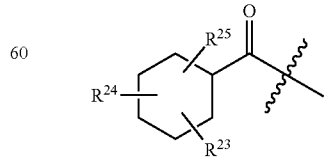

(C-XVIII)

wherein $R^{23}$, $R^{24}$ and $R^{25}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl.

In certain embodiments, $R^4$ has the following structure (C-XIX):

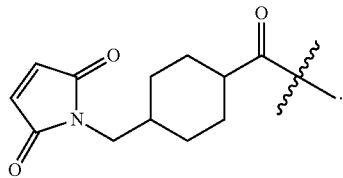

(C-XIX)

In specific embodiments, $R^4$ is optionally substituted $C_1$-$C_{30}$ alkylcarbonyl, and wherein the optionally substituted $C_1$-$C_{30}$ alkylcarbonyl comprises one or more sulfur atoms.

In certain embodiments, $R^4$ has the following structure (C-XX):

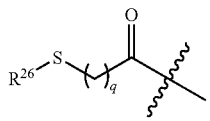

(C-XX)

wherein $R^{26}$ is hydrogen or —$SR^{27}$, wherein $R^{27}$ is hydrogen, optionally substituted $C_1$-$C_{30}$ alkyl, optionally substituted heterocyclyl, optionally substituted aryl or optionally substituted heteroaryl and q is an integer from 0 to 6.

In certain embodiments, $R^4$ has one of the following structures (C-XXI) or (C-XXII):

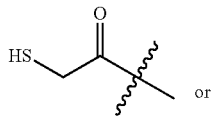

(C-XXI)

or

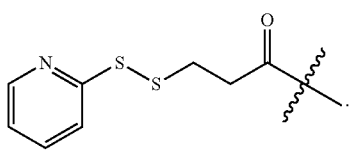

(C-XXII)

In certain embodiments, $R^4$ comprises one or more halo atoms. In particular embodiments, $R^4$ comprises a perfluoro $C_1$-$C_{30}$ alkyl, perfluoro $C_3$-$C_8$ cycloalkyl, perfluoro aryl, perfluoro $C_1$-$C_{30}$ aralkyl perfluoro $C_1$-$C_{30}$ alkylcarbonyl, perfluoro $C_3$-$C_8$ cycloalkylcarbonyl, perfluoro $C_3$-$C_8$ cycloalkylalkylcarbonyl, perfluoro $C_1$-$C_{30}$ arylcarbonyl, perfluoro $C_1$-$C_{30}$ aralkylcarbonyl, perfluoro $C_1$-$C_{30}$ alkyloxycarbonyl, perfluoro $C_3$-$C_8$ cycloalkyloxycarbonyl perfluoro $C_1$-$C_{30}$ aryloxycarbonyl or perfluoro $C_1$-$C_{30}$ aralkyloxycarbonyl.

In certain embodiments, $R^4$ is p-trifluoromethylphenyl, trifluoromethyltrityl, perfluoropentyl or pentafluorophenyl. In other embodiments, $R^2$ is absent and $R^3$ is $R^4$. In certain embodiments, $R^3$ is absent and $R^2$ is $R^4$. In some embodiments, $R^2$ and $R^3$ are each $R^4$. In certain embodiments, $R^2$ is a cell-penetrating peptide and $R^3$ is $R^4$. In certain embodiments, $R^3$ is a cell-penetrating peptide and $R^2$ is $R^4$. In certain embodiments, $R^1$ is methyl. In other embodiments, $R^1$ is absent.

In certain embodiments, L comprises phosphorodiamidate and piperazine bonds. In particular embodiments, L has the following structure (C-XXIII):

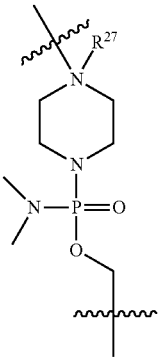

(C-XXIII)

wherein $R^{27}$ is absent, H or $C_1$-$C_6$ alkyl.

In certain embodiments, $R^{27}$ is absent. In other embodiments, $R^{27}$ is methyl.

In certain embodiments, at least one X is —$NR^5R^6$ and at least one of the intersubunit linkages has the following structure (C-XXIV):

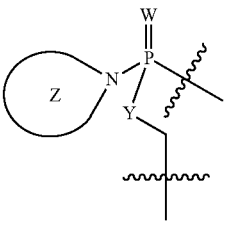

(C-XXIV)

wherein Z represents a 5, 6 or 7 membered optionally substituted heterocycle comprising one or more N, O or S atoms or combinations thereof. In certain embodiments, W and Y are each O.

In certain embodiments, at least one of the intersubunit linkages has one of the following structures (C-XXV), (C-XXVI), (C-XXVII) or (C-XXVIII):

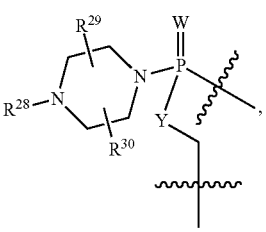

(C-XXV)

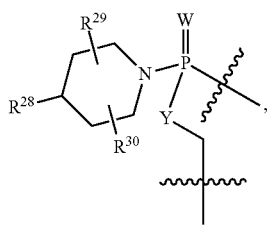
(C-XXVI)

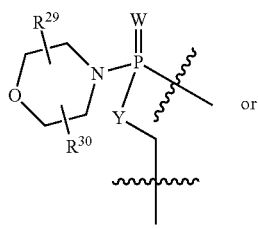
(C-XXVII) or

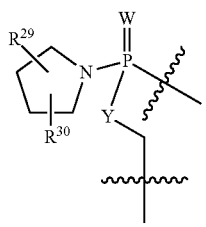
(C-XXVIII)

wherein $R^{28}$, $R^{29}$ and $R^{30}$ are each independently optionally substituted $C_1$-$C_{12}$ alkyl, (—$NR^{31}R^{32}$), —C(=O)$R^{31}$—, optionally substituted aryl, optionally substituted heteroaryl, optionally substituted heterocycle, —$SR^{31}$, or $C_1$-$C_{12}$ alkoxy, wherein each of $R^{31}$ and $R^{32}$ are independently optionally substituted $C_1$-$C_{12}$ alkyl, —$NR^{31}R^{32}$, —C(=O)$R^{31}$—, optionally substituted aryl, optionally substituted heteroaryl, optionally substituted heterocycle, —$SR^{31}$, or $C_1$-$C_{12}$ alkoxy. In certain embodiments, W and Y are each O.

In some embodiments, at least one X is $OR^7$ and at least one Y is $NR^8$ and at least one of the intersubunit linkages has the following structure (C-XXIX):

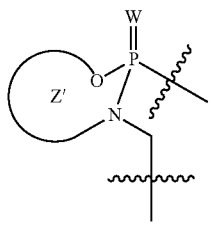
(C-XXIX)

wherein Z' represents a 5, 6 or 7 membered optionally substituted heterocycle comprising one or more N, O or S atoms or combinations thereof.

In certain embodiments, at least one of the intersubunit linkages has the following structure (C-XXX):

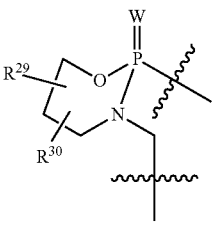
(C-XXX)

wherein $R^{29}$ and $R^{30}$ are each independently optionally substituted $C_1$-$C_{12}$ alkyl, —$NR^{31}R^{32}$, —C(=O)$R^{31}$—, optionally substituted aryl, optionally substituted heteroaryl, optionally substituted heterocycle, —$SR^{31}$, or $C_1$-$C_{12}$ alkoxy, wherein each of $R^{31}$ and $R^{32}$ are independently optionally substituted $C_1$-$C_{12}$ alkyl, —$NR^{31}R^{32}$, oxo —C(=O)$R^{31}$—, optionally substituted aryl, optionally substituted heteroaryl, optionally substituted heterocycle, —$SR^{31}$, or $C_1$-$C_{12}$ alkoxy. In particular embodiments, W is O.

In certain embodiments, at least one X is selected from dimethylamino, piperazyn-1-yl, 4-aminopiperidin-1-yl; N-methyl-N-hexylamino, 4-N-(N-ibu-Cys)piperazin-1-yl, 4-N-(3,4,5-trimethoxybenzoyl)piperazin-1-yl, 4-N-pyrrolidinylpiperidin-1-yl, 4-N-(3-tetrazoylbenzoyl)piperazin-1-yl, 4-N-succinamidopiperazin-1-yl, 4-N-mercaptoacetylpiperazin-1-yl, morpholino-4-yl, S-2-methoxymethylpyrrolindin-1-yl, R-2-methoxymethylpyrrolindin-1-yl, 4-trimethylaminopiperidin-1-yl, 4-guanidinylpiperidin-1-yl and structure (C-XXXI):

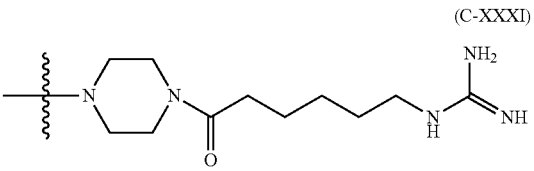 [SMILES: *N1CCN(C(=O)CCCCCNC(=N)N)CC1]
(C-XXXI)

In certain embodiments, X and Y may be taken together to form an optionally substituted heterocycle ring of 5, 6 or 7 members comprising one or more N, O or S atoms or combinations thereof. In some embodiments, at least one of the sense and antisense strands comprise 3' single stranded overhangs, wherein the single stranded overhangs comprise at least one morpholino subunit comprising an intersubunit linkage described herein. In particular embodiments, the sense strand comprises at least one morpholino subunit comprising an intersubunit linkage described herein. In certain embodiments, the sense strand comprises a plurality of morpholino subunits comprising intersubunit linkages described herein. In certain embodiments, at least about 50% of the sense strand comprises morpholino subunits comprising intersubunit linkages of the type described herein. In certain embodiments, at least one of the sense and antisense strands comprise 5' and/or 3' terminal residues, wherein the 5' and/or 3' terminal residues comprise a modified terminal group.

Also included are methods of inhibiting production of a protein comprising exposing a nucleic acid encoding the protein to a dsRNA molecule described herein.

DETAILED DESCRIPTION OF THE INVENTION

I. Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" refers to the —CN radical.

"Hydroxy" or "hydroxyl" refers to the —OH radical.

"Imino" refers to the =NH substituent.

"Guanidinyl" refers to the —NHC(=NH)$NH_2$ substituent.

"Amidinyl" refers to the —C(=NH)$NH_2$ substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to thirty carbon atoms ($C_1$-$C_{30}$ alkyl), one to twenty-five carbon atoms ($C_1$-$C_{25}$ alkyl), one to sixteen carbon atoms ($C_1$-$C_{16}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylamino" refers to a radical of the formula —$NHR_g$ or —$NR_gR_g$ where each $R_g$ is, independently, a cycloalkyl radical as defined above. Unless stated otherwise specifically in the specification, a cycloalkylamino group may be optionally substituted.

"Alkylcarbonyl", "cycloalkylcarbonyl", "cycloalklycarbonyl", cycloaklylalkylcarbonyl", "arylcarbonyl" or "aralkylcarbonyl" refers to the an oxo substituent having an alkyl, cycloalkyl, cycloalkylalkyl, aryl, or aralkyl substituent, respectively.

"Oxycarbonyl" refers to a radical of the formula —C(=O)OR$_i$ where R$_i$ is an alkyl, aryl, cycloalkyl or aralkyl radical as defined above.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —R$_b$R$_f$ where R$_b$ is an alkylene chain as defined above and R$_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, cycloalkylamino, carbonyls, oxycarbonyls, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, guanidines, amidines and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(═O)R$_g$, —C(═O)OR$_g$, —C(═O) NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, cycloalkylamino, oxycarbonyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "double-stranded RNA" or "dsRNA", as used herein, refers to a ribonucleic acid molecule having a duplex structure comprising two anti-parallel nucleic acid strands, wherein a first strand includes a region which is substantially complementary to a target sequence, and the second strand includes a region that is sufficiently complementary to the first strand such that the two strands hybridize. Once the antisense strand of a dsRNA molecule is designed to target a particular nucleic acid target, the sense strand of the dsRNA can then be designed and synthesized as the complement of the antisense strand and either strand can contain modifications or additions to either terminus. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs, typically from 1-5 nucleotides in length.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term "sense strand," as used herein, refers to the strand of a dsRNA that includes a region that is complementary to a region of the antisense strand.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary "morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in co-owned U.S. Pat. Nos. 5,698,685, 5,217,866, 5,142,047, 5,034,506, 5,166,315, 5,185,444, 5,521,063, 5,506,337 and pending applications U.S. Ser. Nos. 12/271,036, 12/271,040 and PCT publication number WO/2009/064471 all of which are incorporated herein by reference in their entirety.

"PMO+" refers to phosphorodiamidate morpholino oligomers comprising any number of (1-piperazino)phosphinylideneoxy and/or (1-(4-(ω-guanidino-alkanoyl))-piperazino)phosphinylideneoxy linkages that have been described previously (see e.g., PCT publication WO2008036127).

"PMO$^{X1}$" refers to phosphorodiamidate morpholino oligomers comprising the modified intersubunit linkages described in the co-owned and pending U.S. Patent Application No. 61/349,783.

"PMO$^{X2}$" refers to phosphorodiamidate morpholino oligomers comprising any of the modified terminal groups described in the co-owned and pending U.S. Patent Application No. 61/361,878.

A "phosphoramidate" group comprises phosphorus having three attached oxygen atoms and one attached nitrogen atom, while a "phosphorodiamidate" group comprises phosphorus having two attached oxygen atoms and two attached nitrogen atoms. Generally, in the uncharged or the modified intersubunit linkages of the oligomers described herein and co-pending U.S. Patent Application Ser. Nos. 61/349,783 and 11/801,885, one nitrogen is pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Modified linkage" refers to the resulting linkage when lipid, sulfhydryl, cation, and/or anion-containing groups are added to any of the atoms in the intersubunit linkage between two consecutive ring structures in the oligomer.

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

A "non-interfering" substituent is one that does not adversely affect the ability of an oligomer as described herein to bind to its intended target. Such substituents include, e.g., small and/or relatively non-polar groups such as methyl, ethyl, methoxy, ethoxy, or fluoro.

An oligomer "specifically hybridizes" to a target polynucleotide if the oligomer hybridizes to the target under physiological conditions, with a Tm greater than 37° C. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987).

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog or dsRNA that is complementary (meaning, in addition, substantially complementary) to the target gene mRNA sequence in the RNA genome. The entire sequence, or only a portion, of the analog compound may be complementary to the target sequence. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." In some instances, the oligonucleotide analog may have at most one mismatch with the target sequence out of 10 nucleotides, and preferably at most one mismatch out of 20. Alternatively, the oligomers employed have a targeting sequence having at least 90% sequence homology, and preferably at least 95% sequence homology, with the desired target gene mRNA sequences. For purposes of complementary binding to an RNA target, a guanine base may be complementary to either a cytosine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementarity of the oligomer to the target sequence, as well as with exact complementarity.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of agents across the cell membrane by a transport mechanism that requires binding of the agent to a transport protein, which then facilitates passage of the bound agent across the membrane.

The terms "modulating expression" and/or "dsRNA activity" refer to the ability of a dsRNA molecule described herein to either enhance or, more typically, reduce the expression of a given target protein, by interfering with the expression or translation of the mRNA encoding the target protein. In the case of reduced protein expression, an oligomer may contribute to the accelerated breakdown of the mRNA transcribed from that target gene.

An "amino acid subunit" is preferably an α-amino acid residue (—CO—CHR—NH—); it may also be a β- or other amino acid residue (e.g. —CO—CH$_2$CHR—NH—), where R is a side chain.

The term "naturally occurring amino acid" refers to an amino acid present in proteins found in nature. The term "non-natural amino acids" refers to those amino acids not present in proteins found in nature; examples include beta-alanine (β-Ala) and 6-aminohexanoic acid (Ahx).

An "effective amount" or "therapeutically effective amount" refers to an amount of dsRNA administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Double-Stranded Ribonucleic Acid (dsRNA) Molecules

The present invention relates generally to modified dsRNA molecules, as well as compositions and methods for inhibiting the expression of a target gene in a cell using such modified dsRNA molecules. The present invention also provides compositions and methods for treating diseases in organisms by targeting disease-associated genes using modified dsRNA molecules.

Various general structural features required for dsRNA activity have been defined and published, and any such features may be used in conjunction with the modified siRNA molecules described herein.

A dsRNA molecule is generally comprised of a ribonucleic acid molecule having a duplex structure comprising two anti-parallel nucleic acid strands, wherein a first strand includes a region which is substantially complementary to a target sequence, and the second strand includes a region that is sufficiently complementary to the first strand such that the two strands hybridize to form a duplex under suitable conditions. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA.

A dsRNA duplex structure is typically between about 15 and 30 base pairs, or between about 18 and 25 base pairs, or between about 19 and 24 base pairs in length. In certain instances, the dsRNA duplex structure is preferably between about 21 and 23 base pairs in length. Similarly, the region of complementarity to the target sequence is generally between about 15 and 30 base pairs, or between about 18 and 25 base pairs, or between about 19 and 24 base pairs, or between about 21 and 23 base pairs in length.

It will be understood that a dsRNA can contain one or more mismatches to the target sequence of interest. Typically, the dsRNA contains no more than 3 mismatches across the region of complementarity with the target sequence. Moreover, if the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity.

At least one end of a dsRNA molecule may have a single-stranded nucleotide overhang of, for example, 1 to 5 nucleotides. In one embodiment, the single-stranded overhang is located at the 3'-terminal end of the antisense strand or, alternatively, at the 3'-terminal end of the sense strand. The dsRNA may also have a blunt end, e.g., located at the 5'-end of the antisense strand. In another embodiment, the antisense strand of the dsRNA has a nucleotide overhang at the 3'-end, and the 5'-end is blunt.

In certain preferred embodiments of the invention, at least one, and as many as all, of the nucleotides present in the antisense strand of a dsRNA comprise morpholino subunits structures and/or terminal group modifications as described herein. In a more particular embodiment, at least about 20%, 30%, 40% or 50% of the nucleotides present in the antisense strand of a dsRNA comprise morpholino subunit structures and/or terminal group modifications as described herein.

In certain other preferred embodiments, at least one, and as many as all, of the nucleotides present in a single stranded overhang of a dsRNA molecules comprise morpholino subunits and/or terminal group modifications as described herein. In a more particular embodiment, at least 1, 2, 3, 4 or 5 nucleotides present in a single stranded overhang of a dsRNA molecule comprise morpholino subunits. In a further preferred embodiment, one or more 5' and/or 3' terminal residues present in a dsRNA molecule are modified with a terminal group modification as described herein.

dsRNA may be chemically modified to enhance stability or other properties. Indeed, numerous dsRNA modifications have been described and are well known in the art and it should be understood that essentially any of these modifications may be used in conjunction with a dsRNA molecules comprising morpholino subunits and/or terminal group modifications described herein.

The nucleic acids of the present invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to, 2' modifications, introduction of non-natural bases, covalent attachment to a ligand, replacement of phosphate linkages with thiophosphate linkages, and the like. The integrity of the duplex structure may be strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In certain embodiments, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, Biochem. (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups.

In certain embodiments, a chemical bond may be formed by means of one or several bonding groups, wherein such bonding groups are preferably poly-(oxyphosphinicooxy-1, 3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, Nat. Med. (1995) 1:1116-8). Thus, a 2'-hydroxyl group of the nucleotides on a dsRNA may be replaced by a chemical group, such as by a 2'-amino or a 2'-methyl group. Also, at least one nucleotide may be modified to form a locked nucleotide, if desired. Such a locked nucleotide contains a methylene bridge that connects the 2'-oxygen of ribose with the 4'-carbon of ribose. Oligonucleotides containing the locked nucleotide are described in Koshkin, A. A., et al., Tetrahedron (1998), 54:3607-3630) and Obika, S. et al., Tetrahedron Lett. (1998), 39:5401-5404). Introduction of a locked nucleotide into an oligonucleotide may improve the affinity for complementary sequences and increase the melting temperature by several degrees (Braasch, D. A. and D. R. Corey, Chem. Biol. (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, the ligand conjugated to the dsRNA may be a substrate for receptor-mediated endocytosis. These approaches have been used to facilitate cell permeation. For example, cholesterol has been conjugated to various antisense oligonucleotides resulting in compounds that are substantially more active compared to their non-conjugated analogs. See M. Manoharan Antisense & Nucleic Acid Drug Development 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. Pharm. Res. 1998, 15, 1540. Other illustrative ligands that may be conjugated to oligonucleotides include polyethylene glycols, carbohydrate clusters, cross-linking agents, porphyrin conjugates, and delivery peptides (such as the targeting peptides described herein).

In certain instances, conjugation of a cationic ligand to oligonucleotides may result in improved resistance to nucleases. Representative examples of cationic ligands are, for example, propylammonium and dimethylpropylammonium.

A ligand-conjugated dsRNA may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. Such ligand-nucleoside conjugates, optionally attached to a solid-support material, may be prepared via reaction of a selected serum-binding ligand with a linking moiety located on the 5' position of a nucleoside or oligonucleotide. In certain instances, a dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

dsRNA molecules may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Illustrative examples of particular modified oligonucleotides may be found, for example, in U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

III. Structural Features of dsRNA Molecules of the Present Invention

Certain structural features of the dsRNA molecules of the present invention are described in detail below. Of course, it will be understood that the present invention encompasses a wide variety of dsRNA structures that minimally contain one or more such structural features. More particularly, a dsRNA molecule of the present invention, in addition to including one or more structural features set out below, may further comprise any of a variety of additional structural modifications described herein and/or known in the art of dsRNA molecules.

A. dsRNA Molecules Comprising Modified Intersubunit Linkages (+PMO)

According to one aspect, the present invention provides a dsRNA molecule comprising at least in part an oligomer comprising a backbone of one or more morpholino ring structures joined by intersubunit linkages, where each such ring structure supports a base-pairing moiety, such that said oligomer can bind in a sequence-specific manner to a target nucleic acid, where the intersubunit linkages of the dsRNA molecule comprise the following structure (A-I):

(A-I)

where
W is S or O, and is preferably O,
$X = NR^1R^2$ or $OR^6$,
$Y = O$ or $NR^7$,
    and each said linkage in the oligomer is selected from:
    (a) uncharged linkage (a), where each of $R^1$, $R^2$, $R^6$ and $R^7$ is independently selected from hydrogen and lower alkyl;

(b1) cationic linkage (b1), where $X=NR^1R^2$ and $Y=O$, and $NR^1R^2$ represents an optionally substituted piperazino group, such that $R^1R^2$=—CHRCHRN($R^3$)($R^4$)CHRCHR—, where
each R is independently H or $CH_3$,
$R^4$ is H, $CH_3$, or an electron pair, and
$R^3$ is selected from H, lower alkyl, e.g. $CH_3$, C(=NH)$NH_2$, Z-L-NHC(=NH)$NH_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where $X=NR^1R^2$ and $Y=O$, $R^1$=H or $CH_3$, and $R^2$=$LNR^3R^4R^5$, where L, $R^3$, and $R^4$ are as defined above, and $R^5$ is H, lower alkyl, or lower (alkoxy)alkyl; and
(b3) cationic linkage (b3), where $Y=NR^7$ and $X=OR^6$, and $R^7$=$LNR^3R^4R^5$, where L, $R^3$, $R^4$ and $R^5$ are as defined above, and $R^6$ is H or lower alkyl;
and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 80%, 10% to 50%, or 10% to 35% of the linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g. $CH_3$, C(=NH)$NH_2$, and C(O)-L-NHC(=NH)$NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g. —$CH_2$—$CH_2$—), alkoxy (—C—O—), and alkylamino (e.g. —$CH_2$—NH—), with the proviso that the terminal atoms in L (e.g., those adjacent to carbonyl or nitrogen) are carbon atoms. Although branched linkages (e.g. —$CH_2$—$CHCH_3$—) are possible, the linker is preferably unbranched. In one embodiment, the linker is a hydrocarbon linker. Such a linker may have the structure —($CH_2$)$_n$—, where n is 1-12, preferably 2-8, and more preferably 2-6.

The morpholino subunits preferably have the structure:

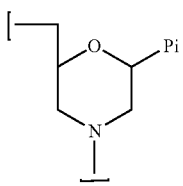

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

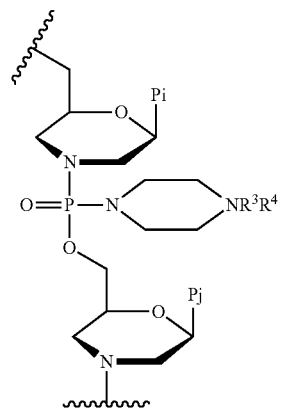

(b1)

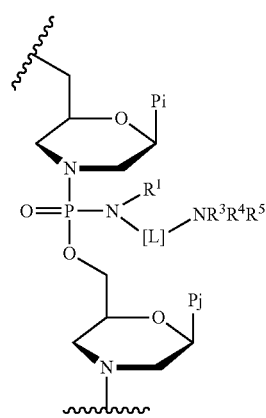

(b2)

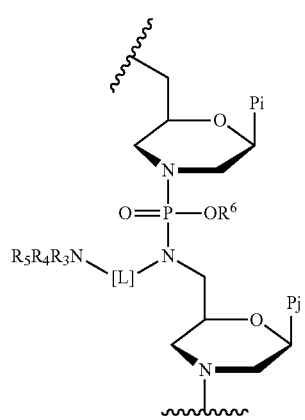

(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1") is referred to herein as a "Pip" linkage and (b1") is referred to herein as a "GuX" linkage:

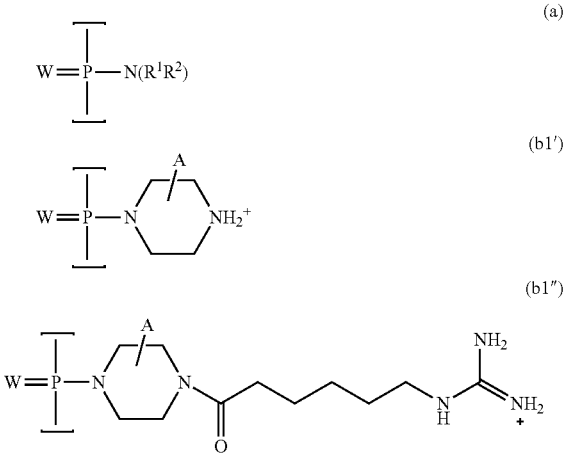

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 20% to 80%, 20% to 50%, or 20% to 30% of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5' nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 5, 10, 20, 30, 40, 50, 60, 70, 80 or 90 percent cationic linkages. In selected embodiments, about 10 to 80, 20 to 80, 20 to 60, 20 to 50, 20 to 40, or about 20 to 35 percent of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in dsRNA applications generally range in length from about 10 to about 40 subunits, more preferably about 15 to 25 subunits, per strand. For example, an oligomer of the invention having 19-20 subunits, may ideally have two to seven, e.g. four to six, or three to five, cationic linkages, and the remainder uncharged linkages. An oligomer having 14-15 subunits may ideally have two to five, e.g. 3 or 4, cationic linkages and the remainder uncharged linkages.

Each morpholino ring structure supports a base pairing moiety, to form a sequence of base pairing moieties which is typically designed to hybridize to a selected antisense target. The base pairing moiety may be a purine or pyrimidine found in native RNA or an analog, such as hypoxanthine (the base component of the nucleoside inosine) or 5-methyl cytosine.

As noted above, the substantially uncharged oligonucleotide may be modified, in accordance with an aspect of the invention, to include one or more charged linkages, e.g. up to about 1 per every 2-5 uncharged linkages, typically 3-5 per every 10 uncharged linkages. Optimal improvement in antisense activity is seen where up to about half of the backbone linkages are cationic. Some, but not maximum enhancement is typically seen with a small number e.g., 10-20% cationic linkages; where the number of cationic linkages exceeds 50-60%, the sequence specificity of the antisense binding to its target may be compromised or lost.

The enhancements seen with added cationic backbone charges may, in some case, be further enhanced by distributing the bulk of the charges close of the "center-region" backbone linkages of the dsRNA, e.g., in a 20mer oligonucleotide with 8 cationic backbone linkages, having 70%-100% of these charged linkages localized in the 10 centermost linkages.

The preparation of "PMO+" oligomers above are described in detail in, e.g., PCT publication WO2008036127, the content of which is incorporated herein by reference in its entirety.

B. dsRNA Molecules Comprising Modified Intersubunit Linkages (PMO-x)

According to one aspect, the present invention provides a dsRNA molecule comprising at least in part an oligomer comprising a backbone of one or more morpholino ring structures joined by intersubunit linkages, where each such ring structure supports a base-pairing moiety, such that said oligomer can bind in a sequence-specific manner to a target nucleic acid, where the intersubunit linkages of the dsRNA molecule comprise the following structure (B-I):

where each of the intersubunit linkages (I) are selected from:
  (a) linkage (a) wherein:
    W is S or O;
    X is $-N(CH_3)_2$; and
    Y is O, and (b) linkage (b) wherein:

W is S or O;

X is $NR^1R^2$ or $OR^3$; and

Y is O or $NR^4$, wherein $R^1$ is hydrogen or optionally substituted $C_2$-$C_{12}$ alkyl, each of $R^2$, $R^3$ and $R^4$ is independently hydrogen or optionally $C_1$-$C_{12}$ alkyl, and wherein each of $R^1$, $R^2$, $R^3$ and $R^4$ may join with another of $R^1$, $R^2$, $R^3$ or $R^4$ to form an optionally substituted 5, 6 or 7-membered heterocycle comprising one or more N, O or S atoms or combinations thereof, and wherein at least one of the intersubunit linkages comprises linkage (b).

In further embodiments, the morpholino subunits preferably have the following structure (i):

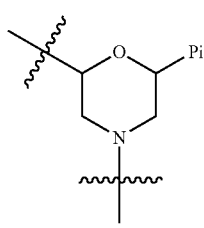

(i)

where each of Pi is the same or different and independently a base-pairing moiety, and the intersubunit linkages connect the nitrogen atom of (i) to the 5' carbon of an adjacent subunit.

In other further embodiments, X is $-NR^1R^2$ and linkage (b) has the following structure (II):

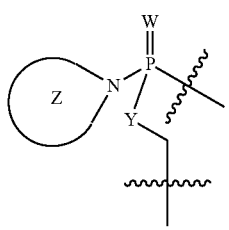

(B-II)

wherein Z represents a 5, 6 or 7 membered optionally substituted heterocycle comprising one or more N, O or S atoms or combinations thereof. For example, in some embodiments of the foregoing W and Y are each O.

In other further embodiments, linkage (b) has one of the following structures (B-III), (B-IV), (B-V) or (B-VI):

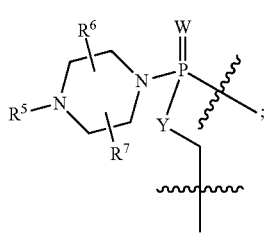

(B-III)

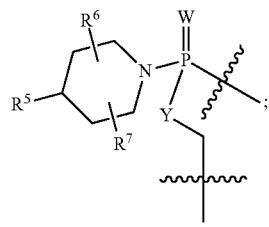

(B-IV)

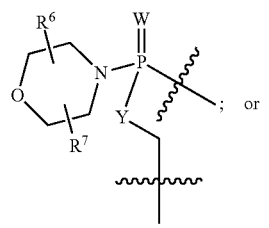

(B-V); or

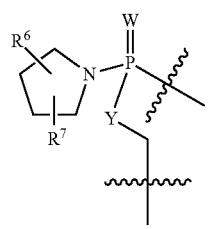

(B-VI)

wherein $R^5$, $R^6$ and $R^7$ are each independently optionally substituted $C_1$-$C_{12}$ alkyl, amino ($-NR^8R^9$), $-C(=O)R^8-$, optionally substituted aryl, optionally substituted heteroaryl, optionally substituted heterocycle, $-SR^8$, or $C_1$-$C_{12}$ alkoxy, wherein each of $R^8$ and $R^9$ are independently optionally substituted $C_1$-$C_{12}$ alkyl, $-NR^8R^9$, $-C(=O)R^8-$, optionally substituted aryl, optionally substituted heteroaryl, optionally substituted heterocycle, $-SR^8$, or $C_1$-$C_{12}$ alkoxy. For example, in some embodiments of the foregoing W and Y are each O.

In some further embodiments, X is $OR^3$ and Y is $NR^4$ and linkage (b) has the following structure (B-VII):

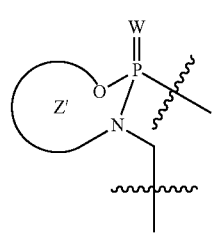

(B-VII)

wherein Z' represents a 5, 6 or 7 membered optionally substituted heterocycle comprising one or more N, O or S atoms or combinations thereof.

In other specific embodiments, linkage (b) has the following structure (B-VIII):

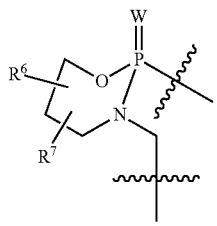

(B-VIII)

wherein $R^6$ and $R^7$ are each independently optionally substituted $C_1$-$C_{12}$ alkyl, —$NR^8R^9$, —$C(=O)R^8$—, optionally substituted aryl, optionally substituted heteroaryl, optionally substituted heterocycle, —$SR^8$, or $C_1$-$C_{12}$ alkoxy, wherein each of $R^8$ and $R^9$ are independently optionally substituted $C_1$-$C_{12}$ alkyl, —$NR^8R^9$, —$C(=O)R^8$—, optionally substituted aryl, optionally substituted heteroaryl, optionally substituted heterocycle, —$SR^8$, or $C_1$-$C_{12}$ alkoxy. For example, in some embodiments of the foregoing W is O.

In some specific embodiments, linkage (b) is:
- (b1) linkage (b1), wherein X=4-aminopiperidin-1-yl;
- (b2) linkage (b2), wherein X=N-methyl-N-hexylamino;
- (b3) linkage (b3), wherein X=4-N-(N-ibu-Cys)piperazin-1-yl;
- (b4) linkage (b4), wherein X=4-N-(3,4,5-trimethoxybenzoyl)piperazin-1-yl;
- (b5) linkage (b5), wherein X=4-N-pyrrolidinylpiperidin-1-yl;
- (b6) linkage (b6), wherein X=4-N-(3-tetrazoylbenzoyl)piperazin-1-yl;
- (b7) linkage (b7), wherein X=4-N-succinamidopiperazin-1-yl;
- (b8) linkage (b8), wherein X=4-N-mercaptoacetylpiperazin-1-yl;
- (b9) linkage (b9), wherein X=morpholino-4-yl;
- (b10) linkage (b10), wherein X=S-2-methoxymethylpyrrolindin-1-yl;
- (b11) linkage (b11), wherein X=R-2-methoxymethylpyrrolindin-1-yl;
- (b12) linkage (b12), wherein X and Y may be taken together to form an optionally substituted heterocycle ring of 5, 6 or 7 members comprising one or more N, O or S atoms or combinations thereof;
- (b13) linkage (b13), wherein X=4-trimethylaminopiperidin-1-yl; or
- (b14) linkage (b14), wherein X=4-guanidinylpiperidin-1-yl.

In other embodiments Pi is thymine, and the intersubunit linkages and morpholino subunits connected thereto have one of the following structures (c1) through (c14):

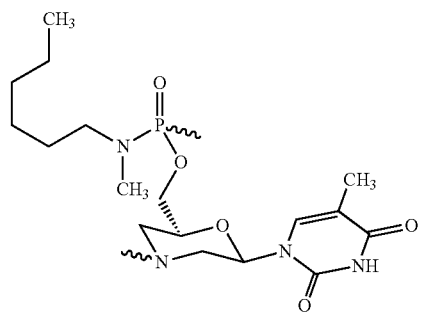

PMO$^{hex}$ (c2)

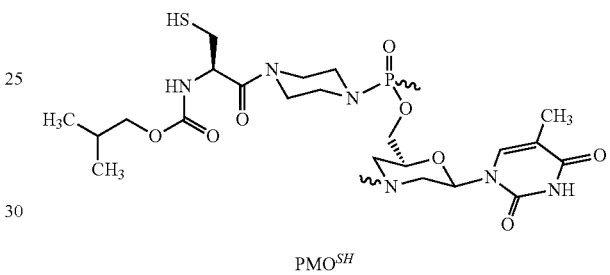

PMO$^{SH}$ (c3)

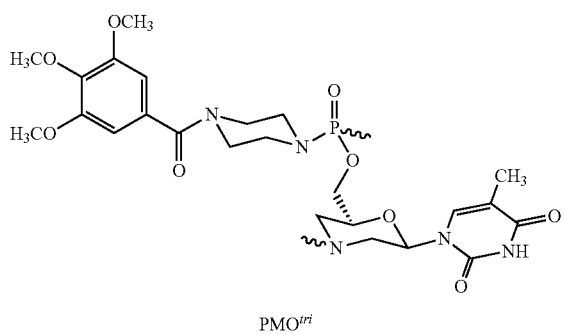

PMO$^{tri}$ (c4)

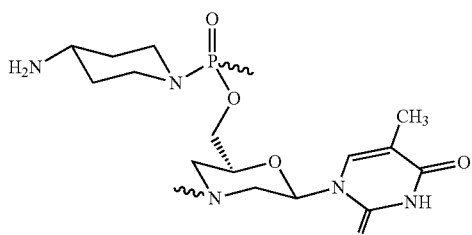

PMO$^{apn}$ (c1)

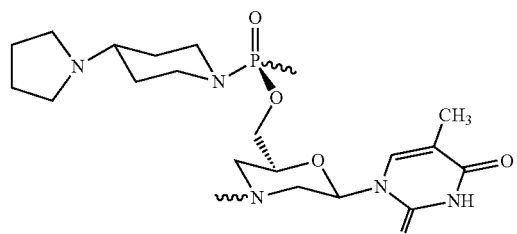

PMOpyr (c5)

(c6)
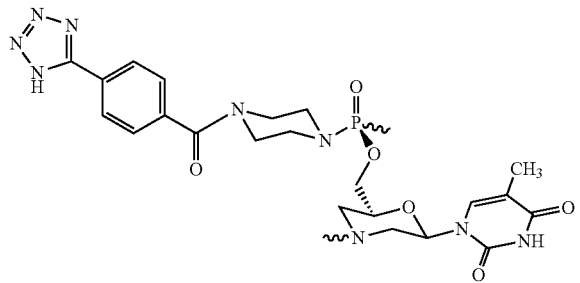
PMO$^{tet}$ (c7)
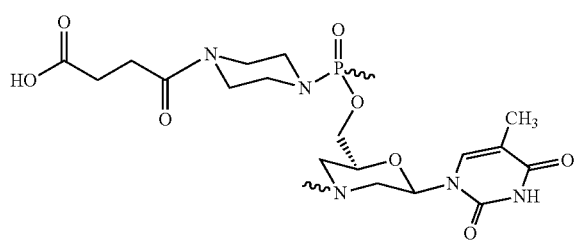
PMO$^{suc}$ (c8)
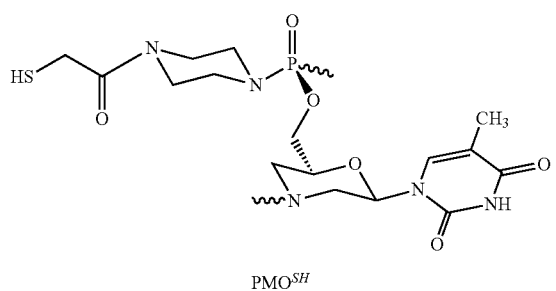
PMO$^{SH}$ (c9)
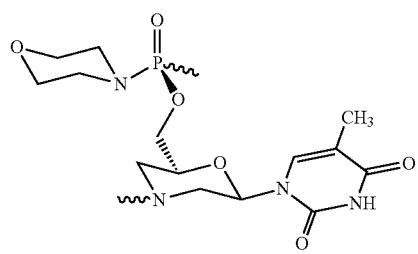

(c10)
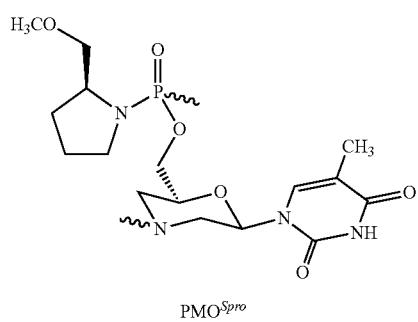
PMO$^{Spro}$ (c11)
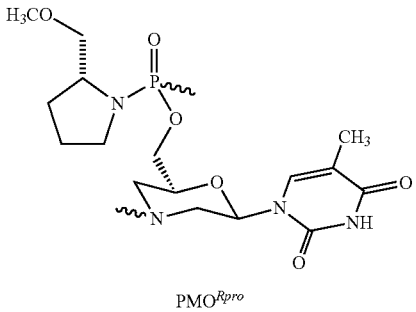
PMO$^{Rpro}$ (c12)
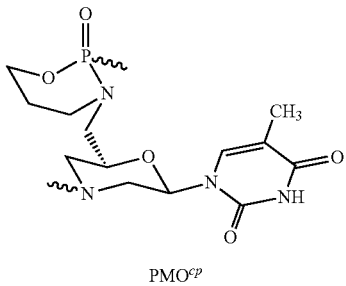
PMO$^{cp}$ In some other embodiments at least 5% of the intersubunit linkages are linkages (b1) thru (b14). In other embodiments, 10% to 50% of the intersubunit linkages are linkages (b1) thru (b14).

In some embodiments, all of the modified linkages (i.e. linkages (b1) thru (b14)) have the same structure.

The present disclosure also provides a method of inhibiting production of a protein comprising exposing a nucleic acid encoding the protein to a dsRNA molecules as disclosed herein.

In some embodiments, the oligomer comprises at least two consecutive unmodified linkages. In further embodiments, at least 5% of the linkages in the oligomer are modified linkages (i.e. type (b1) thru (b14); for example, 10% to 80%, 10% to 50%, or 10% to 35% of the linkages may be modified linkages.

In some embodiments, the morpholino subunits are linked by non-phosphorus-based intersubunit linkages, as described further below, where at least one linkage is modified with a pendant group as described above. In other embodiments, other oligonucleotide analog linkages which are uncharged in their unmodified state but which could also bear a pendant amine substituent are used. For example, in some embodiments the nitrogen atom in a carbamate, sulfonamide or sulfamide linkage (where phosphorus is replaced with carbon or sulfur, respectively) can be modified in a manner analogous to the 5'-nitrogen atom in structure (b1) above.

Oligomers having any number of modified linkages are provided, including uncharged linkages, fully cationic-linked oligomers, fully anionic linked oligomers, fully lipophillic linked oligomers and combinations thereof. In certain embodiments, the oligomers are partially charged or partially modified, having, for example, 5, 10, 20, 30, 40, 50, 60, 70, 80 or 90 percent modified linkages. In selected embodiments, about 10 to 80, 20 to 80, 20 to 60, 20 to 50, 20 to 40, or about 20 to 35 percent of the linkages are modified.

In one embodiment, the modified linkages are interspersed along the backbone. For example, in one embodiment, oligomers comprise at least two consecutive unmodified linkages; that is, in this embodiment the oligomer does not have a strictly alternating pattern along its entire length.

Also contemplated are oligomers comprising blocks of modified linkages and blocks of unmodified linkages; for example, a central block of unmodified linkages may be flanked by blocks of modified linkages, or vice versa. In one embodiment, the oligomer has approximately equal-length 5", 3" and center regions, and the percentage of modified linkages in the center region is greater than about 50%, preferably greater than about 70%. In some embodiments, the oligomers range in length from about 10 to about 40 subunits, or from about 15 to 25 subunits. For example, an oligomer of the invention having 19-20 subunits, a useful length for an antisense oligomer, may have two to seven, e.g. four to six, or three to five, modified linkages, and the remainder unmodified linkages. An oligomer having 14-15 subunits may have two to five, e.g. 3 or 4, modified linkages and the remainder unmodified linkages.

In one embodiment, each morpholino ring structure supports a base-pairing moiety, to form a sequence of base-pairing moieties which is designed to hybridize to a selected target in a cell or in a subject being treated. For example, the base pairing moiety may be a purine or pyrimidine found in native DNA or RNA (A, G, C, T, or U) or an analog, such as hypoxanthine (the base component of the nucleoside inosine) or 5-methyl cytosine.

The preparation of "PMO$^{X1}$" oligomers above are described in, e.g., the co-owned and pending U.S. Patent Application No. 61/349,783, the content of which is incorporated herein by reference in its entirety.

C. dsRNA Molecules Comprising Oligonucleotide Analogs with Modified Terminal Groups In another aspect of the invention, there are provided dsRNA or siRNA molecules comprising an oligomer backbone, the backbone comprising a sequence of one or more morpholino ring structures joined by intersubunit linkages, wherein each such ring structure supports a base-pairing moiety, such that said oligomer can bind in a sequence-specific manner to a target nucleic acid, and wherein the dsRNA comprises at least one modified 3' terminal moiety, at least one modified 5' terminal moiety, or combinations thereof, wherein the oligomer comprises the following structure (C-I):

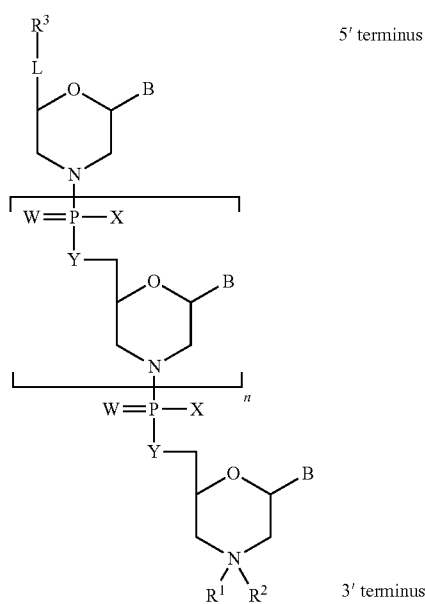

(C-I)

wherein, independently at each occurrence:

$R^1$ is absent, H or $C_1$-$C_6$ alkyl;

$R^2$ and $R^3$ are absent, H, cell-penetrating peptide or $R^4$;

$R^4$ is optionally substituted $C_1$-$C_{30}$ alkyl, optionally substituted $C_3$-$C_8$ cycloalkyl, optionally substituted aryl, optionally substituted $C_1$-$C_{30}$ aralkyl, optionally substituted $C_1$-$C_{30}$ alkylcarbonyl, optionally substituted $C_3$-$C_8$ cycloalkylcarbonyl, optionally substituted $C_3$-$C_8$ cycloalkylalkylcarbonyl, optionally substituted $C_1$-$C_{30}$ arylcarbonyl, optionally substituted $C_1$-$C_{30}$ aralkylcarbonyl, optionally substituted $C_1$-$C_{30}$ alkyloxycarbonyl, optionally substituted $C_3$-$C_8$ cycloalkyloxycarbonyl, optionally substituted $C_1$-$C_{30}$ aryloxycarbonyl or optionally substituted $C_1$-$C_{30}$ aralkyloxycarbonyl;

W is S or O;

X is $NR^5R^6$ or $OR^7$;

Y is O or $NR^8$,

B is a base-pairing moiety;

L is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate and phosphodiester; and n is an integer of 0 or greater; and wherein each of $R^5$, $R^6$, $R^7$ and $R^8$ is independently hydrogen or optionally substituted $C_1$-$C_{12}$ alkyl, and wherein each of $R^5$, $R^6$, $R^7$ and $R^8$ may join with another of $R^5$, $R^6$, $R^7$ or $R^8$ to form an optionally substituted 5, 6 or 7-membered heterocycle comprising one or more N, O or S atoms or combinations thereof; and wherein at least one of $R^2$ or $R^3$ is $R^4$, and provided that both of $R^1$ and $R^2$ are not absent.

In other embodiments of the foregoing, $R^4$ is optionally substituted $C_1$-$C_{30}$ arylcarbonyl. For example, in some specific embodiments $R^4$ has one of the following structures (C-II) or (C-III):

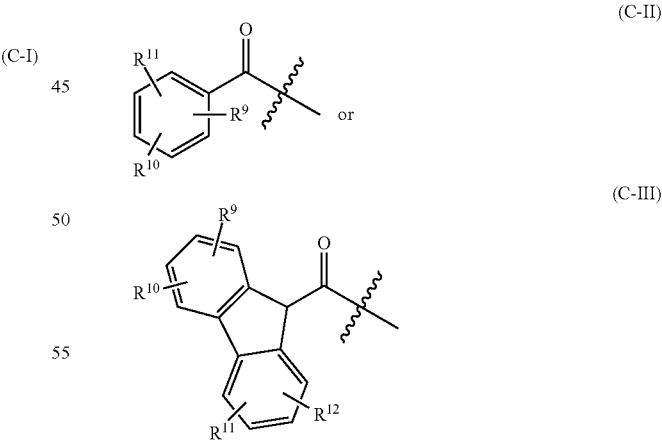

wherein $R^9$, $R^{10}$, $R^{11}$ and $R^{12}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl.

In other further embodiments, $R^4$ has one of the following structures (C-IV), (C-V), (C-VI) or (C-VII).

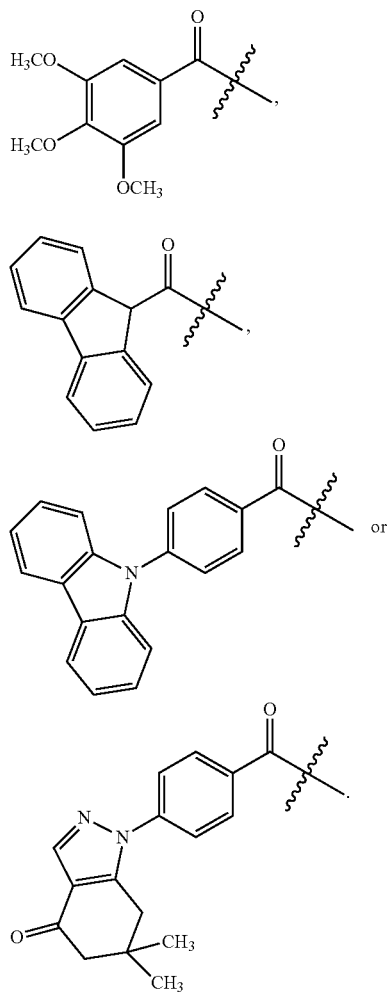

In yet other embodiments of the foregoing, R⁴ is optionally substituted $C_1$-$C_{30}$ alkyl, wherein the optionally substituted $C_1$-$C_{30}$ alkyl comprises one or more double bonds. For example, in some further embodiments R⁴ has one of the following structures (C-VIII), (C-IX) or (C-X):

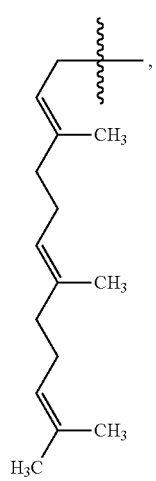

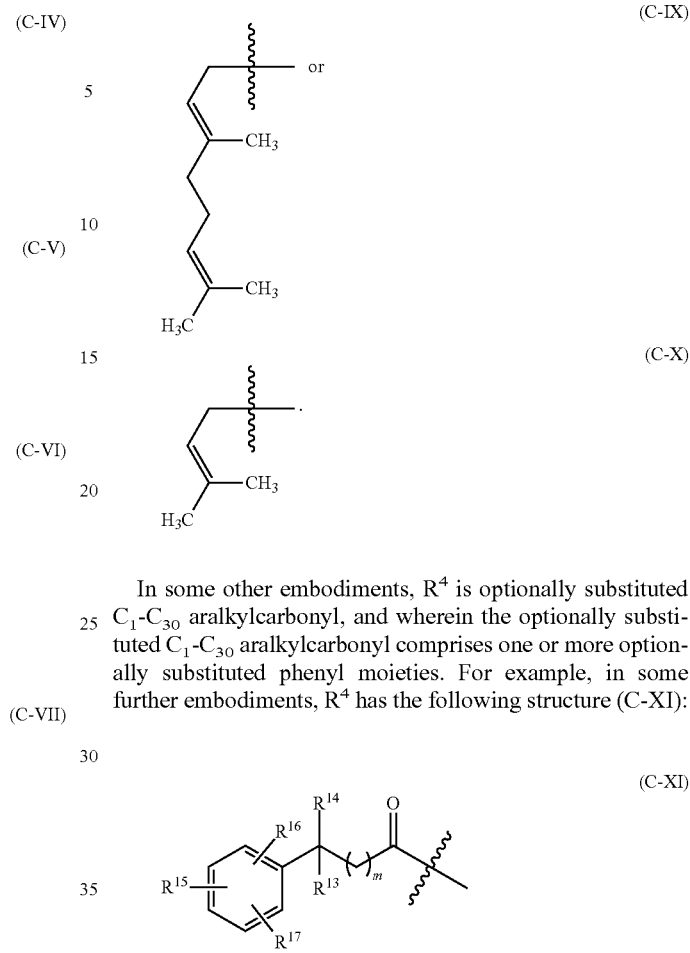

In some other embodiments, R⁴ is optionally substituted $C_1$-$C_{30}$ aralkylcarbonyl, and wherein the optionally substituted $C_1$-$C_{30}$ aralkylcarbonyl comprises one or more optionally substituted phenyl moieties. For example, in some further embodiments, R⁴ has the following structure (C-XI):

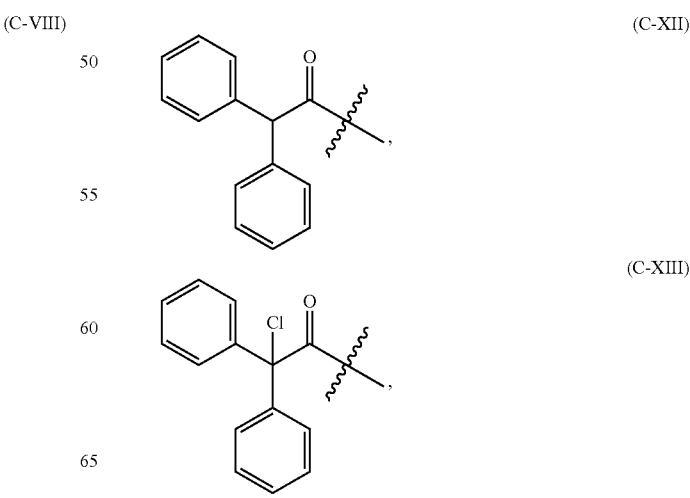

wherein $R^{13}$, $R^{14}$, $R^{15}$, $R^{16}$ and $R^{17}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl and m is an integer from 0 to 6.

In some other specific embodiments, R⁴ has one of the following structures (C-XII), (C-XIII), (C-XIV) or (C-XV):

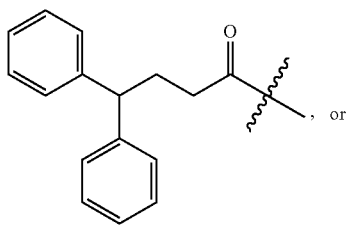

(C-XIV)

, or

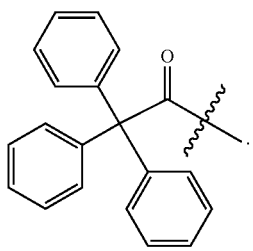

(C-XV)

In yet other embodiments, $R^4$ is optionally substituted $C_1$-$C_{30}$ aralkyl, wherein the optionally substituted $C_1$-$C_{30}$ aralkyl comprises one or more optionally substituted phenyl moieties. For example, in some embodiments, $R^4$ has the following structure (C-XVI):

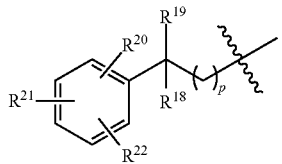

(C-XVI)

wherein $R^{18}$, $R^{19}$, $R^{20}$, $R^{21}$ and $R^{22}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl and p is an integer from 0 to 6.

In some other specific embodiments, $R^4$ has the following structure (C-XVII):

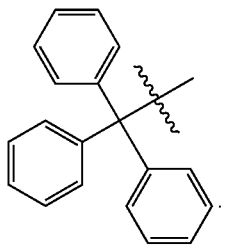

(C-XVII)

In some other embodiments, $R^4$ is optionally substituted $C_3$-$C_8$ cycloalkylcarbonyl, wherein the optionally substituted $C_3$-$C_8$ cycloalkylcarbonyl comprises an optionally substituted cyclohexyl moiety. For example, in some embodiments $R^4$ has the following structure (C-XVIII):

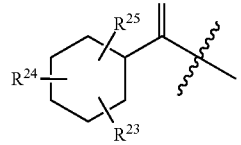

(C-XVIII)

wherein $R^{23}$, $R^{24}$ and $R^{25}$ are each independently hydrogen, halo, optionally substituted $C_1$-$C_{30}$ alkyl, optionally substituted $C_1$-$C_{30}$ alkoxy, optionally substituted aryl, optionally substituted heteroaryl or optionally substituted heterocyclyl.

In other specific embodiments, $R^4$ has the following structure (C-XIX):

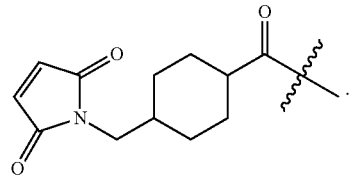

(C-XIX)

In some other embodiments, $R^4$ is optionally substituted $C_1$-$C_{30}$ alkylcarbonyl, and wherein the optionally substituted $C_1$-$C_{30}$ alkylcarbonyl comprises one or more sulfur atoms. For example, in some embodiments $R^4$ has the following structure (XX):

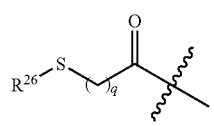

(C-XX)

wherein $R^{26}$ is hydrogen or —$SR^{27}$, wherein $R^{27}$ is hydrogen, optionally substituted $C_1$-$C_{30}$ alkyl, optionally substituted heterocyclyl, optionally substituted aryl or optionally substituted heteroaryl and q is an integer from 0 to 6.

In other specific embodiments, $R^4$ has one of the following structures (C-XXI) or (C-XXII):

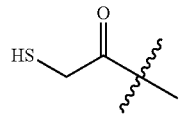

(C-XXI)

or

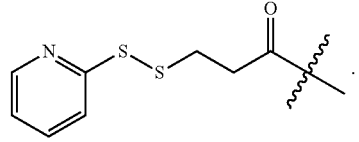

(C-XXII)

In other embodiments, $R^4$ comprises one or more halo atoms. For example, in some embodiments $R^4$ comprises a perfluoro $C_1$-$C_{30}$ alkyl, perfluoro $C_3$-$C_8$ cycloalkyl, perfluoro aryl, perfluoro $C_1$-$C_{30}$ aralkyl perfluoro $C_1$-$C_{30}$ alkylcarbonyl, perfluoro $C_3$-$C_8$ cycloalkylcarbonyl, perfluoro $C_3$-$C_8$ cycloalkylalkylcarbonyl, perfluoro $C_1$-$C_{30}$ arylcarbonyl, perfluoro $C_1$-$C_{30}$ aralkylcarbonyl, perfluoro $C_1$-$C_{30}$ alkyloxycarbonyl, perfluoro $C_3$-$C_8$ cycloalkyloxycarbonyl perfluoro $C_1$-$C_{30}$ aryloxycarbonyl or perfluoro $C_1$-$C_{30}$ aralkyloxycarbonyl. For example in some specific embodiments $R^4$ is p-trifluoromethylphenyl, trifluoromethyltrityl, perfluoropentyl or pentafluorophenyl.

In some embodiments the 3' terminus comprises a modification and in other embodiments the 5' terminus comprises a modification. In other embodiments both the 3' and 5' termini comprise modifications. Accordingly, in some embodiments, $R^2$ is absent and $R^3$ is $R^4$. In other embodiments, $R^3$ is absent and $R^2$ is $R^4$. In yet other embodiments, $R^2$ and $R^3$ are each $R^4$.

In some embodiments, the oligomer comprises a cell-penetrating peptide in addition to a 3' or 5' modification. Accordingly, in some embodiments $R^2$ is cell-penetrating peptide and $R^3$ is $R^4$. In other embodiments, $R^3$ is a cell-penetrating peptide and $R^2$ is $R^4$. In further embodiments of the foregoing, the cell-penetrating peptide is an arginine-rich peptide.

In some embodiments, $R^1$ is methyl, and in other embodiments $R^1$ is absent.

The linker L which links the 5' terminal group to the oligomer may be present or absent. The linker may comprise any number of functional groups and lengths provided the linker retains its ability to link the 5' terminal group to the oligomer and provided that the linker does not interfere with the oligomer's ability to bind to a target sequence in a sequence specific manner. In one embodiment, L comprises phosphorodiamidate and piperazine bonds. For example, in some embodiments L has the following structure (C-XXIII):

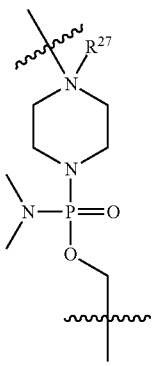

(C-XXIII)

wherein $R^{27}$ is absent, H or $C_1$-$C_6$ alkyl.

In further embodiments, $R^{27}$ is absent, and in other embodiments $R^{27}$ is methyl.

In any of the foregoing embodiments, the oligomer may also comprise any number of modified intersubunit linkages. Accordingly, in one embodiment at least one X is —$NR^5R^6$ and at least one of the intersubunit linkages have the following structure (C-XXIV):

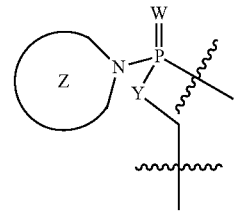

(C-XXIV)

wherein Z represents a 5, 6 or 7 membered optionally substituted heterocycle comprising one or more N, O or S atoms or combinations thereof. For example, in some specific embodiments W and Y are each O.

In other embodiments, at least one of the intersubunit linkages has one of the following structures (C-XXV), (C-XXVI), (C-XXVII) or (C-XXVIII):

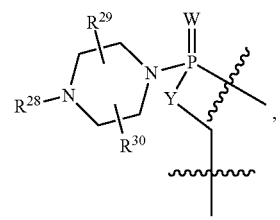

(C-XXV)

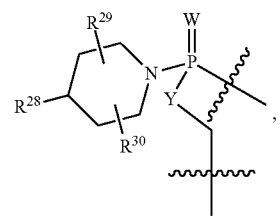

(C-XXVI)

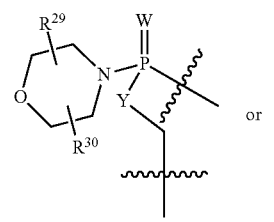

(C-XXVII)

or

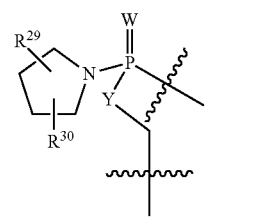

(C-XXVIII)

wherein $R^{28}$, $R^{29}$ and $R^{30}$ are each independently optionally substituted $C_1$-$C_{12}$ alkyl, (—$NR^{31}R^{32}$), —C(=O)$R^{31}$—, optionally substituted aryl, optionally substituted heteroaryl, optionally substituted heterocycle, —$SR^{31}$, or $C_1$-$C_{12}$ alkoxy, wherein each of $R^{31}$ and $R^{32}$ are independently optionally substituted $C_1$-$C_{12}$ alkyl, —$NR^{31}R^{32}$, —C(=O)$R^{31}$—, optionally substituted aryl, optionally substituted heteroaryl, optionally substituted heterocycle, —$SR^{31}$, or $C_1$-$C_{12}$ alkoxy. For example, in some specific embodiments W and Y are each O.

In other embodiments, at least one X is OR⁷ and at least one Y is NR⁸ and the at least one of the intersubunit linkages has the following structure (C-XXIX):

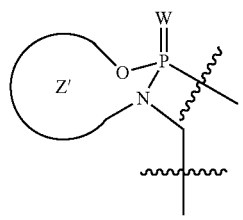

(C-XXIX)

wherein Z' represents a 5, 6 or 7 membered optionally substituted heterocycle comprising one or more N, O or S atoms or combinations thereof. For example, in one embodiment, at least one of the intersubunit linkages has the following structure (C-XXX):

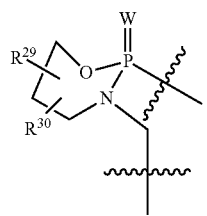

(C-XXX)

wherein $R^{29}$ and $R^{30}$ are each independently optionally substituted $C_1$-$C_{12}$ alkyl, —NR³¹R³², —C(=O)R³¹—, optionally substituted aryl, optionally substituted heteroaryl, optionally substituted heterocycle, —SR³¹, or $C_1$-$C_{12}$ alkoxy, wherein each of $R^{31}$ and $R^{32}$ are independently optionally substituted $C_1$-$C_{12}$ alkyl, —NR³¹R³², oxo —C(=O)R³¹—, optionally substituted aryl, optionally substituted heteroaryl, optionally substituted heterocycle, —SR³¹, or $C_1$-$C_{12}$ alkoxy. For example, in some specific embodiments W and Y are each O.

In other embodiments, at least one X is selected from dimethylamino, piperazyn-1-yl, 4-aminopiperidin-1-yl; N-methyl-N-hexylamino, 4-N-(N-ibu-Cys)piperazin-1-yl, 4-N-(3,4,5-trimethoxybenzoyl)piperazin-1-yl, 4-N-pyrrolidinylpiperidin-1-yl, 4-N-(3-tetrazoylbenzoyl)piperazin-1-yl, 4-N-succinamidopiperazin-1-yl, 4-N-mercaptoacetylpiperazin-1-yl, morpholino-4-yl, S-2-methoxymethylpyrrolindin-1-yl, R-2-methoxymethylpyrrolindin-1-yl, 4-trimethylaminopiperidin-1-yl, 4-guanidinylpiperidin-1-yl and structure (C-XXXI):

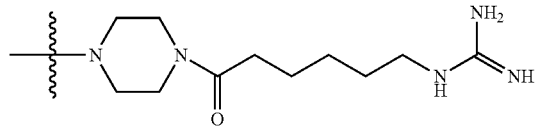

(C-XXXI)

In other embodiments, at least one X and at least one Y may be taken together to form an optionally substituted heterocycle ring of 5, 6 or 7 members comprising one or more N, O or S atoms or combinations thereof.

In some specific embodiments, the oligomer comprises a 3' or 5' terminal modification selected farnesyl; farnesyl methiodide; diphenylacetyl; triphenylmethyl(trityl); geranyl; gernayl methiodide, prenyl, prenyl methiodide; triphenylacetyl; 3,4,5-trimethoxybenzoyl; fluorenyl-9-carboxy; 4-(9H-carbazol-9-yl)benzoyl; 2-chloro-2,2-diphenylacetyl 3,3-diphenylpropyl; 4-((2,5-dioxo-2,5-dihydro-1H-pyrrol-1-yl)methyl)cyclohexanecarboxy; 4-(6,60dimethyl-4-oxo-4,5,6,7-tetrahydro-1H-indazol-1-yl)benzoyl, thioacetyl and thiopropionyl-2-thiopyridyl disulfide. For example, in some embodiments the 3' terminus of the oligomer has one of the following structures:

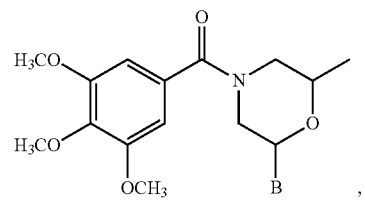

,

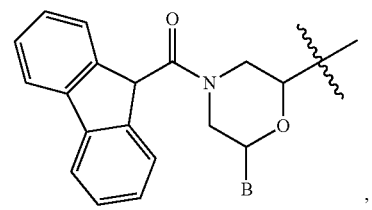

,

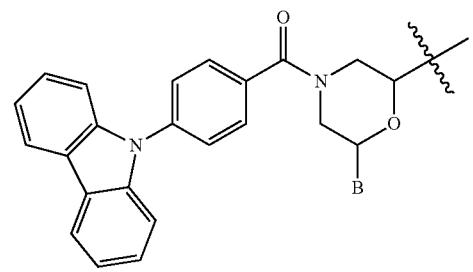

,

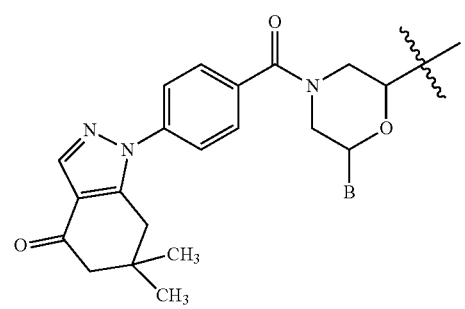

,

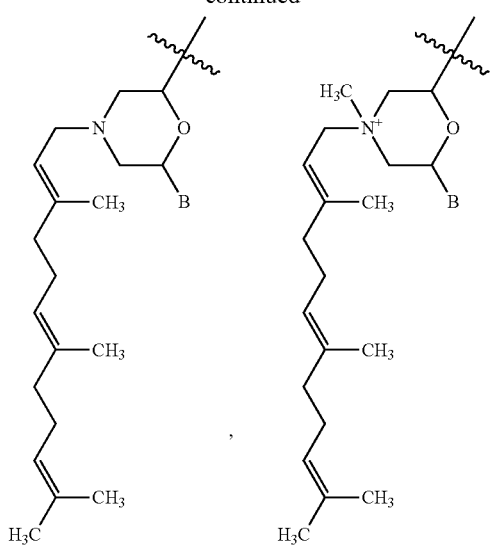
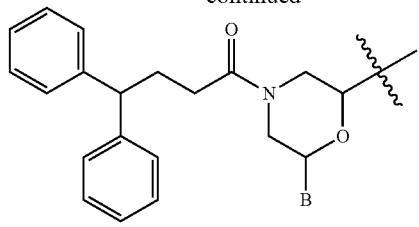
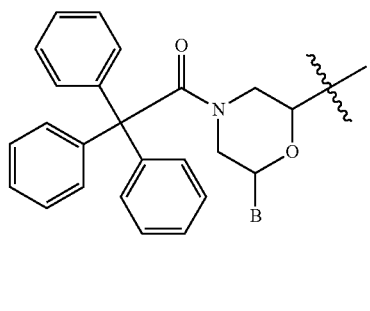
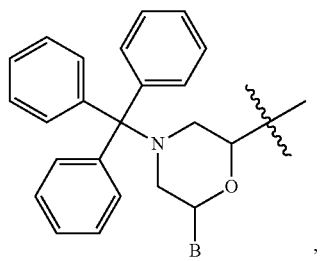
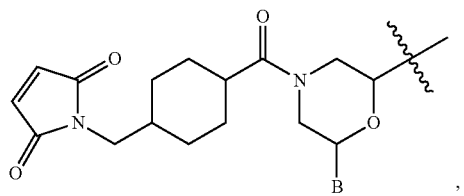
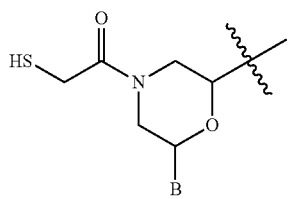
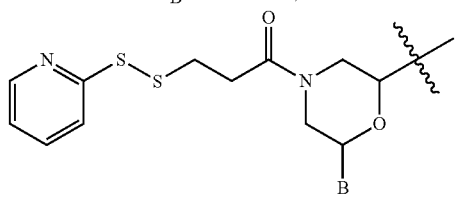
In some other embodiments the 5' terminus of the oligomer has one of the following structures:

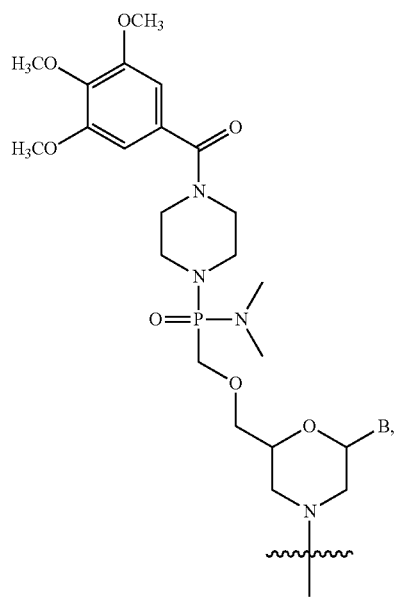
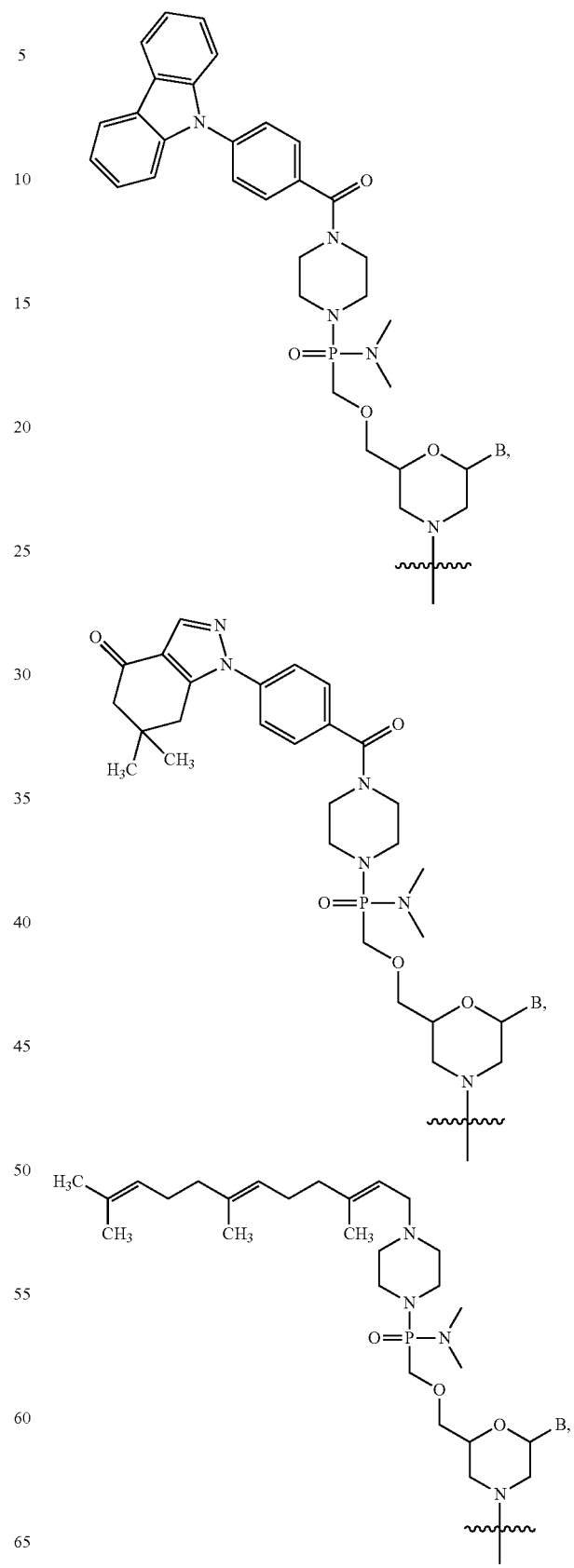

55
-continued
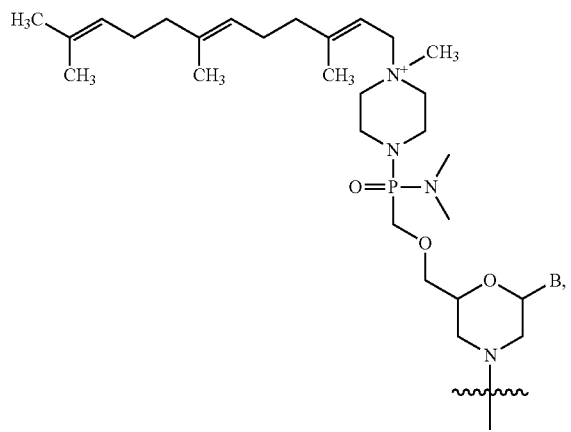
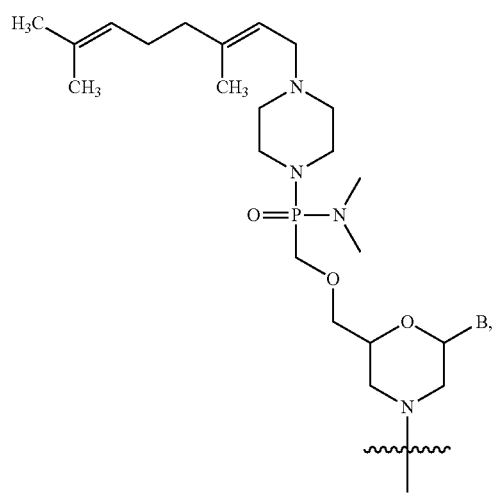
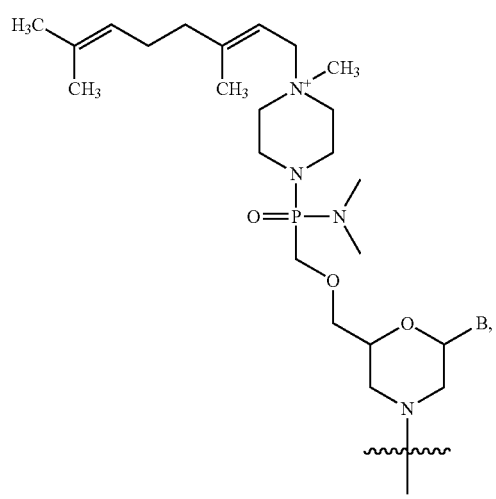
56
-continued
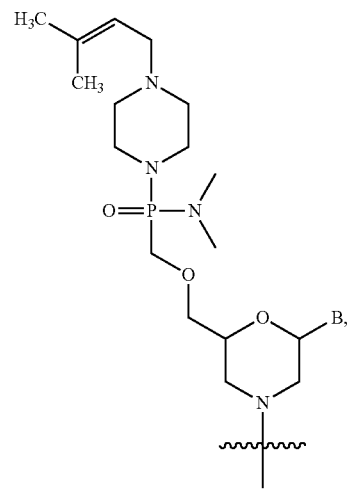
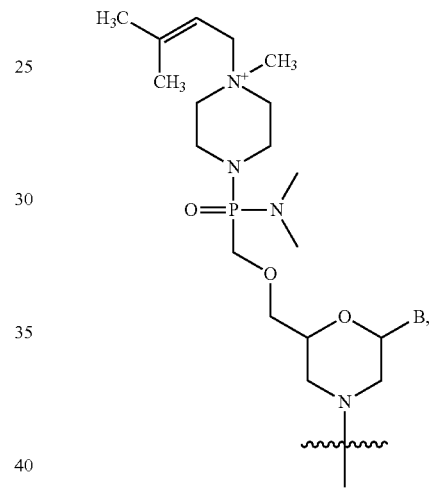
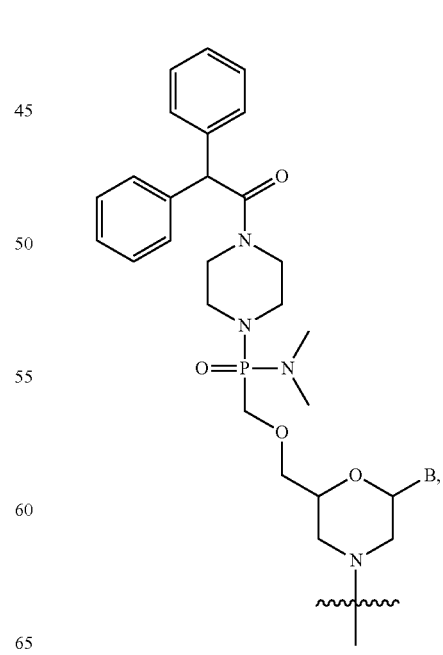

57
-continued
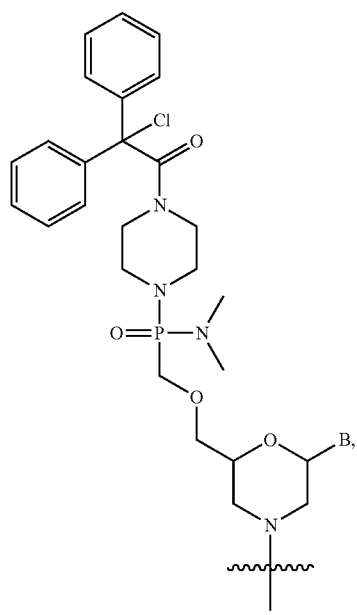
58
-continued
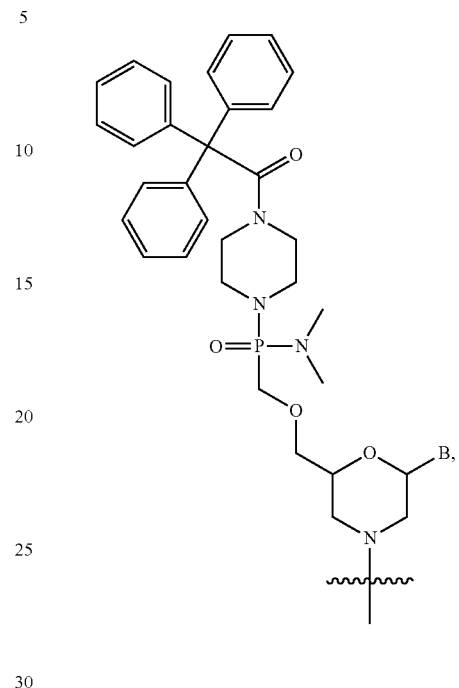
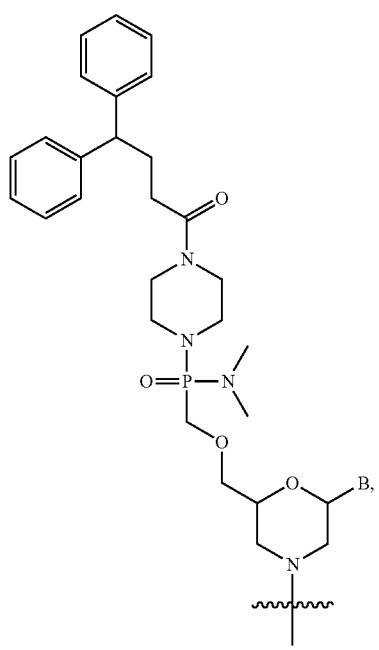
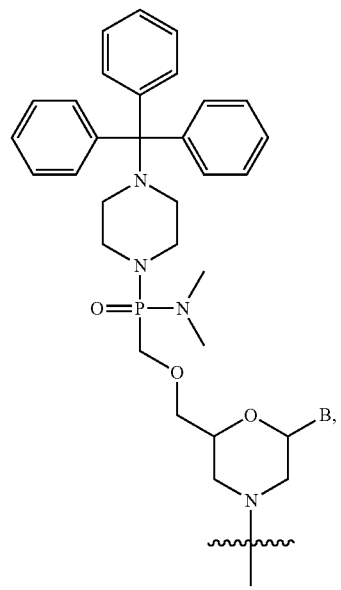

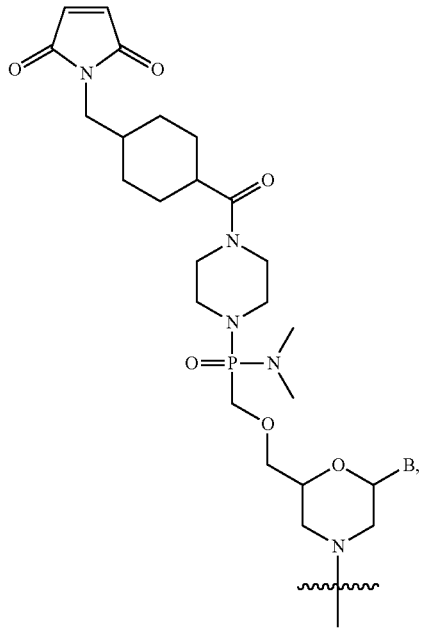

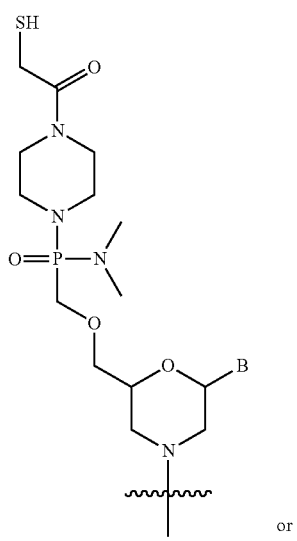

or

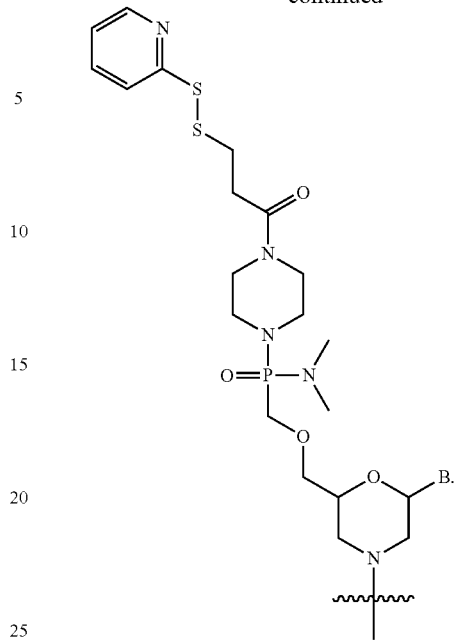

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. The 5' and/or 3' termini may be present in a single stranded overhang within a dsRNA molecule or may be present as part of a blunt ended dsRNA molecule.

In some other embodiments, both the 3' and 5' termini are conjugated to the same terminal group selected from one of the groups noted above.

In another embodiment, the modified terminal groups described herein are conjugated to oligomers containing one or more modified intersubunit linkages as described in co-owned and co-pending U.S. patent application Ser. Nos. 61/349,783 and 11/801,885 which are incorporated into the present application in their entirety.

The present disclosure also provides a method of inhibiting production of a protein comprising exposing a nucleic acid encoding the protein to an oligomer comprising modified termini as disclosed herein.

The preparation of the above "PMO$^{X2}$" oligomers is described in, e.g., the co-owned and pending U.S. Patent Application No. 61/361,878, the content of which is incorporated herein by reference in its entirety.

D. Peptide Transporters

In some embodiments, a dsRNA molecule of the present invention may be conjugated to an arginine-rich peptide transport moiety which is effective to enhance transport of the molecule into cells. In further embodiments, the transport moiety may be attached to a terminal residue of the sense or antisense strand of a dsRNA molecule.

In some embodiments of the foregoing, the peptide transport moiety comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of (X'Y'X')$_p$, (X'Y')$_m$, and (X'Z'Z')$_p$, where p is 2 to 5 and m is 2 to 8.

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit.

In certain embodiments, peptides of this type include those comprising arginine dimers alternating with single Y' subunits, where Y' is preferably Ahx. Examples include peptides having the formula (RY'R)$_p$ (SEQ ID NO:8) or the formula (RRY')$_p$ (SEQ ID NO:9), where Y' is preferably Ahx. In one embodiment, Y' is a 6-aminohexanoic acid subunit, R is arginine and p is 4.

In a further embodiment, each Z' is phenylalanine, and m is 3 or 4. In some embodiments, the conjugated peptide is linked to a terminus of the oligomer via a linker Ahx-B, where Ahx is a 6-aminohexanoic acid subunit and B is a β-alanine subunit, as shown, for example, in FIG. 1D.

In selected embodiments, for each X', the side chain moiety is independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In some embodiments, the Y' subunits are either contiguous, in that no X' subunits intervene between Y' subunits, or interspersed singly between X' subunits. However, in some embodiments the linking subunit may be between Y' subunits. In one embodiment, the Y' subunits are at a terminus of the transporter; in other embodiments, they are flanked by X' subunits. In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Exemplary peptides of this type include those comprising arginine dimers alternating with single Y' subunits, where Y' is preferably Ahx. Examples include peptides having the formula (RY'R)$_4$ (SEQ ID NO:8) or the formula (RRY')$_4$ (SEQ ID NO:9), where Y' is preferably Ahx. In some embodiments, the nucleic acid analog is linked to a terminal Y' subunit, preferably at the C-terminus, as shown, for example, in FIG. 1D. In other embodiments, the linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake may be evidenced by at least a two-fold increase, or in other embodiments a four-fold increase, in the uptake of the compound into mammalian cells relative to uptake of the agent by an attached transport moiety lacking the hydrophobic subunits Y'. In some embodiments, uptake is enhanced at least twenty fold or at least forty fold, relative to the unconjugated compound.

A further benefit of the transport moiety is its expected ability to stabilize a duplex between an antisense oligomer and its target nucleic acid sequence, presumably by virtue of electrostatic interaction between the positively charged transport moiety and the negatively charged nucleic acid. In some embodiments, the number of charged subunits in the transporter is less than 14, as noted above, or in other embodiments between 8 and 11, since too high a number of charged subunits may lead to a reduction in sequence specificity.

Exemplary arginine-rich cell penetrating peptide transporters, including linkers (B or AhxB) are given below in Table 1 below:

TABLE 1

Arginine-rich Cell Penetrating Peptide Transporters

| Peptide | Sequence (N-terminal to C-terminal) | SEQ ID NO: |
|---|---|---|
| (RRAhx)$_4$B | RRAhxRRAhxRRAhxRRAhxB | 1 |
| (RAhxR)$_4$AhxB; (P007) | RAhxRRAhxRRAhxRRAhxRAhxB | 2 |
| (AhxRR)$_4$AhxB | AhxRRAhxRRAhxRRAhxRRAhxB | 3 |
| (RAhx)$_6$B | RAhxRAhxRAhxRAhxRAhxRAhxB | 4 |
| (RAhx)$_8$B | RAhxRAhxRAhxRAhxRAhxRAhxRAhxRAhxB | 5 |
| (RAhxR)$_5$AhxB (CP04057) | RAhxRRAhxRRAhxRRAhxRRAhxRAhxB | 6 |
| (RAhxRRBR)$_2$AhxB; (CP06062) | RAhxRRBRRAhxRRBRAhxB | 7 |

("B" is beta-alanine; "Ahx" is 6-aminohexanoic acid and "R" is arginine)

The preparation and use of peptide transporters as set out above is described in, e.g., U.S. application Ser. No. 12/265, 499, the content of which is incorporated herein by reference in its entirety.

IV. Applications of dsRNA Molecules of the Invention

The modified dsRNA molecules described herein may be used in essentially any context in which dsRNA molecules are employed. Most typically, the molecules will be employed in methods of inhibiting production of a target protein of interest, particularly a target protein associated with a disease or other condition. Accordingly, a nucleic acid encoding such a protein is exposed to a modified dsRNA molecule described herein in order to prevent or inhibit production of the protein. More specifically, the modified dsRNA is preferably actively taken up by mammalian cells, is resistant to nuclease degradation and inhibits the expression of one or more target gene mRNAs by facilitating their RNAi-mediated degradation.

Effective delivery of dsRNA molecule is an important aspect of treatment. Routes of dsRNA delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a dsRNA molecule in the treatment of a viral infection of the skin may be topical delivery, while delivery of a dsRNA molecule for the treatment of a viral respiratory infection may be by inhalation. The molecule may also be delivered directly to the site of viral infection, or to the bloodstream.

The siRNA molecule may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, as is known in the art, liposomes, hydrogels, microspheres, microparticles, gas-filled microbubbles, and the like, may be employed to facilitate delivery and/or uptake of dsRNA molecules into cells.

A. Antiviral Applications

In some embodiments, the present invention provides a method of inhibiting production of a protein, such as a viral protein, comprising exposing a nucleic acid encoding the protein to a dsRNA molecule disclosed herein. In more specific embodiments, for example, dsRNA molecules of the invention can be used to inhibit the replication of an RNA virus having a single-stranded, positive-sense genome and selected from one of the Flaviviridae, Picornoviridae, Caliciviridae, Togaviridae, Arteriviridae, Coronaviridae, Astroviridae and Hepeviridae virus families.

A1. Targeting Stem-Loop Secondary Structure of ssRNA Viruses

In certain embodiments, one class of an exemplary dsRNA molecule of the invention will target a region within the 5'-terminal end 40 bases of the positive-sense RNA strand of the targeted virus. (See, e.g., WO/2006/033933 or U.S. Appn. Pubn. Nos. 20060269911 and 20050096291, which are incorporated herein by reference.)

The method comprises first identifying as a viral target sequence, a region within the 5'-terminal 40 bases of the positive strand of the infecting virus. There is then constructed, by stepwise solid-phase synthesis, a dsRNA comprising at least one modified intersubunit linkage and/or terminal moiety as described herein. For example, in some embodiments the oligomer comprises 20% to 50% such modified linkages, and comprises a targeting sequence of at least a sufficient number of nucleotide residues that are complementary to the virus-genome region to be capable of targeting the virus-genome region for degradation.

In a related aspect, the oligomers can be used in methods of inhibiting, in a mammalian host cell, replication of an infecting RNA virus having a single-stranded, positive-sense genome and selected from the Flaviviridae, Picornoviridae, Caliciviridae, Togaviridae, Arteriviridae, Coronaviridae, Astroviridae and Hepeviridae families. The method includes administering to the infected host cells, a virus-inhibitory amount of a dsRNA as described herein, having a targeting sequence that is complementary to a region within the 5'-terminal 40 bases of the positive-strand viral genome that is capable of forming internal stem-loop secondary structure. The dsRNA is preferably effective, when administered to the host cells, to target the virus RNA for degradation. The oligomer may be administered to a mammalian subject infected with the virus, or at risk of infection with the virus.

Exemplary targeting sequences that target the terminal regions of ssRNA viruses can also be found in U.S. application Ser. No. 11/801,885 and PCT publication WO/2008/036127 which are incorporated herein by reference.

A2. Targeting the First Open Reading Frame of ssRNA Viruses

A second class of exemplary antisense antiviral compounds is for use in inhibition of growth of viruses of the picornavirus, calicivirus, togavirus, coronavirus, and flavivirus families having a single-stranded, positive sense genome of less than 12 kb and a first open reading frame that encodes a polyprotein comprising multiple functional proteins. In particular embodiments, the virus is an RNA virus from the coronavirus family or a West Nile, Yellow Fever or Dengue virus from the flavivirus family. The inhibiting compounds comprise dsRNA molecules as described herein, comprising a targeting base sequence on the antisense strand that is substantially complementary to a viral target sequence which targets the AUG start site region of the first open reading frame of the viral genome. In one embodiment of the method, the oligomer is administered to a mammalian subject infected with the virus. See, e.g., PCT Pubn. No. WO/2005/007805 and US Appn. Pubn. No. 2003224353, which are incorporated herein by reference.

An exemplary target sequence is a region that contains the AUG start site of the first open reading frame (ORF1) of the viral genome. The first ORF generally encodes a polyprotein containing non-structural proteins such as polymerases, helicases and proteases. By "contains the AUG start site" is meant that the target sequence includes at 12 bases of the AUG start site region defined as being 25 bases upstream (i.e. in a 3' direction) and 25 bases downstream (i.e. in a 5' direction) of the AUG start codon.

More generally, exemplary target sites include targets that are conserved between a variety of viral isolates. Other favored sites include the IRES (internal ribosome entry site), transactivation protein binding sites, and sites of initiation of replication. Complex and large viral genomes, which may provide multiple redundant genes, may be efficiently targeted by targeting host cellular genes coding for viral entry and host response to viral presence.

A variety of viral-genome sequences are available from well known sources, such as the NCBI Genbank databases. The AUG start site of ORF1 may also be identified in the gene database or reference relied upon, or it may be found by scanning the sequence for an AUG start codon in the region of the expected ORF1 start site.

A3. Targeting Influenza Virus

A third class of exemplary antisense antiviral compounds is for use in inhibition of the growth of viruses of the Orthomyxoviridae family and in the treatment of a viral infection. In one embodiment, the host cell is contacted with an modified dsRNA as described herein, comprising at least one modified intersubunit linkage and/or terminal group, and comprising a targeting sequence substantially complementary to: 1) the 5' or 3' terminal 25 bases of the negative sense viral RNA segments; 2) the terminal 25 bases of the 5' or 3' terminus of the positive sense cRNA; 3) 45 bases surrounding the AUG start codons of influenza viral mRNAs and; 4) 50 bases surrounding the splice donor or acceptor sites of influenza mRNAs subject to alternative splicing. The modified dsRNA compounds can be used to target any RNA segment of Influenza A, Influenza B and Influenza C viruses. (See, e.g., PCT Pubn. No. WO/2006/047683; U.S. Appn. Pubn. No. 20070004661; and U.S. Appn. No. 61/261,278, which are incorporated herein by reference.)

The disclosed dsRNA molecules are particularly useful in the treatment of influenza virus infection in a mammal. The oligomers may be administered to a mammalian subject infected with the influenza virus, or at risk of infection with the influenza virus.

A4. Targeting Viruses of the Picornaviridae family

A fourth class of exemplary dsRNA molecule is for use in inhibition of growth of viruses of the Picornaviridae family and in the treatment of a viral infection. The disclosed oligomers are particularly useful in the treatment of Enterovirus and/or Rhinovirus infection in a mammal. In this embodiment, the antiviral dsRNA molecules generally contain a targeting sequence that is complementary to a region associated with viral RNA sequences within one of two 32 conserved nucleotide regions of the viral 5' untranslated region. (See, e.g., PCT Pubn. Nos. WO/2007/030576 and WO/2007/030691 or copending and co-owned U.S. application Ser. Nos. 11/518,058 and 11/517,757, which are incorporated herein by reference.)

A5. Targeting Viruses of the Flavivirus family

A fifth class of exemplary antiviral compounds is used in the inhibition of replication of a flavivirus in animal cells. An exemplary dsRNA of this class generally contains a targeting sequence substantially complementary to a region of the virus' positive strand RNA genome that includes at least a portion of the 5'-cyclization sequence (5'-CS) or 3'-CS sequences of the positive strand flaviviral RNA. An exemplary target is the 3'-CS. (See, e.g., PCT Pubn. No. (WO/2005/030800) or copending and co-owned U.S. application Ser. No. 10/913,996, which are incorporated herein by reference.) It is contemplated that the modified dsRNA compounds of the invention could be used to target any essential RNA target region of a flavivirus including the leader sequence and downstream coding regions.

A6. Targeting Viruses of the Nidovirus Family

A sixth class of exemplary antiviral compounds is used in inhibition of replication of a nidovirus in virus-infected animal cells. An exemplary dsRNA generally contains a targeting sequence substantially complementary to the transcriptional regulatory sequences (TRS) in the 5' leader region of the positive-strand viral genome and negative-strand 3' subgenomic region (See, e.g., PCT Pubn. No. WO/2005/065268 or U.S. Appn. Pubn. No. 20070037763, which are incorporated herein by reference.) It is contemplated that the modified dsRNA compounds of the invention could be used to target any essential RNA target region of a nidovirus including the leader sequence and downstream coding regions.

A7. Targeting of Filoviruses

In another embodiment, one or more oligomers as described herein can be used in a method of in inhibiting replication within a host cell of an Ebola virus or Marburg virus, by contacting the cell with a dsRNA as described herein, which contain a targeting base sequence that is complementary to a target sequence composed of at least 12 contiguous bases within an AUG start-site region of a positive-strand mRNA.

The filovirus viral genome is approximately 19,000 bases of single-stranded RNA that is unsegmented and in the antisense orientation. The genome encodes 7 proteins from monocistronic mRNAs complementary to the vRNA.

Target sequences are preferably positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and VP 24, although L, nucleoproteins NP and VP30, are also contemplated. Among these early proteins are favored, e.g., VP35 is favored over the later expressed L polymerase.

In another embodiment, one or more dsRNA molecules as described herein can be used in a method of in inhibiting replication within a host cell of an Ebola virus or Marburg virus, by contacting the cell with an oligomer as described herein, comprising at least one modified terminal group and/or intersubunit linkage as described herein and having a targeting base sequence that is complementary to a target sequence composed of at least 12 contiguous bases within an AUG start-site region of a positive-strand mRNA of the Filovirus mRNA sequences. (See, e.g., PCT Pubn. No. WO/2006/050414 or U.S. Pat. Nos. 7,524,829 and 7,507, 196, which are incorporated herein by reference.)

A8. Targeting of Arenaviruses

In another embodiment, a dsRNA molecule as described herein can be used in a method for inhibiting viral infection in mammalian cells by a species in the Arenaviridae family. In one aspect, the oligomers can be used in treating a mammalian subject infected with the virus. (See, e.g., PCT Pubn. No. WO/2007/103529 or U.S. Pat. No. 7,582,615, which are incorporated herein by reference.)

Table 2 is an exemplary list of illustrative viruses targeted by dsRNA of the invention as organized by their Old World or New World Arenavirus classification.

TABLE 2

Targeted Arenaviruses

| Family | Genus | Virus |
|---|---|---|
| Arenaviridae | Arenavirus | Old World Arenaviruses |
| | | Lassa virus (LASV) |
| | | Lymphocytic choriomeningitis virus (LCMV) |
| | | Mopeia virus (MOPV) |
| | | New World Arenaviruses |
| | | Guanarito virus (GTOV) |
| | | Junín virus (JUNV) |
| | | Machupo virus (MACV) |
| | | Pichinide virus (PICV) |
| | | Pirital virus (PIRV) |
| | | Sabiávirus (SABV) |
| | | Tacaribe virus (TCRV) |
| | | Whitewater Arroyo virus (WWAV) |

The genome of Arenaviruses comprises two single-stranded RNA segments designated S (small) and L (large). In virions, the molar ratio of S- to L-segment RNAs is roughly 2:1. The complete S-segment RNA sequence has been determined for several arenaviruses and ranges from 3,366 to 3,535 nucleotides. The complete L-segment RNA sequence has also been determined for several arenaviruses and ranges from 7,102 to 7,279 nucleotides. The 3' terminal sequences of the S and L RNA segments are identical at 17 of the last 19 nucleotides. These terminal sequences are conserved among all known arenaviruses. The 5'-terminal 19 or 20 nucleotides at the beginning of each genomic RNA are imperfectly complementary with each corresponding 3' end. Because of this complementarity, the 3' and 5' termini are thought to base-pair and form panhandle structures.

Replication of the infecting virion or viral RNA (vRNA) to form an antigenomic, viral-complementary RNA (vcRNA) strand occurs in the infected cell. Both the vRNA and vcRNA encode complementary mRNAs; accordingly, Arenaviruses are classified as ambisense RNA viruses, rather than negative- or positive-sense RNA viruses. The ambisense orientation of viral genes are on both the L- and S-segments. The NP and polymerase genes reside at the 3' end of the S and L vRNA segments, respectively, and are encoded in the conventional negative sense (i.e., they are expressed through transcription of vRNA or genome-complementary mRNAs). The genes located at the 5' end of the S and L vRNA segments, GPC and Z, respectively, are encoded in mRNA sense but there is no evidence that they are translated directly from genomic vRNA. These genes are expressed instead through transcription of genomic-sense mRNAs from antigenomes (i.e., the vcRNA), full-length complementary copies of genomic vRNAs that function as replicative intermediates.

The modified dsRNA compounds of the invention are effective as broad-spectrum anti-arenavirus agents when targeted to the conserved terminal 20 base pair regions of the viral vRNA, vcRNA or mRNA species. Effective targets are found at either the 5' or 3' terminal regions of these RNA species.

A9. Targeting of Respiratory Syncytial Virus

Respiratory syncytial virus (RSV) is the single most important respiratory pathogen in young children. RSV-caused lower respiratory conditions, such as bronchiolitis and pneumonia, often require hospitalization in children less than one-year-old. Children with cardiopulmonary diseases and those born prematurely are especially prone to experience severe disorders from this infection. RSV infection is also an important illness in elderly and high-risk adults, and it is the second—most commonly identified cause of viral pneumonia in older persons (Falsey, Hennessey et al. 2005). The World Health Organization estimates that RSV is responsible for 64 million clinical infections and 160 thousand deaths annually worldwide. No vaccines are currently available for the prevention of RSV infection. Although many major advances in our understanding of RSV biology, epidemiology, pathophysiology, and host-immune-response have occurred over the past few decades, there continues to be considerable controversy regarding the optimum management of infants and children with RSV infection. Ribavirin is the only licensed antiviral drug for treating RSV infection, but its use is limited to high-risk or severely-ill infants. The utility of Ribavirin has been limited by its cost, variable efficacy, and tendency to generate resistant viruses (Marquardt 1995; Prince 2001). The current need for additional effective anti-RSV agents is well-acknowledged.

It is known that peptide conjugated PMO (PPMO) can be effective in inhibiting RSV both in tissue culture and in an in vivo animal model system (Lai, Stein et al. 2008). Effective antisense oligomers designed to target a sequence that includes the 5'-terminal region and translation start-site region of RSV L mRNA, have been shown to have anti-RSV activity in infected cultures of two human airway cell lines and reduced viral titers by greater than 2.0 $\log_{10}$. Intranasal (i.n.) treatment of BALB/c mice with the same antisense oligomers before RSV inoculation produced a reduction in viral titer of 1.2 $\log_{10}$ in lung tissue at day 5 postinfection (p.i.), and attenuated pulmonary inflammation at day 7 postinfection. These data showed that oligomers targeted to the L gene mRNA provided potent anti-RSV activity (Lai, Stein et al. 2008). Therefore, in another embodiment of the present invention, one or more modified dsRNA as described herein can be used in a method of inhibiting replication within a host cell infected with RSV, by contacting the cell with a dsRNA comprising at least one modified intersubunit linkage, or in other embodiments 10% to 50% such modified linkages, and having a targeting base sequence that is complementary to a target sequence composed of at least 12 contiguous bases within an L gene mRNA from RSV.

A10. General Aspects of Antiviral Applications

A10(a). Base Variations

The base pairing moieties (B) may be normal RNA bases (i.e., adenine, guanine, uridine and cytosine) or analogues thereof that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

A10(b). Inhibition of Viral Replication

In one embodiment, the dsRNA molecules of the invention are used in methods for treating infection of a host animal by a virus, by contacting a cell infected with the virus with a dsRNA agent effective to inhibit the replication of the specific virus. The dsRNA agent is administered to a mammalian subject, e.g., human or domestic animal, infected with a given virus, in a suitable pharmaceutical carrier. It is contemplated that the dsRNA arrests or inhibits the replication of the RNA virus in the host. The RNA virus may be preferably decreased in number or eliminated with little or no detrimental effect on the normal growth or development of the host.

A10(c). Administration Methods

In one aspect of the method, the subject is a human subject, e.g., a patient diagnosed as having a localized or systemic viral infection. The condition of a patient may also dictate prophylactic administration of a dsRNA of the invention, e.g. in the case of a patient who (1) is immunocompromised; (2) is a burn victim; (3) has an indwelling catheter; or (4) is about to undergo or has recently undergone surgery. In one embodiment, the dsRNA comprises, at least in part, a phosphorodiamidate morpholino oligomer, contained in a pharmaceutically acceptable carrier, and is delivered orally. In another preferred embodiment, the dsRNA comprises, at least in part, a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

In one embodiment, the dsRNA compound is administered in an amount and manner effective to result in a peak blood concentration of at least 200-400 nM dsRNA molecule. Typically, one or more doses of dsRNA are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the dsRNA is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

A10(d). Monitoring of Treatment

An effective in vivo treatment regimen using the dsRNA molecules of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered dsRNA of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5): 1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A double-stranded ribonucleic acid (dsRNA) molecule for inhibiting the expression of a target gene in a cell, wherein said dsRNA has a length of about 10 to 30 base pairs and comprises at least two sequences that are complementary to each other and wherein a sense strand comprises a first sequence and an antisense strand comprises a second sequence comprising a region of complementarity which is substantially complementary to at least a part of a target gene mRNA, wherein said region of complementarity is less than about 30 nucleotides in length, wherein one or both of the sense or antisense strands comprise an oligomer backbone comprising at least one morpholino subunit joined by intersubunit linkages, wherein each morpholino subunit supports a base-pairing moiety, and wherein the intersubunit linkages comprise a structure selected from the group consisting of (A) and (B) below:

(A) an intersubunit linkage having the following structure (A-I):

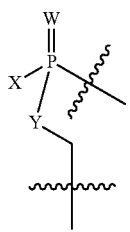

(A-I)

where:
W is S or O;
X is $NR^1R^2$ or $OR^6$;
Y is O or $NR^7$; and
each said linkage (A-I) is selected from:
- (a1) uncharged linkage (a1), where each of $R^1$, $R^2$, $R^6$, and $R^7$ is independently selected from hydrogen and lower alkyl;
- (b1) cationic linkage (b1), where X is $NR^1R^2$, Y is O, and $NR^1R^2$ represents an optionally substituted piperazino group, such that $R^1R^2$ is —CHRCHRN($R^3$)($R^4$)CHRCHR—, where:
  each R is independently H or $CH_3$;
  $R^4$ is H, $CH_3$, or an electron pair; and
  $R^3$ is selected from H, lower alkyl, C(=NH)$NH_2$, Z-L-NHC(=NH)$NH_2$, and [C(O)CHR'NH]$_m$H, where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;
- (b2) cationic linkage (b2), where X is $NR^1R^2$, Y is O, $R^1$ is H or $CH_3$, and $R^2$ is $LNR^3R^4R^5$, where L, $R^3$, and $R^4$ are as defined above, and $R^5$ is H, lower alkyl, or lower (alkoxy)alkyl; and
- (b3) cationic linkage (b3), where Y is $NR^7$, X is $OR^6$, and $R^7$ is $LNR^3R^4R^5$, where L, $R^3$, $R^4$, and $R^5$ are as defined above, and $R^6$ is H or lower alkyl; and at least one of said linkages (A-I) is selected from cationic linkages (b1), (b2), and (b3); and (B) an intersubunit linkage having the following structure (B-I):

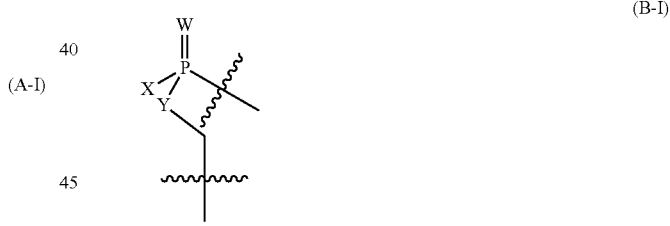

(B-I)

where each intersubunit linkage (B-I) is selected from:
- (a2) linkage (a2) wherein:
  W is S or O;
  X is —N($CH_3$)$_2$; and
  Y is O, and
- (b4) linkage (b4) wherein:
  W is S or O;
  X is $NR^{11}R^{12}$ or $OR^{13}$; and
  Y is O or $NR^{14}$,
  wherein each $R^{11}$ is independently hydrogen or optionally substituted $C_2$-$C_{12}$ alkyl, each of $R^{12}$, $R^{13}$, and $R^{14}$ is independently hydrogen or optionally substituted $C_1$-$C_{12}$ alkyl, or wherein each of $R^{11}$, $R^{12}$, $R^{13}$, and $R^{14}$ may join with another one of $R^{11}$, $R^{12}$, $R^{13}$ or $R^{14}$ to form an optionally substituted 5-, 6- or 7-membered heterocycle comprising one or more N, O, or S atoms or combinations thereof, wherein at least one of the intersubunit linkages has the structure (B-I), and wherein at least one of the intersubunit linkages (B-I) comprises the following structure (B-II):

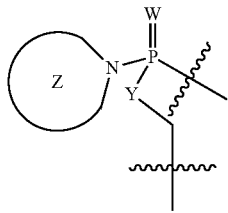
(B-II)

wherein Z represents a 5-, 6-, or 7-membered optionally substituted heterocycle comprising one or more N, O, or S atoms or combinations thereof; and
wherein at least one linkage (B-I) is:
- (b5) linkage (b4), wherein X is 4-aminopiperidin-1-yl;
- (b6) linkage (b4), wherein X is N-methyl-N-hexylamino;
- (b7) linkage (b4), wherein X is 4-N-(N-ibu-Cys)piperazin-1-yl;
- (b8) linkage (b4), wherein X is 4-N-(3,4,5-trimethoxybenzoyl)piperazin-1-yl;
- (b9) linkage (b4), wherein X is 4-N-pyrrolidinylpiperidin-1-yl;
- (b10) linkage (b4), wherein X is 4-N-(3-tetrazoylbenzoyl)piperazin-1-yl;
- (b11) linkage (b4), wherein X is 4-N-succinamidopiperazin-1-yl;
- (b12) linkage (b4), wherein X is 4-N-mercaptoacetylpiperazin-1-yl;
- (b13) linkage (b4), wherein X is morpholino-4-yl;
- (b14) linkage (b4), wherein X is S-2-methoxymethylpyrrolindin-1-yl;
- (b15) linkage (b4), wherein X is R-2-methoxymethylpyrrolindin-1-yl;
- (b16) linkage (b4), wherein X and Y may be taken together to form an optionally substituted heterocycle ring of 5, 6, or 7 members comprising one or more N, O, or S atoms or combinations thereof;
- (b17) linkage (b4), wherein X is 4-trimethylaminopiperidin-1-yl; or
- (b18) linkage (b4), wherein X is 4-guanidinylpiperidin-1-yl.

2. The dsRNA molecule of claim 1, wherein said morpholino subunits have the following structure:

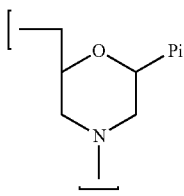
(i)

where Pi is a base-pairing moiety, and said linkages connect the nitrogen atom of (i) to the 5' carbon of an adjacent subunit.

3. The dsRNA molecule of claim 1, wherein each of $R^1$ and $R^2$, in linkages of type (a1), is methyl.

4. The dsRNA molecule of claim 1, wherein said oligomer includes at least two consecutive linkages of type (a1).

5. The dsRNA molecule of claim 1, having a length of about 15 to 25 base pairs.

6. The dsRNA molecule of claim 1, wherein said cationic linkages are of type (b1), where each R is H, $R^4$ is H, $CH_3$, or an electron pair, and $R^3$ is selected from H, $CH_3$, C(=NH)NH_2, and C(O)-L-NHC(=NH)NH_2.

7. The dsRNA molecule of claim 1, wherein said cationic linkages are of type (b1), where each R is H, and each of $R^3$ and $R^4$ is independently H or $CH_3$.

8. The dsRNA molecule of claim 7, wherein each of $R^3$ and $R^4$ is H.

9. The dsRNA molecule of claim 1, wherein said cationic linkages are of type (b2), where L is a linker up to 12 atoms in length having bonds selected from alkyl and alkylamino.

10. The dsRNA molecule of claim 1, wherein W and Y are each O.

11. The dsRNA molecule of claim 1, wherein linkage (b4) has one of the following structures (B-III), (B-IV), (B-V) or (B-VI):

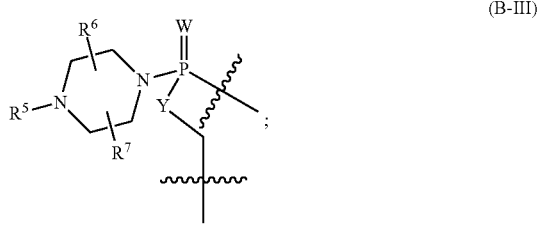
(B-III)

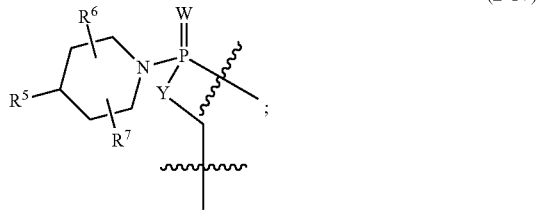
(B-IV)

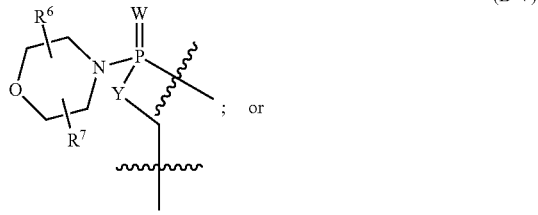
(B-V)

; or

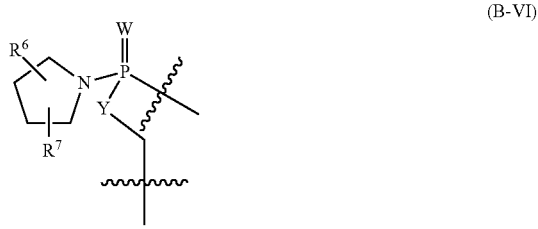
(B-VI)

wherein $R^{15}$, $R^{16}$, and $R^{17}$ are each independently optionally substituted $C_1$-$C_{12}$ alkyl, amino, —C(=O)$R^{18}$—, optionally substituted aryl, optionally substituted heteroaryl, optionally substituted heterocycle, —$SR^{18}$, or $C_1$-$C_{12}$ alkoxy, wherein each $R^{18}$ is independently optionally substituted $C_1$-$C_{12}$ alkyl, optionally substituted aryl, optionally substituted heteroaryl, optionally substituted heterocycle, or $C_1$-$C_{12}$ alkoxy.

12. The dsRNA molecule of claim 1, wherein one of the sense and antisense strands has the following structure (C-I):

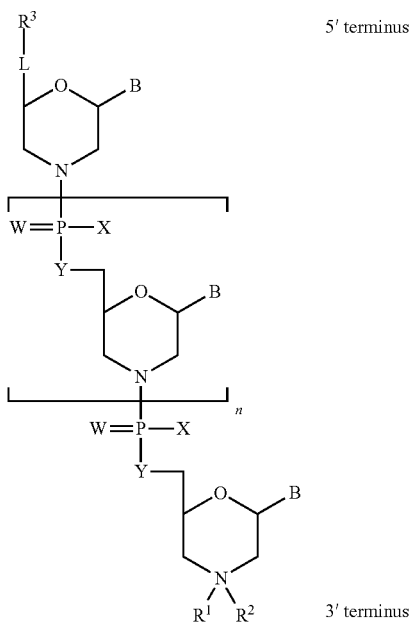

(C-1)

5' terminus

3' terminus wherein, independently at each occurrence:

$R^{19}$ is absent, H, or $C_1$-$C_6$ alkyl;

$R^{20}$ and $R^{21}$ are absent, H, a cell-penetrating peptide, or $R^{22}$;

$R^{22}$ is optionally substituted $C_1$-$C_{30}$ alkyl, optionally substituted $C_3$-$C_8$ cycloalkyl, optionally substituted aryl, optionally substituted $C_1$-$C_{30}$ aralkyl, optionally substituted $C_1$-$C_{30}$ alkylcarbonyl, optionally substituted $C_3$-$C_8$ cycloalkylcarbonyl, optionally substituted $C_3$-$C_8$ cycloalkylalkylcarbonyl, optionally substituted $C_1$-$C_{30}$ arylcarbonyl, optionally substituted $C_1$-$C_{30}$ aralkylcarbonyl, optionally substituted $C_1$-$C_{30}$ alkyloxycarbonyl, optionally substituted $C_3$-$C_8$ cycloalkyloxycarbonyl, optionally substituted $C_1$-$C_{30}$ aryloxycarbonyl, or optionally substituted $C_1$-$C_{30}$ aralkyloxycarbonyl;

W is S or O;

X is $NR^{23}R^{24}$ or $OR^{25}$;

Y is O or $NR^{26}$;

B is a base-pairing moiety;

L' is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate, and phosphodiester; and n is an integer of 0 or greater; and wherein each of $R^{23}$, $R^{24}$, $R^{25}$, and $R^{26}$ is independently hydrogen or optionally substituted $C_1$-$C_{12}$ alkyl, and wherein each of $R^{23}$, $R^{24}$, $R^{25}$, and $R^{26}$ may join with another of $R^{23}$, $R^{24}$, $R^{25}$, or $R^{26}$ to form an optionally substituted 5-, 6-, or 7-membered heterocycle comprising one or more N, O, or S atoms or combinations thereof; and wherein at least one of $R^{20}$ or $R^{21}$ is $R^{22}$, and provided that both of $R^{19}$ and $R^{20}$ are not absent.

13. A method of inhibiting production of a protein, comprising exposing a nucleic acid encoding the protein to a dsRNA molecule of claim 1, wherein the nucleic acid encoding the protein comprises the at least a part of the target gene mRNA.

* * * * *

UNITED STATES PATENT AND TRADEMARK OFFICE
CERTIFICATE OF CORRECTION

Page 1 of 2

PATENT NO. : 10,017,763 B2
APPLICATION NO. : 13/819634
DATED : July 10, 2018
INVENTOR(S) : Patrick L. Iversen It is certified that error appears in the above-identified patent and that said Letters Patent is hereby corrected as shown below:

In the Claims

Claim 11, Column 78, Lines 20-55, should read:

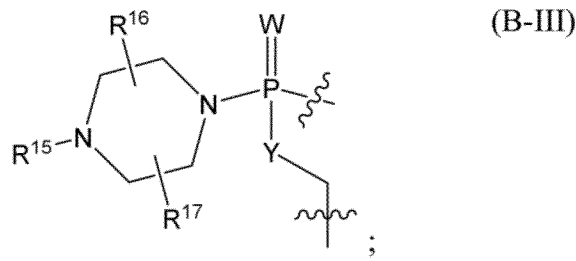

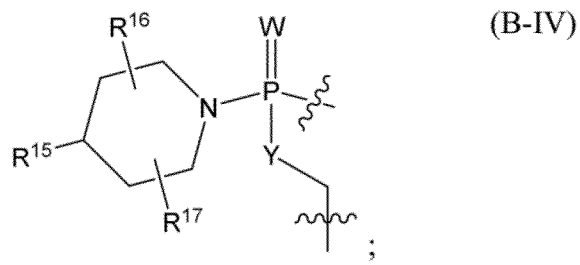

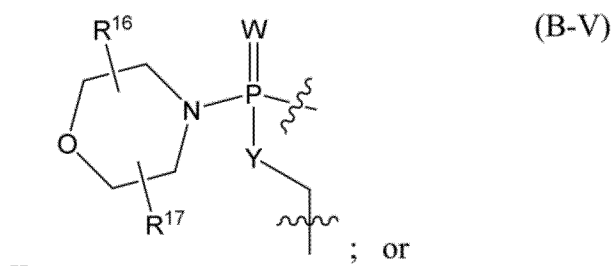

--

Signed and Sealed this
Twelfth Day of May, 2020

Andrei Iancu
*Director of the United States Patent and Trademark Office*

CERTIFICATE OF CORRECTION (continued)
U.S. Pat. No. 10,017,763 B2

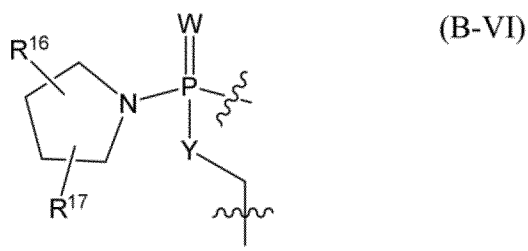

(B-VI)

--.

Claim 12, Column 79, Lines 1-25, should read:

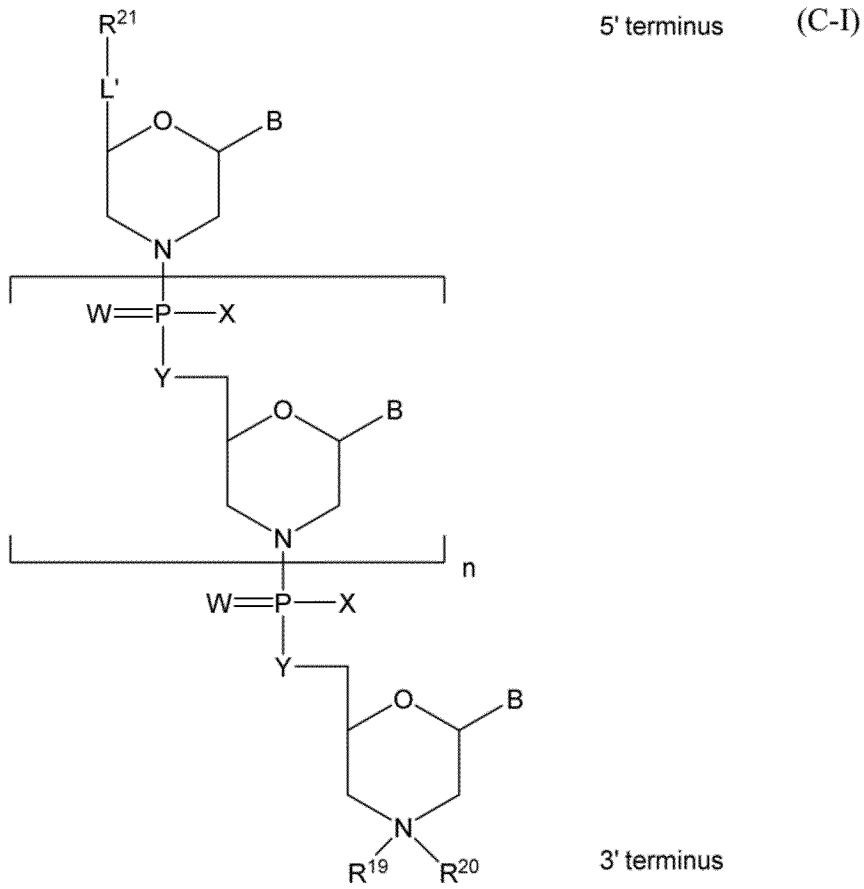

(C-I)

--.

SEQUENCE LISTING

```
<160> NUMBER OF SEQ ID NOS: 10

<210> SEQ ID NO 1
<211> LENGTH: 13
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 3, 6, 9, 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 1

Arg Arg Xaa Arg Arg Xaa Arg Arg Xaa Arg Arg Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 2, 5, 8, 11, 13
<223> OTHER INFORMATION: Acp
<220> FEATURE:
<221> NAME/KEY: MOD_RES
<222> LOCATION: 14
<223> OTHER INFORMATION: bAla
```

```
<400> SEQUENCE: 2

Arg Xaa Arg Arg Xaa Arg Arg Xaa Arg Arg Xaa Arg Xaa Xaa
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 1, 4, 7, 10, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 3

Xaa Arg Arg Xaa Arg Arg Xaa Arg Arg Xaa Arg Arg Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 2, 4, 6, 8, 10, 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 4

Arg Xaa Arg Xaa Arg Xaa Arg Xaa Arg Xaa Arg Xaa Xaa
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 2, 4, 6, 8, 10, 12, 14
<223> OTHER INFORMATION: Acp
<220> FEATURE:
<221> NAME/KEY: MOD_RES
<222> LOCATION: 15
<223> OTHER INFORMATION: bAla

<400> SEQUENCE: 5

Arg Xaa Arg Xaa Arg Xaa Arg Xaa Arg Xaa Arg Xaa Arg Xaa Xaa
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Arginine-rich cell penetrating peptide
      transporter
```

```
<220> FEATURE:
<221> NAME/KEY: MOD_RES
<222> LOCATION: 2, 5, 8, 11, 14, 16
<223> OTHER INFORMATION: Acp
<220> FEATURE:
<221> NAME/KEY: MOD_RES
<222> LOCATION: 17
<223> OTHER INFORMATION: bAla

<400> SEQUENCE: 6

Arg Xaa Arg Arg Xaa Arg Arg Xaa Arg Arg Xaa Arg Arg Xaa Arg Xaa
 1               5                  10                  15

Xaa

<210> SEQ ID NO 7
<211> LENGTH: 14
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 2, 8, 13
<223> OTHER INFORMATION: Acp
<220> FEATURE:
<221> NAME/KEY: MOD_RES
<222> LOCATION: 5, 11, 14
<223> OTHER INFORMATION: bAla

<400> SEQUENCE: 7

Arg Xaa Arg Arg Xaa Arg Arg Xaa Arg Arg Xaa Arg Xaa Xaa
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 2, 5, 8, 11
<223> OTHER INFORMATION: Acp

<400> SEQUENCE: 8

Arg Xaa Arg Arg Xaa Arg Arg Xaa Arg Arg Xaa Arg
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Arginine-rich cell penetrating peptide
      transporter
<220> FEATURE:
<221> NAME/KEY: MOD_RES
<222> LOCATION: 3, 6, 9, 12
<223> OTHER INFORMATION: Acp

<400> SEQUENCE: 9

Arg Arg Xaa Arg Arg Xaa Arg Arg Xaa Arg Arg Xaa
 1               5                  10

<210> SEQ ID NO 10
<211> LENGTH: 17
<212> TYPE: PRT
<213> ORGANISM: Artificial Sequence
```

```
<220> FEATURE:
<223> OTHER INFORMATION: Arginine-rich cell penetrating peptide
      transporter
<220> FEATURE:
<221> NAME/KEY: MOD_RES
<222> LOCATION: 2, 4, 6, 8, 10, 12, 14, 16
<223> OTHER INFORMATION: Acp
<220> FEATURE:
<221> NAME/KEY: MOD_RES
<222> LOCATION: 17
<223> OTHER INFORMATION: bAla

<400> SEQUENCE: 10

Arg Xaa Arg Xaa Arg Xaa Arg Xaa Arg Xaa Arg Xaa Arg Xaa Arg Xaa
 1               5                  10                  15

Xaa
```